US012766126B2

(12) United States Patent
Bradley et al.

(10) Patent No.: US 12,766,126 B2
(45) Date of Patent: Oct. 20, 2026

(54) METHOD OF USE FOR BENZOFURAN COMPOUNDS

(71) Applicant: Tampa Bay Research Institute, Inc., St. Petersburg, FL (US)

(72) Inventors: William Bradley, Seminole, FL (US); Amara Davis, Columbus, OH (US); Claire O'Connor, Denver, CO (US); Jessica Mandula, Columbus, OH (US); Nicole Perekhodko, Clearwater, FL (US); Akiko Tanaka, Clearwater, FL (US)

(73) Assignee: Tampa Bay Research Institute, Inc., St. Petersburg, FL (US)

( * ) Notice: Subject to any disclaimer, the term of this patent is extended or adjusted under 35 U.S.C. 154(b) by 0 days.

(21) Appl. No.: 19/217,172

(22) Filed: May 23, 2025

(65) Prior Publication Data

US 2025/0381165 A1 Dec. 18, 2025

Related U.S. Application Data

(63) Continuation of application No. PCT/US2024/031179, filed on May 25, 2024.

(51) Int. Cl.

| | |
|---|---|
| ***A61K 31/343*** | (2006.01) |
| ***A61K 40/19*** | (2025.01) |
| ***A61K 40/24*** | (2025.01) |
| ***A61K 40/42*** | (2025.01) |
| ***A61P 35/00*** | (2006.01) |
| ***C12N 5/0783*** | (2010.01) |

(52) U.S. Cl.

CPC ............ *A61K 31/343* (2013.01); *A61K 40/19* (2025.01); *A61K 40/24* (2025.01); *A61K 40/42* (2025.01); *A61P 35/00* (2018.01); *C12N 5/0636* (2013.01); *A61K 2239/39* (2023.05); *C12N 2501/24* (2013.01); *C12N 2501/50* (2013.01); *C12N 2501/999* (2013.01); *C12N 2502/1121* (2013.01)

(58) Field of Classification Search

None

See application file for complete search history.

(56) References Cited

PUBLICATIONS

Haraguchi et al (Cancer Immunnol Res, 2(10 Supplement):B29, 2015, abstract only).*

National Center for Biotechnology Information (2025). PubChem Compound Summary for CID 637542, P-Coumaric Acid. Retrieved Nov. 26, 2025 from https://pubchem.ncbi.nlm.nih.gov/compound/P-Coumaric-Acid.*

National Center for Biotechnology Information (2025). PubChem Compound Summary for CID 23005307, (2E)-3-(1-benzofuran-5-yl)prop-2-enoic acid. Retrieved Nov. 26, 2025 from https://pubchem.ncbi.nlm.nih.gov/compound/2E_-3-_1-benzofuran-5-yl_prop-2-enoic-acid.*

Guo et al (Natural Product Research, 31:1, 16-21, 2017).*

Chen et al (International Journal of Biological Macromolecules, 297 (2025): 139778, pp. 1-14).*

Yao et al (J. Med. Chem. 2020, 63, 8157-8178, 2020).*

Miao et al (RSC Adv., 2019, 9, 27510-27540).*

Abualrous, et al., F pocket flexibility influences the tapasin dependence of two differentially disease-associated MHC Class I proteins. European journal of immunology. 2015;45(4):1248-57.

Abualrous, et al., The Carboxy Terminus of the Ligand Peptide Determines the Stability of the MHC Class I Molecule H-2K b: A Combined Molecular Dynamics and Experimental Study. PloS One. 2015; 10(8):e0135421.

Adibi & Soleimanpour, Functional characterization of dipeptide transport system in human jejunum. J Clin Invest. May 1974; 53(5):1368-74.

Adibi, et al., Influence of molecular structure on half-life and hydrolysis of dipeptides in plasma: importance of glycine as N-terminal amino acid residue. Metabolism. 1986; 35(9):830-6.

Adiko, et al., Intracellular transport routes for MHC I and their relevance for antigen cross-presentation. Front Immunol. 2015I 6:335.

Aguilera-Montilla, et al., Aryl hydrocarbon receptor contributes to the MEK/ERK-dependent maintenance of the immature state of human dendritic cells. Blood. Apr. 11, 2013; 121(15):e108-e17.

Anjanappa, et al., Structures of peptide-free and partially loaded MHC class I molecules reveal mechanisms of peptide selection. Nat Commun. 2020; 11:1314.

Belizaire & Unanue, Targeting proteins to distinct subcellular compartments reveals unique requirements for MHC class I and II presentation. Proc Natl Acad Sci USA. Oct. 13, 2009; 106(41):17463-17468.

Boulanger, et al., Absence of tapasin alters immunodominance against a lymphocytic choriomeningitis virus polytope. Journal Immunol. 2010; 184(1):73-83.

Blum, et al., Pathways of antigen processing. Ann Rev Immunol. 2013;31:443-473.

(Continued)

*Primary Examiner* — Brad Duffy

(74) *Attorney, Agent, or Firm* — Prometheus IP PLLC; Robert Varkonyi

(57) ABSTRACT

An orally bioavailable benzofuran is provided which possesses in vitro and in vivo capabilities able to overcome issues in loading of antigenic peptide on major histocompatibility class I complexes, including on the surface of professional antigen presenting cells. The design of immunotherapies such as dendritic cell vaccines, optimal binding of the antigenic peptides to MHC class I complexes is a major challenge. Current therapeutic peptide loading is expensive, labor-intensive, or requires in vitro manipulation. Models demonstrate that the benzofuran enhances T-cell activation through increased peptide binding to cell surface MHC class I complexes. Molecular docking studies indicate the benzofuran binds the F pocket of MHC class I in a similar manner to high-affinity peptides and TAPBPR, aiding in the targeted loading of exogenous peptides. The therapeutic potential was demonstrated when using PLGA particles of BzFβ were injected intramuscularly, and significantly inhibited the development of E.G7-OVA tumors.

23 Claims, 22 Drawing Sheets

Specification includes a Sequence Listing.

(56) References Cited

PUBLICATIONS

Carretero-Iglesia, et al., High peptide dose vaccination promotes the early selection of tumor antigen-specific CD8 T-cells of enhanced functional competence. Front Immunol. 2019; 10:3016.
Celli, et al., Decoding the dynamics of T cell-dendritic cell interactions in vivo. Immunol Rev. Feb. 2008; 221(1):182-7.
Chai, et al., Comprehensive study of the intestinal absorption of four phenolic compounds after oral administration of Ananas comosus leaf extract in vivo and in vitro. Afr J Pharm Pharmacol. Jul. 2013; 7(26):1781-92.
Compeer, et al., Antigen processing and remodeling of the endosomal pathway: requirements for antigen cross-presentation. Front Immunol. 2012; 3:37.
Daina, et al., SwissADME: a free web tool to evaluate pharmacokinetics, drug-likeness and medicinal chemistry friendliness of small molecules. Sci Rep. Mar. 3, 2017; 7(1):1-13.
Davis, et al., Natural killer cell adoptive transfer therapy: exploiting the first line of defense against cancer. Cancer J. Nov.-Dec. 2015; 21(6):486491.
Day, et al., Direct delivery of exogenous MHC class I molecule-binding oligopeptides to the endoplasmic reticulum of viable cells. Proc Natl Acad Sci USA. Jul. 22, 1997; 94(15):8064-8069.
Eisen, et al., Promiscuous binding of extracellular peptides to cell surface class I MHC protein. Proc Natl Acad Sci USA. Mar. 20, 2012; 109(12):4580-4585.
Elliot & Williams, The optimization of peptide cargo bound to MHC class I molecules by the peptide-loading complex. Immunol. Rev. Sep. 23, 2005; 207(1): 89-99.
Goyvaerts & Breckpot, Pros and cons of antigen-presenting cell targeted tumor vaccines. J Immunol Res. 2015; 2015:78634.
Hafstrand, et al., Successive crystal structure snapshots suggest the basis for MHC class I peptide loading and editing by tapasin. Proc Nat Acad Sci U.S.A. Mar. 12, 2019; 116(11):5055-5060.
Hein, et al., Peptide-independent stabilization of MHC class I molecules breaches cellular quality control. J Cell Sci. Jul. 1, 2014; 127(13):2885-2897.
Hewitt, The MHC calss I antigen presentation pathway: strategies for viral immune evasion. Immunol. Oct. 2003; 110(2):163-1692222.
Iman, et al., Molecular docking analysis and molecular dynamics simulation study of ameltolide analogous as a sodium channel blocker. Turk J Chem. 2015;39(2):306-316.
Jiang, et al., Crystal structure of a TAPBPR-MHC I complex reveals the mechanism of peptide editing in antigen presentation. Science. Nov. 24, 2017; 358(6366):1064-1068.
Jendresen, et al., An improved CPRG colorimetric ligand-receptor signal transduction assay based on beta-galactosidase activity in mammalian BWZ-reporter cells. J Pharmacol Toxicol Methods. 2018; 90:67-75.
Joffre, et al., Cross-presentation by dendritic cells. Nat Rev Immunol. Aug. 2012; 12(8):557-569.
Karttunen, et al., Detection of rare antigen-presenting cells by the lacZ T-cell activation assay suggests an expression cloning strategy for T-cell antigens. Proc Natl Acad Sci USA. Jul. 1, 1992; 89(13):6020-4.
Kastenmüller, et al., Dendritic cell-targeted vaccines—hope or hype? Nat Rev Immunol. 2014; 14(10):705-11.
Kiama, et al., Evaluation of phagocytic activity in human monocyte-derived dendritic cells. J Aerosol Med. Sep. 2001; 14(3):289-299.
Leavy, Antigen presentation: cross-dress to impress. Nat Rev Immunol. May 2011; 11(5):302.
Lin, et al., Soluble CD83 alleviates experimental autoimmune uveitis by inhibiting filamentous actin-dependent calcium release in dendritic cells. Front Immunol. 2018; 9:1567.
Luo, et al., Mitomycin C enhanced the efficacy of PD-L1 blockade in non-small cell lung cancer. Signal Transduct Target Ther. 2020; 5(1):141-114).
Madden, The three-dimensional structure of peptide-MHC complexes. Annual review of immunology. Apr. 1995; 13(1):587-622.
Mage, et al., The peptide-receptive transition state of MHC class I molecules: insight from structure and molecular dynamics. J Immunol. Aug. 1, 2012; 189(3):1391-1399.
Montealegre, et al., Dissociation of β2-microglobulin determines the surface quality control of major histocompatibility complex class I molecules. The FASEB Journal. Jul. 2015; 29(7):2780-2788.
Morris, et al., AutoDock4 and AutoDockTools4: Automated docking with selective receptor flexibility. J Comput Chem. Dec. 2009; 30(16):2785-2791.
Nakamura, et al., Characterization of mouse melanoma cell lines by their mortal malignancy using an experimental metastatic model. Life Sci. Jan. 4, 2002; 70(7):791-798.
Ndombera, et al., Pharmacokinetic, physicochemical and medicinal properties of n-glycoside anti-cancer agent more potent than 2-deoxy-d-glucose in lung cancer cells. J Pharma Pharmacol. 2019; 7:165-176, doi: 10.17265/2328-2150/2019.04.003.
Neerincx & Boyle, Properties of the tapasin homologue TAPBPR. Curr Opin Immunol. Jun. 2017; 46:97-102.
Newey & Smyth, The intestinal absorption of some dipeptides. Journal Physiol. Jan. 28, 1959; 145(1):48-56.
Pos, et al., Crystal structure of the HLA-DM-HLA-DR1 complex defines mechanisms for rapid peptide selection. Cell. Dec. 21, 2012; 151(7):1557-1568.
Ranjith & Ravikumar, SwissADME predictions of pharmacokinetics and drug-likeness properties of small molecules present in Ipomoea mauritiana Jacq. J Pharmacogn Phytochem. Sep.-Oct. 2019; 8(5):2063-73.
Reynisson, et al., NetMHCpan-4.1 and NetMHCIIpan-4.0: improved predictions of MHC antigen presentation by concurrent motif deconvolution and integration of MS MHC eluted ligand data. Nucleic Acids Res. Jul. 2, 2020; 48(W1):W449-W54.
Remesh, et al. Unconventional peptide presentation by major histocompatibility complex (MHC) class I allele HLA-A* 02: 01: Breaking Confinement. J Biol Chem. Mar. 31, 2017; 292(13):5262-70.
Rock, et al., Present yourself! By MHC class I and MHC class II molecules. Trends Immunol. Nov. 2016; 37(11):724-37.
Sadasivan, et al., Roles for calreticulin and a novel glycoprotein, tapasin, in the interaction of MHC class I molecules with TAP. Immunity. 1996; 5(2):103-114.
Saini, et al., Not all empty MHC class I molecules are molten globules: Tryptophan fluorescence reveals a two-step mechanism of thermal denaturation. Molecular immunology. Jul. 2013; 54(3-4):386-396.
Saini, et al., Dipeptides promote folding and peptide binding of MHC class I molecules. Proc Natl Acad Sci USA. Sep. 17, 2013; 110(38):15383-15388.
Saini, et al., Dipeptides catalyze rapid peptide exchange on MHC class I molecules. Proc Natl Acad Sci USA. Jan. 6, 2015; 112(1):202-207.
Saini, et al., Empty peptide-receptive MHC class I molecules for efficient detection of antigen-specific T cells. Science Immunol. Jul. 19, 2019; 4(37):e9039.
Sei, et al. Peptide-MHC-I from endogenous antigen outnumber those from exogenous antigen, irrespective of APC phenotype or activation. PLoS Pathog. Jun. 2015; 11(6):e1004941.
Spiliotis, et al., Selective export of MHC class I molecules from the ER after their dissociation from TAP. Immunity. 2000; 13(6):841-51.
Thirdborough, et al., Tapasin shapes immunodominance hierarchies according to the kinetic stability of peptide—MHC class I complexes. Eur J Immunol. Feb. 2008; 38(2):364-9.
Thomas & Tampe, Structure of the TAPBPR-MHC I complex defines the mechanism of peptide loading and editing. Science. Nov. 24, 2017; 358(6366):1060-1064.
Townsend & Bodmer, Antigen recognition by class I-restricted T lymphocytes. Annu Rev Immunol. 1989; 7:601-624.
Williams, et al., Optimization of the MHC class I peptide cargo is dependent on tapasin. Immunity Apr. 2002; 16(4):509-520.
Wang, et al., Direct loading of CTL epitopes onto MHC class I complexes on dendritic cell surface in vivo. Biomaterials. Nov. 2018; 182:92-103.

(56) References Cited

PUBLICATIONS

Wu, et al., Dual role of 3-methyladenine in modulation of autophagy via different temporal patterns of inhibition on class I and III phosphoinositide 3-kinase. J Biol Chem. Apr. 2, 2010; 285(14):10850-10861.

Burkholz, et al., T-cell targeted immunotherapy against the tumor associated antigen survivin (BIRC5) as a potential neoadjuvant immunotherapy for triple negative breast cancer.

Harris, et al., A synthetic peptide CTL vaccine targeting nucleocapsid confers protection from SARS-CoV-2 challenge in rhesus macaques. Vaccines (Basel). May 18, 2021;9(5):520.

Celis, Getting peptide vaccines to work: just a matter of quality control? J Clin Invest. Dec. 2002; 110(12):1765-8.

Luo, et al., Mitomycin C enhanced the efficacy of PD-L1 blockade in non-small cell lung cancer. Signal Transduct Target Ther. Aug. 28, 2020;5(1):141.

Palankar, et al., Controlled intracellular release of peptides from microcapsules enhances antigen presentation on MHC class I molecules. Small. Oct. 2009; 5(19):2168-76.

Lewis, et al., Microparticle surface modifications targeting dendritic cells for non-activating applications. Biomaterials. Oct. 2021; 33(29):7221-32.

* cited by examiner

METHOD OF USE FOR BENZOFURAN COMPOUNDS

FIELD OF INVENTION

The invention relates generally to pharmaceutical compositions and their use. Specifically, the invention discloses compounds that modulate dendritic and antigen presenting cell (APC) response, immune response, and enhance vaccine regimes.

INCORPORATION OF SEQUENCE LISTING

A sequence listing entitled "TBRI BZF Sequence Listing 2025-01.xml", created on Jan. 6, 2026 and containing 4.40 kilobytes, filed on Jan. 12, 2026 is hereby incorporated by reference.

BACKGROUND OF INVENTION

All nucleated cells display major histocompatibility complex (MHC) class I molecules on their cell surface. Through the MHC class I complex, cells display peptides from endogenous proteins to assist in promoting immunological self-tolerance. The MHC class I system is also one of the body's key defense systems, displaying peptides derived from a wide variety of mutated-self proteins and infectious agents, enabling it to function as an initial safeguard against the development of cancer and overwhelming infections (Davis, et al., Natural killer cell adoptive transfer therapy: exploiting the first line of defense against cancer. Cancer J. 2015 Nov-Dec; 21 (6): 486-91). Activation of this defense is achieved through coordinated activity of professional antigen-presenting cells (APC) including B cells, macrophages and dendritic cells (DC), while the later two capture and present antigens to T cells, DC are up to 1000-fold more efficient in activating T cells (Goyvaerts & Breckpot, Pros and cons of antigen-presenting cell targeted tumor vaccines. J Immunol Res. 2015; 2015:785634). This advantage in directing T cell activation is associated with their increased surface area due to eponymous dendritic cytoplasmic protrusions and their ability to present antigens in a myriad of manners.

DCs can not only present peptides generated from endogenous proteins through direct presentation, but they can also acquire and process exogenous particulates and present them through a mechanism known as cross-presentation. In addition, DCs can obtain antigenic peptides directly from another cell displaying the requisite peptide on its surface, a process described as cross-dressing (Sei, et al., Peptide-MHC-I from endogenous antigen outnumber those from exogenous antigen, irrespective of APC phenotype or activation. PLOS Pathog. 2015 Jun. 24;11 (6): e1004941; Leavy, Antigen presentation: cross-dress to impress. Nat Rev Immunol. 2011 May; 11 (5): 302-3). Each of these presentation methods results in the surface display of MHC class I bound with peptide, along with the presence of specific costimulatory molecules, resulting in the activation of antigen specific CD8 cytotoxic T cells (CTLs) to trigger a robust and targeted immune response.

The two predominant methods for MHC class I presentation specific to APCs are by direct presentation, where an infected DC processes endogenous proteins for display as cell surface MHC class I peptide complexes, or by cross-presentation, where antigens are acquired from extracellular fluids via endocytosis or by engulfing infected cells by phagocytosis (Rock, et al., Present yourself! By MHC class I and MHC class II molecules. Trends Immunol. 2016 Nov; 37 (11): 724-37). Cross-presentation appears to be the primary method DCs utilize to present peptides on the MHC class I complex. In cross-presentation material is taken up through receptor-mediated endocytosis and is digested through either cytosolic or lysosomal proteases. The resulting peptides then enter the peptide loading complex in the cytosol or endosomal compartments where they bind with MHC class I and are shuttled to the cell surface. Once on the cell surface the MHC class I peptide complex can be detected by CD8+ T cells, allowing for effective immune surveillance (Rock, et al., Present yourself! By MHC class I and MHC class II molecules. Trends Immunol. 2016 Nov; 37 (11): 724-37).

The process by which the peptide bound MHC class I complexes are formed is similar throughout cells, with some variations. In dendritic cells, newly synthesized MHC proteins enter the endoplasmic reticulum (ER), where MHC molecules are bound to the MHC class I light chain beta 2-microglobulin (β2m) to form the protein receptive structure of the MHC class I in the ER. Stabilization via calreticulin binding enables peptides to enter the binding region of the MHC class I (Sadasivan, et al., Roles for calreticulin and a novel glycoprotein, tapasin, in the interaction of MHC class I molecules with TAP. Immunity. 1996 Aug; 5 (2): 103-14). This binding region of both human and murine MHC class I proteins is made up of amino acids that are crucial to peptide interaction, specificity, and structural stability of the bound complex when presented on the cell surface. In the MHC class I protein these are termed the A through F pocket (Mage, et al., The peptide-receptive transition state of MHC class I molecules: insight from structure and molecular dynamics. J Immunol. 2012 Aug. 1;189 (3): 1391-9). This binding groove generally accommodates a peptide of eight to ten amino acids (Abualrous, et al., The Carboxy Terminus of the Ligand Peptide Determines the Stability of the MHC Class I Molecule H-2K b: A Combined Molecular Dynamics and Experimental Study. PloS One. 2015 Aug. 13;10 (8): e0135421).

To allow for T cell interaction, it is imperative that MHC class I complexes are stably bound to peptides. This binding causes a structural change in the MHC class I, allowing the complex to reside on the cell surface for hours. Although it has been shown that there is a distinct conformation state of empty class I molecules, this state is energetically unstable due to charge repulsion in the F-pocket (Abualrous, et al., The Carboxy Terminus of the Ligand Peptide Determines the Stability of the MHC Class I Molecule H-2K b: A Combined Molecular Dynamics and Experimental Study. PloS One. 2015 Aug. 13;10 (8): e0135421; Abualrous, et al., F pocket flexibility influences the tapasin dependence of two differentially disease-associated MHC Class I proteins. Eur J Immunol. 2015 April; 45 (4): 1248-57) causing only transient stability and subsequent internalization and recycling (Mage, et al., The peptide-receptive transition state of MHC class I molecules: insight from structure and molecular dynamics. J Immunol. 2012 Aug. 1;189 (3): 1391-9; Saini, et al., Not all empty MHC class I molecules are molten globules: tryptophan fluorescence reveals a two-step mechanism of thermal denaturation. Mol Immunol. 2013 July; 54 (3-4): 386-96). In peptide loaded MHC class I the F-pocket binds the side chain of the carboxyl-terminal residue (C terminus) of the peptide and allows for conformational flexibility with peptide binding (Mage, et al., The peptide-receptive transition state of MHC class I molecules: insight from structure and molecular dynamics. J Immunol. 2012 Aug. 1;189 (3): 1391-9). The A pocket of the MHC complex binds the amino group (N-terminus) while the B pocket binds the side of the second position amino acid in the peptide chain and has been shown to have much less flexibility than the F-pocket. Literature suggests that dipeptides such as glycyl-leucine (GL) can bind the F-pocket of the human and murine MHC class I, namely the human MHC: HLA-A*02:01 and the murine MHC: H-2Kb, stabilizing the peptide receptive state and increasing peptide loading (Saini, et al., Dipeptides promote folding and peptide binding of MHC class I molecules. Proc Natl Acad Sci USA. 2013 Sep. 17;110 (38): 15383-8; Saini, et al., Dipeptides catalyze rapid peptide exchange on MHC class I molecules. Proc Natl Acad Sci USA. 2015 Jan. 6;112 (1): 202-7). This peptide exchange mechanism has been used to generate large libraries of peptide-MHC complexes and to test the affinity of peptides for a specific MHC haplotype (Saini, et al., Dipeptides catalyze rapid peptide exchange on MHC class I molecules. Proc Natl Acad Sci USA. 2015 Jan. 6;112 (1): 202-7; Saini, et al., Empty peptide-receptive MHC class I molecules for efficient detection of antigen-specific T cells. Sci Immunol. 2019 Jul. 19;4 (37): eaau9039). While this function has potential utility in vitro, the major limitation of the use of dipeptides in vivo is that they are rapidly hydrolyzed into single amino acids by cellular enzymes in the gut, blood, and body tissues (Newey & Smyth, The intestinal absorption of some dipeptides. J Physiol. 1959 Jan. 28;145 (1): 48-56; Adibi & Soleimanpour, Functional characterization of dipeptide transport system in human jejunum. J Clin Invest. 1974 May; 53 (5): 1368-74; Adibi, et al., Metabolism of intravenously administered dipeptides in rats: effects on amino acid pools, glucose concentration and insulin and glucagon secretion. Clin Sci Mol Med. 1977 February; 52 2:193-204).

As such there is an unmet need for the identification and development of bioavailable molecules capable of modulating antigen specific immune responses, thereby permitting development of immune-based therapies, and modulation of the immune response.

SUMMARY OF THE INVENTION

The benzofuran compound disclosed herein, (2E)-3-(1-benzofuran-5-yl) prop-2-enoic acid (BzFβ), allowing for a novel use as an immune system modulator and as an adjuvant for a wide array of vaccines, enhancing the in vitro and in vivo presentation of antigen and/or antigen-specific T cell activation. Accordingly, a method is provided for modulating an immune response, by altering the presentation of an antigen-presenting cell. The antigen-presenting cell is altered by contacting the cell with a therapeutically effective amount of (2E)-3-(1-benzofuran-5-yl) prop-2-enoic acid (BzFβ) as a first compound and a therapeutically effective amount of an antigen molecule as second compound. In some variations, the antigen-presenting cell is contacted with the first compound for a first compound incubation period. Optionally, the first compound incubation period is least 15 minutes, or between 1 hour and 24 hours, or any time period therein. Non-limiting examples include 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours. Alternatively, antigen-presenting cell is altered by concurrently contacting the antigen-presenting cell with the first compound and with the second compound for a determined period of time.

The second compound is an antigen molecule. Optional antigen molecules are antigen molecule is a small molecule antigen vaccine, an epitope vaccine, a DNA vaccine, a recombinant DNA vaccine, a messenger RNA vaccine, a subunit vaccine, a recombinant vaccine, a conjugate vaccine, an immunotherapy cancer antigen, or a toxoid vaccine. In some embodiments, the BzFβ contacts the antigen-presenting cell for a first compound incubation period followed by contacting the antigen-presenting cell with the second compound for second compound incubation period after expiration of the first compound incubation period. The second compound incubation period is optionally between 1 hour and 24 hours, or any time period therein. Non-limiting examples include 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours.

The antigen-presenting cell (APC) can be altered in vitro or in vivo. For in vivo alterations of the APC, the first compound is optionally administered to a patient orally, intravenously, or intramuscularly, resulting in the administered first compound contacting the antigen-presenting cell in vivo.

Optionally, the antigen-presenting cell is a dendritic cell. In specific embodiments, the first compound and second compound are contacted to the dendritic cell ex vivo to form a primed dendritic cell, and wherein the method further comprises administering the primed dendritic cell to a patient in need thereof.

A method is further provided herein for enhancing a vaccine through altering the presentation of an antigen-presenting cell by contacting the antigen-presenting cell with a therapeutically effective amount of (2E)-3-(1-benzofuran-5-yl) prop-2-enoic acid (BzFβ) and a therapeutically effective amount of the vaccine, followed by stimulating a lymphocyte by contacting the lymphocyte with the antigen-presenting cell.

Optionally, the antigen-presenting cell is a dendritic cell. The antigen-presenting cell is stimulated by contacting the dendritic cell with the 2E)-3-(1-benzofuran-5-yl) prop-2-enoic acid (BzFβ) for between 1 hour and 24 hours. Non-limiting examples include 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours. In further embodiments, the BzFβ contacts the antigen-presenting cell at between 5 g/mL and 100 g/mL. 5 μg/mL, 7.5 μg/mL, 10 μg/mL, 12.5 μg/mL, 15 μg/mL, 17.5 μg/mL, 20 μg/mL, 22.5 μg/mL, 25 μg/mL, 27.5 μg/mL, 30 μg/mL, 32.5 μg/mL, 35 μg/mL, 37.5 μg/mL, 40 μg/mL, 42.5 μg/mL, 45 μg/mL, 47.5 μg/mL, 50 μg/mL, 52.5 μg/mL, 55 μg/mL, 57.5 μg/mL, 60 μg/mL, 62.5 μg/mL, 65 μg/mL, 67.5 μg/mL, 70 μg/mL, 72.5 μg/mL, 75 μg/mL, 77.5 μg/mL, 80 μg/mL, 82.5 μg/mL, 85 μg/mL, 87.5 μg/mL, 90 μg/mL, 92.5 μg/mL, 95 μg/mL, 97.5 μg/mL, or 100 μg/mL. In alternative embodiments, the BzFβ contacts the antigen-presenting cell at between 25 μM and 540 μM, or any concentration therein. Nonlimiting examples include 25 μM, 27.5 μM, 30 μM, 32.5 μM, 35 μM, 37.5 μM, 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 150 μM, 160 μM, 170 μM, 180 μM, 190 μM, 200 μM, 210 μM, 220 M, 230 μM, 240 μM, 250 M, 260 μM, 270 μM, 280 μM, 290 μM, 300 μM, 325, 350 M, 375 μM, 400 μM, 425 μM, 450 μM, 475 μM, 500 μM, 510 μM, 515 μM, 520 μM, 525 μM, 527.5 μM, 530 μM, 532.5 μM, 535 μM, 537.5 μM, or 540 μM. After contact between the dendritic cells and BzFβ, the antigen-presenting cell is contacted by the vaccine for between 1 hour and 24 hours. Non-limiting examples include 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours. Optionally, the antigen-presenting cell is contacted by the vaccine ex vivo at between 1 ng/ml and 100 g/mL. Non-limiting examples include 1 ng/ml, 2 ng/ml, 5 ng/ml, 10 ng/mL, 15 ng/mL, 20 ng/ml, 25 ng/mL, 50 ng/mL, 100 ng/ml, 125 ng/mL, 150 ng/mL, 175 ng/ml, 200 ng/mL, 225 ng/ml, 250 ng/ml, 275 ng/ml, 300 ng/ml, 350 ng/mL, 400 ng/ml, 450 ng/mL, 500 ng/mL, 550 ng/mL, 600 ng/mL, 650 ng/ml, 700 ng/mL, 750 ng/ml, 800 ng/mL, 850 ng/mL, 900 ng/mL, 950 ng/mL, 1 μg/mL, 2.5 μg/mL, 5 μg/mL, 7.5 μg/mL, 10 μg/mL, 15 μg/mL, 20 μg/mL, 25 μg/mL, 30 μg/mL, 35 μg/mL 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, 0.5 mg/mL, 1 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 92.5 mg/mL, 95 mg/mL, 97.5 mg/mL, 100 mg/mL, 0.25 g/mL, 0.5 g/mL, 1 g/mL, 5 g/mL, 10 g/mL, 15 g/mL, 20 g/mL, 25 g/mL, 30 g/mL, 35 g/mL, 40 g/mL, 45 g/mL, 50 g/mL, 55 g/mL, 60 g/mL, 65 g/mL, 70 g/mL, 75 g/mL, 80 g/mL, 85 g/mL, 90 g/mL, 92.5 g/mL, 95 g/mL, 97.5 g/mL, or 100 g/mL. Alternatively, the antigen-presenting cell is contacted by the vaccine ex vivo at between 0.062 nM and 30 nM, or any concentration therein. Nonlimiting examples include 0.062 nM, 0.065 nM, 0.067 nM, 0.070 nM, 0.075 nM, 0.80 nM, 0.90 nM, 1.0 nM, 1.25 nM, 1.5 nM, 2.0 nM, 2.25 nM, 2.50 nM, 2.75 nM, 3.0 nM, 3.25 nM, 3.50 nM, 3.75 nM, 4.0 nM, 4.25 nM, 4.50 nM, 4.75 nM, 5.0 nM, 5.25 nM, 5.50 nM, 5.75 nM, 7.0 nM, 7.25 nM, 7.50 nM, 7.75 nM, 10.0 nM, 10.25 nM, 10.50 nM, 10.75 nM, 12.0 nM, 12.25 nM, 12.50 nM, 12.75 nM, 15.0 nM, 15.25 nM, 15.50 nM, 15.75 nM, 17.0 nM, 17.25 nM, 17.50 nM, 17.75 nM, 20.0 nM, 20.25 nM, 20.50 nM, 20.75 nM, 22.0 nM, 2.25 nM, 22.50 nM, 22.75 nM, 25.0 nM, 25.25 nM, 25.50 nM, 25.75 nM, 27.0 nM, 27.25 nM, 27.50 nM, 27.75 nM, 28.0 nM, 29 nM, 28.25 nM, 28.5 nM, 28.75 nM, 29.0 nM, 29.25 nM, 29.5 nM, 29.6 nM, 29.7 nM, 29.75 nM, 29.8 nM, 29.9 nM, or 30.0 nM. The vaccine is optionally a small molecule antigen vaccine, an epitope vaccine, a DNA vaccine, a recombinant DNA vaccine, a messenger RNA vaccine, a subunit vaccine, a recombinant vaccine, a conjugate vaccine, an immunotherapy cancer antigen, or a toxoid vaccine.

In specific variations of the invention, the vaccine is a peptide vaccine that contacts the antigen presenting cell at 1 ng/mL to 10 g/mL, or any range thereof as further listed above. Where the vaccine is a DNA, the vaccine contacts the antigen presenting cell at 1 g/mL to 100 g/mL, or any range thereof as further listed above. Where the vaccine is a mRNA, the vaccine contacts the antigen presenting cell at 1 g/mL to 25 g/mL, or any range thereof as further listed above. For whole subunit protein vaccine, the vaccine contacts the antigen presenting cell at 1 g/mL to 20 g/mL, or any range thereof as further listed above.

The antigen-presenting cell (APC) is optionally stimulated by contacting the antigen-presenting cell with BzFβ for between 1 hour and 24 hours. Non-limiting examples include 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours. BzFβ is optionally used at a concentration at the APC at between 5 μg/mL and 100 μg/mL, or optionally at between 50 μg/mL and 100 μg/mL, or at a concentration therein. Nonlimited examples include 5 μg/mL, 7.5 μg/mL, 10 μg/mL, 12.5 μg/mL, 15 μg/mL, 17.5 μg/mL, 20 μg/mL, 22.5 μg/mL, 25 μg/mL, 27.5 μg/mL, 30 μg/mL, 32.5 μg/mL, 35 μg/mL, 37.5 μg/mL, 40 μg/mL, 42.5 μg/mL, 45 μg/mL, 47.5 μg/mL, 50 μg/mL, 52.5 μg/mL, 55 μg/mL, 57.5 μg/mL, 60 μg/mL, 62.5 μg/mL, 65 μg/mL, 67.5 μg/mL, 70 μg/mL, 72.5 μg/mL, 75 μg/mL, 77.5 μg/mL, 80 μg/mL, 82.5 μg/mL, 85 μg/mL, 87.5 μg/mL, 90 μg/mL, 92.5 μg/mL, 95 μg/mL, 97.5 μg/mL, or 100 μg/mL. In other embodiments, BzFß is optionally administered to a patient at between 0.18 mg/kg and 14.2 mg/kg, or any dosage therein. Nonlimiting examples include 0.18 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, 0.50 mg/kg, 0.55 mg/kg, 0.60 mg/kg, 0.75 mg/kg, 0.90 mg/kg, 1.0 mg/kg, 1.25 mg/kg, 1.50 mg/kg, 1.75 mg/kg, 2.0 mg/kg, 2.25 mg/kg, 2.50 mg/kg, 2.75 mg/kg, 3.0 mg/kg, 3.25 mg/kg, 3.50 mg/kg, 3.75 mg/kg, 4.0 mg/kg, 4.25 mg/kg, 4.50 mg/kg, 4.75 mg/kg, 5.0 mg/kg, 5.25 mg/kg, 5.50 mg/kg, 5.75 mg/kg, 6.0 mg/kg, 6.25 mg/kg, 6.50 mg/kg, 6.75 mg/kg, 7.0 mg/kg, 7.25 mg/kg, 7.50 mg/kg, 7.75 mg/kg, 8.0 mg/kg, 8.25 mg/kg, 8.50 mg/kg, 8.75 mg/kg, 9.0 mg/kg, 9.25 mg/kg, 9.50 mg/kg, 9.75 mg/kg, 10.0 mg/kg, 10.25 mg/kg, 10.50 mg/kg, 10.75 mg/kg, 11.0 mg/kg, 11.25 mg/kg, 11.50 mg/kg, 11.75 mg/kg, 12.0 mg/kg, 12.25 mg/kg, 12.50 mg/kg, 12.75 mg/kg, 13.0 mg/kg, 13.25 mg/kg, 2.50 mg/kg, 13.75 mg/kg, 14.0 mg/kg, 14.05 mg/kg, 14.10 mg/kg, 14.15 mg/kg, or 14.2 mg/kg. In other embodiments, the BzFβ is administered orally at between 3.56 mg/kg and 14.24 mg/kg, or any dosage therein. Nonlimiting examples include 3.56 mg/kg, 3.75 mg/kg, 4.0 mg/kg, 4.25 mg/kg, 4.50 mg/kg, 4.75 mg/kg, 5.0 mg/kg, 5.25 mg/kg, 5.50 mg/kg, 5.75 mg/kg, 6.0 mg/kg, 6.25 mg/kg, 6.50 mg/kg, 6.75 mg/kg, 7.0 mg/kg, 7.25 mg/kg, 7.50 mg/kg, 7.75 mg/kg, 8.0 mg/kg, 8.25 mg/kg, 8.50 mg/kg, 8.75 mg/kg, 9.0 mg/kg, 9.25 mg/kg, 9.50 mg/kg, 9.75 mg/kg, 10.0 mg/kg, 10.25 mg/kg, 10.50 mg/kg, 10.75 mg/kg, 11.0 mg/kg, 11.25 mg/kg, 11.50 mg/kg, 11.75 mg/kg, 12.0 mg/kg, 12.25 mg/kg, 12.50 mg/kg, 12.75 mg/kg, 13.0 mg/kg, 13.25 mg/kg, 2.50 mg/kg, 13.75 mg/kg, 14.0 mg/kg, 14.05 mg/kg, 14.10 mg/kg, 14.15 mg/kg, 14.2 mg/kg, or 14.24 mg/kg. Alternatively, BzFß is administered intravenously at between 0.18 mg/kg and 0.5 mg/kg, or any dosage therein. Nonlimiting examples include 0.18 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, or 0.50 mg/kg. In other embodiments, BzFβ is administered intramuscularly at between 0.14 mg/kg and 0.5 mg/kg, or any dosage therein. Nonlimiting examples include 0.14 mg/kg, 0.15 mg/kg, 0.175 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, or 0.50 mg/kg.

After contact with BzFβ, the antigen-presenting cell is optionally, subsequently contacted with the vaccine for between 1 hour and 24 hours. Non-limiting examples include 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours. The vaccine is optionally administered in vivo to a patient at between 0.14 mg/kg and 0.5 mg/kg, or any dosage therein. Nonlimiting examples include 0.14 mg/kg, 0.15 mg/kg, 0.175 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, or 0.50 mg/kg. Alternatively, the vaccine contacts the antigen-presenting cell at between Ing/mL and 100 μg/mL. In specific variations, the vaccine contacts the antigen presenting cell at a range of 1 ng/mL to 10 μg/mL for a peptide vaccine, a range of 1 μg/mL to 100 μg/mL for a DNA vaccine, a range of 1 μg/mL to 25 μg/mL for a mRNA vaccine, or a range of 1 μg/mL to 20 μg/mL for a whole subunit protein vaccine. Non-limiting examples include 1 ng/mL, 2 ng/mL, 5 ng/mL, 10 ng/mL, 15 ng/mL, 20 ng/ml, 25 ng/ml, 50 ng/ml, 100 ng/ml, 125 ng/mL, 150 ng/mL, 175 ng/ml, 200 ng/ml, 225 ng/ml, 250 ng/ml, 275 ng/ml, 300 ng/ml, 325 ng/ml, 350 ng/ml, 375 ng/mL, 400 ng/mL, 425 ng/ml, 450 ng/mL, 475 ng/mL, 500 ng/ml, 525 ng/mL, 550 ng/ml, 575 ng/mL, 600 ng/ml, 625 ng/mL, 650 ng/ml, 675 ng/mL, 700 ng/ml, 725 ng/ml, 750 ng/ml, 775 ng/ml, 800 ng/ml, 825 ng/mL, 850 ng/ml, 875 ng/ml, 900 ng/ml, 925 ng/ml, 950 ng/mL, 950 ng/ml, 1 μg/mL, 2.5 μg/mL, 5 μg/mL, 7.5 μg/mL, 10 μg/mL, 12.5 μg/mL 15 μg/mL, 20 μg/mL, 25 μg/mL, 30 μg/mL, 35 μg/mL 40 μg/mL, 45 μg/mL, 50 μg/mL, 55 μg/mL, 60 μg/mL, 65 μg/mL, 70 μg/mL, 75 μg/mL, 77.5 μg/mL, 80 μg/mL, 82.5 μg/mL, 85 μg/mL, 87.5 μg/mL, 90 μg/mL, 92.5 μg/mL, 95 μg/mL, 97.5 μg/mL, 98 μg/mL, 98.5 μg/mL, 99 μg/mL, 99.5 μg/mL, or 100 μg/mL.

A method is further provided herein for preparing an immunotherapy by obtaining an antigen-presenting cell from a patient, exposing the antigen-presenting cell with a therapeutically effective amount of a first compound and a therapeutically effective amount of a second compound, followed by incubating the antigen-presenting cell with the first compound and the second compound for a at least one hour to form a primed antigen-presenting cell, and then injecting the primed antigen-presenting cell into the patient. The first compound is (2E)-3-(1-benzofuran-5-yl) prop-2-enoic acid (BzFβ). The antigen-presenting cell is contacted with the first compound for a first compound incubation period of at least 15 min. Optionally, the first compound incubation period is between 30 min and 2 h. Nonlimiting examples include 30 min, 35 min, 40 min, 45 min, 50 min, 55 min, 1 h, 65 min, 70 min, 75 min, 80 min, 85 min, 90 min, 95 min, 100 min, 105 min, 110 min, 115 min, or 2 h. In alternative embodiments, the first compound is incubated for from 30 min to 24 h, or any time therein. Nonlimiting examples include30 min, 40 min, 45 min, 50 min, 55 min, 1 h, 75 min, 90 min, 100 min, 115 min, 2 h, 2 h 15 min, 2 h 30 min, 2 h 45 min, 3 h, 3 h 15 min, 3 h 30 min, 3h 45 min, 4 h, 4h 30 min, 5 h, 5 h 30 min, 6 h, 6 h 30 min, 7 h, 7 h 30 min, 8 h, 8 h 30 min, 9 h, 9 h 30 min, 10 h, 10 h 30 min, 11 h, 11 h 30 min, 12 h, 12 h 30 min, 13 h, 13 h 30 min, 14 h, 14 h 30 min, 15 h, 15 h 30 min, 16 h, 16 h 30 min, 17 h, 17 h 30 min, 18 h, 18 h 30 min, 19 h, 19 h 30 min, 20 h, 20 h 30 min, 21 h, 21 h 30 min, 22 h, 22 h 30 min, 23 h, 23 h 5 min, 23 h 10 min, 23 h 15 min, 23 h 20 min, 23 h 25 min, 23 h 30 min, 23 h 35 min, 23 h 40 min, 23 h 45 min, 23 h 50 min, 23 h 55 min, or 24 h. In certain variations, the first compound is exposed to the antigen-presenting cell at between 1.62 μg/mL and 50 μg/mL, or any dosage therein. Alternatively, the first compound is exposed to the antigen-presenting cell at between 3.13 μg/mL and 25 μg/mL, or any dosage therein. Nonlimiting examples of dosages for the first compound include 1.62 μg/mL, 1.70 μg/mL, 1.75 μg/mL, 1.80 μg/mL, 1.90 μg/mL, 2.0 μg/mL, 2.25 μg/mL, 2.50 μg/mL, 2.75 μg/mL, 3.0 μg/mL, 3.25 μg/mL, 3.50 μg/mL, 3.75 μg/mL, 4.0 μg/mL, 4.25 μg/mL, 4.50 μg/mL, 4.75 μg/mL, 5.0 μg/mL, 5.25 μg/mL, 5.50 μg/mL, 6.0 μg/mL, 7.0 μg/mL, 8.0 μg/mL, 9.0 μg/mL, 10.0 μg/mL, 11.0 μg/mL, 12.0 μg/mL, 13.0 μg/mL, 14.0 μg/mL, 15.0 μg/mL, 16.0 g/mL, 17.0 μg/mL, 18.0 μg/mL, 19.0 μg/mL, 20.0 μg/mL, 21.0 μg/mL, 22.0 μg/mL, 22.25 μg/mL, 22.50 μg/mL, 22.75 μg/mL, 23.0 μg/mL, 23.25 μg/mL, 23.50 μg/mL, 23.75 μg/mL, 24.0 μg/mL, 24.25 μg/mL, 24.50 μg/mL, 24.75 μg/mL, or 25.0 μg/mL.

The second compound is an antigen molecule. In some variations, the second compound incubation period is between 1 hour and 24 hours. Non-limiting examples include 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain variations, the second compound is exposed to the antigen-presenting cell at between 1 μg/mL to 0.5 mg/mL, or any dosage therein. Nonlimiting examples of dosages for the second compound is 1.0 μg/mL, 1.25 μg/mL, 1.50 μg/mL, 1.75 μg/mL, 2.0 μg/mL, 2.25 μg/mL, 2.50 μg/mL, 2.75 μg/mL, 3.0 μg/mL, 3.25 μg/mL, 3.50 μg/mL, 3.75 μg/mL, 4.0 μg/mL, 4.25 μg/mL, 4.50 μg/mL, 4.75 μg/mL, 5.0 μg/mL, 5.25 μg/mL, 5.50 μg/mL, 6.0 μg/mL, 7.0 μg/mL, 8.0 μg/mL, 9.0 μg/mL, 10.0 μg/mL, 11.0 μg/mL, 12.0 μg/mL, 13.0 μg/mL, 14.0 μg/mL, 15.0 μg/mL, 20.0 μg/mL, 25 μg/mL, 30 μg/mL, 35 μg/mL, 40 μg/mL, 45 μg/mL, 50 μg/mL, 50 μg/mL, 70 μg/mL, 80 μg/mL, 90 μg/mL, 0.10 mg/mL, 0.12 mg/mL, 0.15 mg/mL, 0.17 mg/mL, 0.20 mg/mL, 0.22 mg/mL, 0.25 mg/mL, 0.27 mg/mL, 0.3 mg/mL, 0.32 mg/mL, 0.35 mg/mL, 0.37 mg/mL, 0.40 mg/mL, 0.42 mg/mL, 0.45 mg/mL 0.47 mg/mL, or 0.50 mg/mL.

A method is further provided herein for loading a desired antigen onto major histocompatibility complex class I molecules of a cell expressing cell surface major histocompatibility complex class I molecules through contacting the cell with an effective amount of a (2E)-3-(1-benzofuran-5-yl) prop-2-enoic acid (BzFβ) for a first period of time and contacting the cell with a second compound for a second period of time, wherein the second compound is the desired antigen.

The cell is optionally contacted with the BzFβ for between 15 minutes and 24 hours. Nonlimiting examples include 15 min, 20 min, 25 min, 30 min, 35 min, 40 min, 45 min, 50 min, 55 min, 1 h, 65 min, 70 min, 75 min, 80 min, 85 min, 90 min, 95 min, 100 min, 105 min, 110 min, 115 min, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In certain embodiments, the BzFβ contacts the antigen-presenting cell ex vivo or in vitro at between 5.0 g/mL and 100 μg/mL. Nonlimiting examples include 5.0 μg/mL, 5.25 μg/mL, 5.50 μg/mL, 6.0 μg/mL, 7.0 μg/mL, 8.0 μg/mL, 9.0 μg/mL, 10.0 μg/mL, 11.0 μg/mL, 12.0 μg/mL, 13.0 μg/mL, 14.0 μg/mL, 15.0 μg/mL, 20.0 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, or 100 μg/mL. In certain embodiments, the BzFβ is administered in vivo at between 0.18 mg/kg and 14.2 mg/kg, or any dosage therein. Nonlimiting examples include 0.18 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, 0.50 mg/kg, 0.55 mg/kg, 0.60 mg/kg, 0.75 mg/kg, 0.90 mg/kg, 1.0 mg/kg, 1.25 mg/kg, 1.50 mg/kg, 1.75 mg/kg, 2.0 mg/kg, 2.25 mg/kg, 2.50 mg/kg, 2.75 mg/kg, 3.0 mg/kg, 3.25 mg/kg, 3.50 mg/kg, 3.75 mg/kg, 4.0 mg/kg, 4.25 mg/kg, 4.50 mg/kg, 4.75 mg/kg, 5.0 mg/kg, 5.25 mg/kg, 5.50 mg/kg, 5.75 mg/kg, 6.0 mg/kg, 6.25 mg/kg, 6.50 mg/kg, 6.75 mg/kg, 7.0 mg/kg, 7.25 mg/kg, 7.50 mg/kg, 7.75 mg/kg, 8.0 mg/kg, 8.25 mg/kg, 8.50 mg/kg, 8.75 mg/kg, 9.0 mg/kg, 9.25 mg/kg, 9.50 mg/kg, 9.75 mg/kg, 10.0 mg/kg, 10.25 mg/kg, 10.50 mg/kg, 10.75 mg/kg, 11.0 mg/kg, 11.25 mg/kg, 11.50 mg/kg, 11.75 mg/kg, 12.0 mg/kg, 12.25 mg/kg, 12.50 mg/kg, 12.75 mg/kg, 13.0 mg/kg, 13.25 mg/kg, 2.50 mg/kg, 13.75 mg/kg, 14.0 mg/kg, 14.05 mg/kg, 14.10 mg/kg, 14.15 mg/kg, or 14.2 mg/kg. In other embodiments, the BzFβ is administered orally at between 3.56 mg/kg and 14.24 mg/kg, or any dosage therein. Nonlimiting examples include 3.56 mg/kg, 3.75 mg/kg, 4.0 mg/kg, 4.25 mg/kg, 4.50 mg/kg, 4.75 mg/kg, 5.0 mg/kg, 5.25 mg/kg, 5.50 mg/kg, 5.75 mg/kg, 6.0 mg/kg, 6.25 mg/kg, 6.50 mg/kg, 6.75 mg/kg, 7.0 mg/kg, 7.25 mg/kg, 7.50 mg/kg, 7.75 mg/kg, 8.0 mg/kg, 8.25 mg/kg, 8.50 mg/kg, 8.75 mg/kg, 9.0 mg/kg, 9.25 mg/kg, 9.50 mg/kg, 9.75 mg/kg, 10.0 mg/kg, 10.25 mg/kg, 10.50 mg/kg, 10.75 mg/kg, 11.0 mg/kg, 11.25 mg/kg, 11.50 mg/kg, 11.75 mg/kg, 12.0 mg/kg, 12.25 mg/kg, 12.50 mg/kg, 12.75 mg/kg, 13.0 mg/kg, 13.25 mg/kg, 2.50 mg/kg, 13.75 mg/kg, 14.0 mg/kg, 14.05 mg/kg, 14.10 mg/kg, 14.15 mg/kg, 14.2 mg/kg, or 14.24 mg/kg. Alternatively, BzFβ is administered intravenously at between 0.18 mg/kg and 0.5 mg/kg, or any dosage therein. Nonlimiting examples include 0.18 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, or 0.50 mg/kg. In other embodiments, BzFβ is administered intramuscularly at between 0.14 mg/kg and 0.5 mg/kg, or any dosage therein. Nonlimiting examples include 0.14 mg/kg, 0.15 mg/kg, 0.175 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, or 0.50 mg/kg.

The cell is optionally contacted with the antigen ex vivo or in vitro with between 1 ng/ml and 100 μg/mL, or any concentration therein, of the desired antigen. Nonlimiting examples include 1 ng/ml, 2 ng/ml, 5 ng/ml, 10 ng/mL, 15 ng/ml, 20 ng/ml, 25 ng/mL, 50 ng/mL, 100 ng/mL, 125 ng/mL, 150 ng/ml, 175 ng/mL, 200 ng/ml, 225 ng/mL, 250 ng/ml, 275 ng/ml, 300 ng/ml, 325 ng/ml, 350 ng/ml, 375 ng/ml, 400 ng/mL, 425 ng/mL, 450 ng/mL, 475 ng/mL, 500 ng/ml, 525 ng/ml, 550 ng/mL, 575 ng/mL, 600 ng/ml, 625 ng/ml, 650 ng/ml, 675 ng/ml, 700 ng/ml, 725 ng/ml, 750 ng/mL, 775 ng/ml, 800 ng/mL, 825 ng/ml, 850 ng/ml, 875 ng/mL, 900 ng/ml, 925 ng/ml, 950 ng/ml, 950 ng/ml, 1 μg/mL, 2.5 μg/mL, 5 μg/mL, 7.5 μg/mL, 10 μg/mL, 12.5 μg/mL 15 μg/mL, 20 μg/mL, 25 μg/mL, 30 μg/mL, 35 μg/mL 40 μg/mL, 45 μg/mL, 50 μg/mL, 55 μg/mL, 60 μg/mL, 65 μg/mL, 70 μg/mL, 75 μg/mL, 77.5 μg/mL, 80 μg/mL, 82.5 μg/mL, 85 μg/mL, 87.5 μg/mL, 90 μg/mL, 92.5 μg/mL, 95 μg/mL, 97.5 μg/mL, 98 μg/mL, 98.5 μg/mL, 99 μg/mL, 99.5 μg/mL, or 100 μg/mL. In specific variations, the desired antigen is 8 amino acid residues long or 9 amino acid residues long. In certain variations, the desired antigen is administered in vivo at between 0.14 mg/kg and 0.5 mg/kg, or any dosage therein. Nonlimiting examples include 0.14 mg/kg, 0.15 mg/kg, 0.175 mg/kg, 0.20 mg/kg, 0.225 mg/kg, 0.25 mg/kg, 0.275 mg/kg, 0.30 mg/kg, 0.35 mg/kg, 0.40 mg/kg, 0.45 mg/kg, or 0.50 mg/kg.

A method is further provided herein for preparing an in vivo immunotherapy. The cell populations of dendritic cells and CD8+ t-cells in a patient in need of tumor treatment are first tested to identify the number of each cell population, and confirming the population numbers meet or exceed a minimum threshold value. The minimum threshold value of white blood cell count (including T cells and DC) is adequate to response to generate the in vivo immune response.

Dendritic cells account for around 0.9% of peripheral blood mononuclear cells (PBMCs). (Fearnley, et al., Monitoring human blood dendritic cell numbers in normal individuals and in stem cell transplantation. Blood. 1999 Jan. 15; 93 (2): 728-36). In healthy adults, the PBMCs are around 30-60×$10^9$ cells/L. (Lin, et al., The peripheral blood mononuclear cell count is associated with bone health in elderly men. Medicine (Balt). 2016 April; 95 (15): e3357). Dendritic cell population is 15×$10^6$ dendritic cells (DCs) per liter of blood for an adult. (See, Sabado & Bhardwai, Directing dendritic cell immunotherapy towards successful cancer treatment. Immunotherapy. 2020 Jan. 1; 2 (1): 37-56). However, studies suggest around 85 DC are required to initiate an immune response. (Celli, et al., How many dendritic cells are required to initiate a t-cell response? Blood. 2012 Nov. 8; 120 (19): 3945-8). In some embodiments, the minimum threshold value of the CD8+ t-cell population is 1.0×$10^2$ cells/L. Typical numbers of CD8+ t-cells in healthy individuals are between 50×$10^7$ and 15×$10^8$ cells per liter of blood for an adult. (See, Uppal, et al., Normal values of CD4 and CD8 lymphocyte subsets in healthy Indian adults and the effects of sex, age, ethnicity, and smoking. Cytometry B Clin Cytom. 2003 March; 52 (1): 32-6). Minimum numbers of t-cells required for immune responses are around 20×$10^7$ cells per liter of blood, with around 62.6×$10^6$ cells per liter of blood of CD8+ t-cells.

If the cell populations meet the minimum threshold, a therapeutically effective amount of an antitumor therapy is administered to the patient in need of tumor treatment. The antitumor therapy is optionally chemotherapy, radiation, immunotherapy, hyperthermia, or photodynamic therapy. The antitumor therapy is selected to result in tumor cell death, thereby releasing cell debris that is picked up and processed by the patient's endogenous DCs. The patient is also administered a therapeutically effective amount of a first compound to the patient in need of tumor treatment orally, intravenously, intra-arterially, intrathecally, or intraventricularly, where the first compound is (2E)-3-(1-benzofuran-5-yl) prop-2-enoic acid. The (2E)-3-(1-benzofuran-5-yl) prop-2-enoic acid is administered as outlined herein, causing the DC cells to load tumor antigens for presentation to CD8+ t-cells. In specific variations, the BzFβ is administered concurrently.

BRIEF DESCRIPTION OF THE DRAWINGS

For a fuller understanding of the invention, reference should be made to the following detailed description, taken in connection with the accompanying drawings, in which.

D1.16) shows that BzFβ is able to enhance binding of the peptide within 1 h (p<0.001). Data shown is the mean of n>3 experiments analyzed using a two-tailed t-test compared to control, NS P>0.05, * P<0.05,  P<0.01, * P<0.001. Error bars represent the standard deviation.

Figure 5:
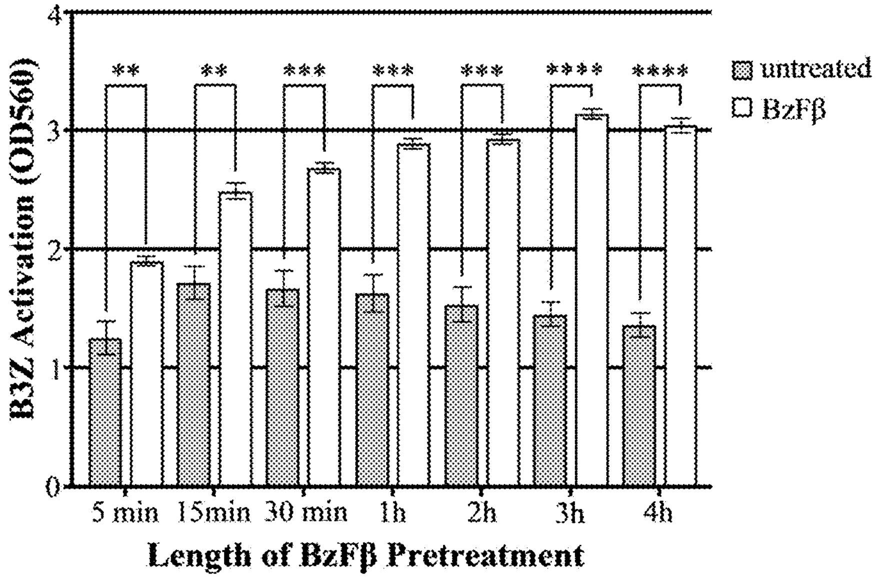

FIG. 5 is a graph showing BzFβ significantly enhances the ability of peptide pulsed DC2.4 to activate the CD8+ T cell hybridoma, B3Z. BzFβ was found to significantly enhance peptide pulsed DC2.4 activation of B3Z cells as rapidly as 5 min (p<0.01). Data shown is the mean of n>3 experiments analyzed using a two-tailed t-test compared to control, NS P>0.05, * P<0.05,  P<0.01, * P<0.001, **** P<0.0001. Error bars represent the standard deviation.

Figure 6:
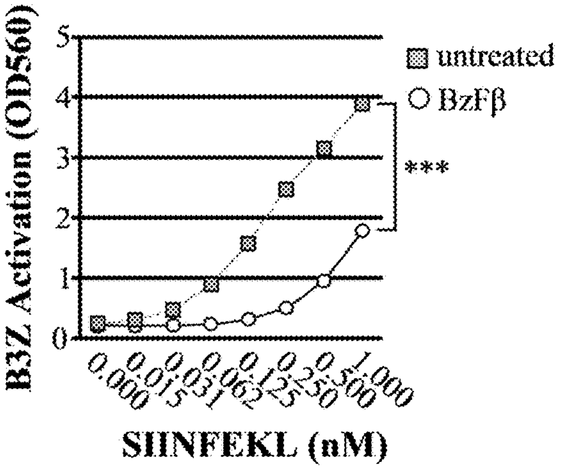

FIG. 6 is a graph showing BzFβ significantly enhances the ability of peptide pulsed DC2.4 to activate the CD8+ T cell hybridoma, B3Z.Co-treatment of DC2.4 with 25 μg/mL BzFβ plus 2-fold serial dilutions of SIINFEKL (starting at 1 nM) for 1 h, activated the B3Z cells to a significantly greater extent than did DC2.4 treated with only the peptide (p<0.0001, error bars shown but not visible). Data shown is the mean of n≥3 experiments analyzed using a two-tailed t-test compared to control, NS P>0.05, * P<0.05,  P<0.01, * P<0.001. Error bars represent the standard deviation. Open circles (untreated), grey squares (BzFβ treated).

Figure 7:
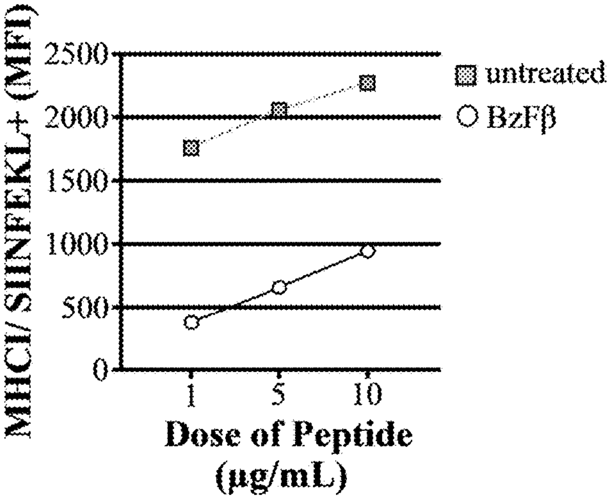

FIG. 7 is a graph showing BzFβ significantly enhances the high dose peptide binding to DC2.4 as detected by antibody (25-D1.16). (p<0.0001), error bars shown but not visible). Open circles (untreated), grey squares (BzFβ treated).

Figure 8:
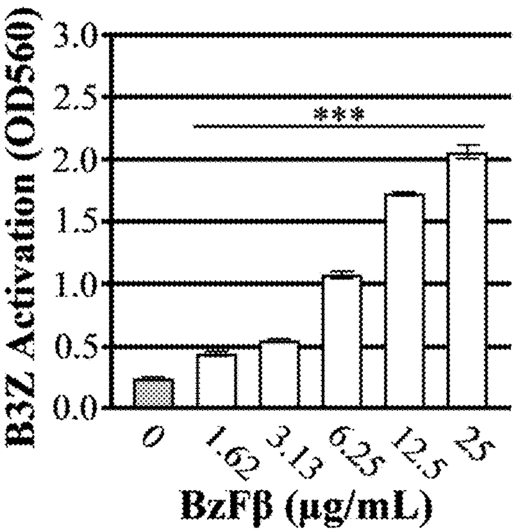

FIG. 8 is a graph showing the effects of BzFβ on cross-presentation of an exogenous protein. DC2.4 cells co-treated for 6 h with increasing concentrations of BzFβ in the presence of 0.5 mg/mL OVA were able to significantly activate B3Z (p<0.001 for all doses tested). Data shown as mean of n≥3 experiments analyzed using a two-tailed t-test compared to control, NS P>0.05, * P<0.05,  P<0.01, * P<0.001. Error bars represent the standard deviation.

Figure 9:
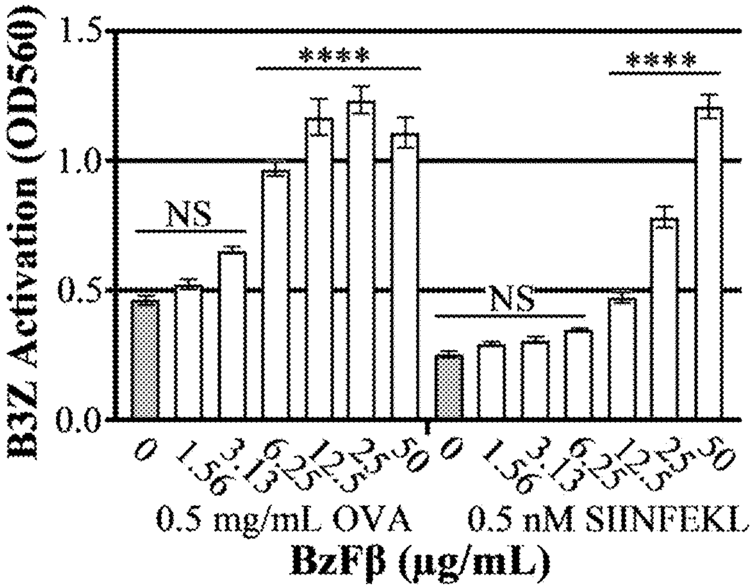

FIG. 9 is a graph showing the effects of BzFβ on cross-presentation of an exogenous protein. Co-treatment of freshly isolated murine splenocytes with concentrations of BzFβ>3.13 μg/mL in the presence of 0.5 mg/mL OVA were able to significantly enhance activation of B3Z (p<0.0001). Treatment of the splenocytes overnight with BzFβ and then a 1 h pulse with 0.5 nM SIINFEKL also enhanced B3Z activation. Data shown as mean of n≥3 experiments analyzed using a two-tailed t-test compared to control, NS P>0.05, * P<0.05,  P<0.01, * P<0.001, **** P<0.0001. Error bars represent the standard deviation.

Figure 10:
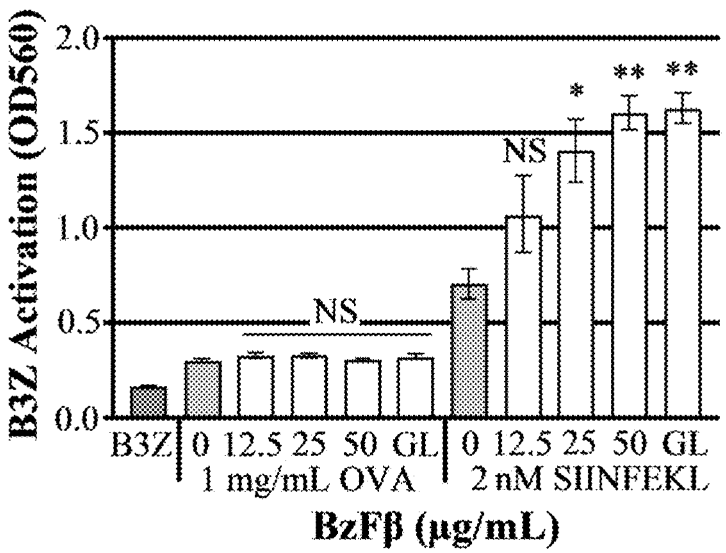

FIG. 10 is a graph showing the effects of BzFβ on cross-presentation of an exogenous protein. B16F10 cells demonstrated a significant BzFβ dose dependent increase in the ability to activate the B3Z response when they were pulsed with 2 nM SIINFEKL (25 μg P=0.0190, 50 μg P=0.0017), but not when they were co-treated with BzFß and 1 mg/mL OVA. A response similar to that generated by BzFβ was obtained from B16F10 cells treated with 10 mM (1.88 mg/mL) of the dipeptide, GL (p=0.0013). Data shown as mean of n≥3 experiments analyzed using a two-tailed t-test compared to control, NS P>0.05, * P<0.05,  P<0.01, * P<0.001. Error bars represent the standard deviation.

Figure 11:
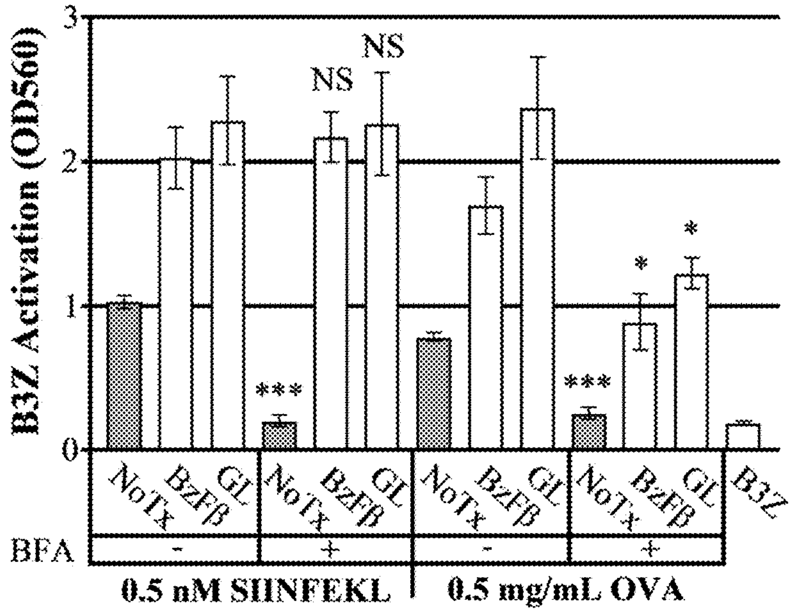

FIG. 11 is a graph showing the effects of BzFβ on cross-presentation of an exogenous protein. Treatment of DC2.4 with BFA along with either BzFβ or GL for 6 hrs affected B3Z activation by OVA, but not by the SIINFEKL peptide. The significance was calculated against the response of the cells in each treatment group that did not receive BFA. OVA associated activation was significantly inhibited by BFA treatment (vehicle p<0.001, BzFβ p=0.0442, GL p=0.0358). Data shown as mean of n≥3 experiments analyzed using a two-tailed t-test compared to control, NS P>0.05, * P<0.05,  P<0.01, * P<0.001. Error bars represent the standard deviation.

Figure 12A:
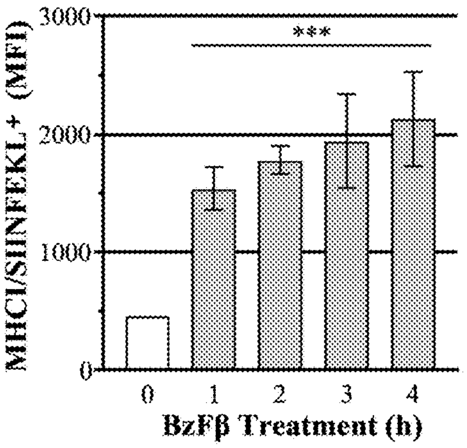

FIG. 12A is a graph showing BzFβ time-dependently affects the overall surface expression of SIINFEKL-bound MHC class I. DC2.4 cells were treated for up to 4 h with 25 μg/mL BzFβ and then pulsed for 1 h with 0.5 nM SIINFEKL. These cells were then stained with the PE-label clone 25-D1.16 antibody specific for the MHC class I/SIINFEKL complex. Examination of the DC2.4 and IMG cells by flow cytometry revealed a significant enhancement (p<0.001 and 0.0001, respectively) of MHC class I/SIINFEKL complexes that increased over time. Data shown as mean of n≥3 experiments shown and analyzed using a two-tailed t-test, NS P>0.05, * P<0.05,  P<0.01, * P<0.001. Error bars represent the standard deviation.

Figure 12B:
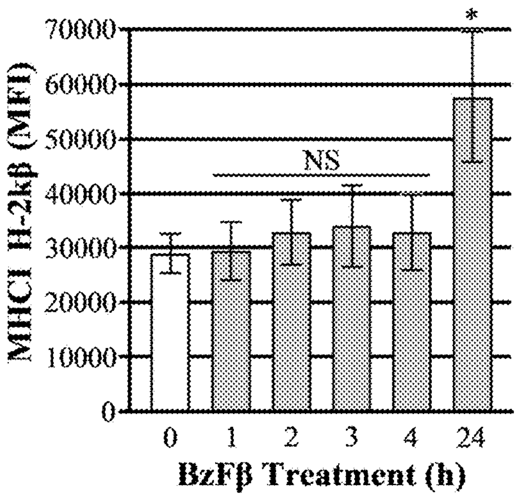

FIG. 12B is a graph showing BzFβ does not affect the overall surface expression of MHC class I. When identically treated DC2.4 cells, as outlined in FIG. 12A, were stained with the MHC class I H-2Kb specific antibody (AF6-88.5.5.3), no effect on the abundance of MHC class I was observed except at the 24 h time point. Data shown as mean of n≥3 experiments shown and analyzed using a two-tailed t-test, NS P>0.05, * P<0.05,  P<0.01, * P<0.001. Error bars represent the standard deviation.

Figure 13A:
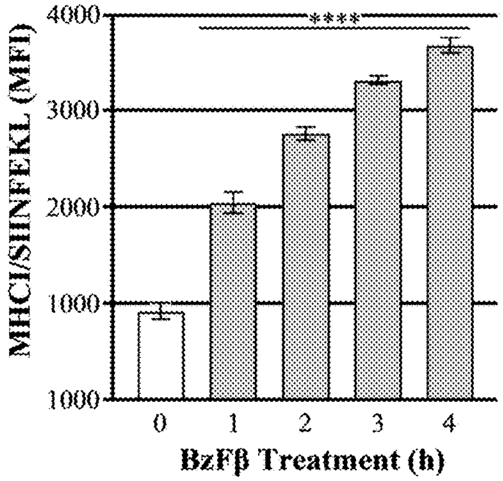

FIG. 13A is a graph showing BzFβ dose-dependently affects the overall surface expression of SIINFEKL-bound MHC class I on IMG cells. IMG cells were treated for up to 4 h with 25 μg/mL BzFβ and then pulsed for 1 h with 0.5 nM SIINFEKL. These cells were then stained with the PE-label clone 25-D1.16 antibody specific for the MHC class I/SIINFEKL complex. Examination of the DC2.4 and IMG cells by flow cytometry revealed a significant enhancement (p<0.001 and 0.0001, respectively) of MHC class I/SIINFEKL complexes that increased over time. Data shown as mean of n≥3 experiments shown and analyzed using a two-tailed t-test, NS P>0.05, * P<0.05,  P<0.01, * P<0.001. Error bars represent the standard deviation.

Figure 13B:
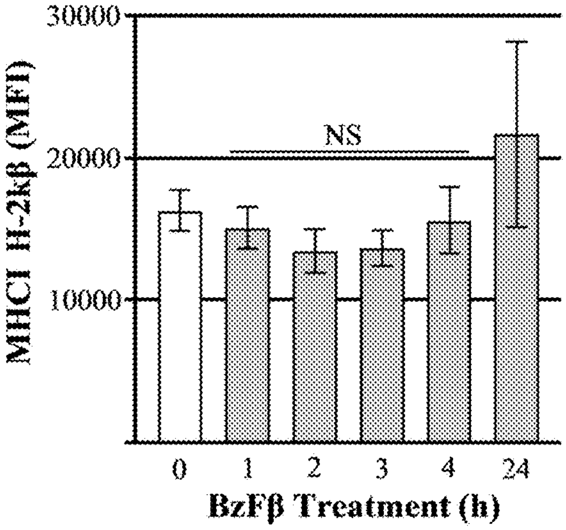

FIG. 13B is a graph showing BzFβ does not affect the overall surface expression of MHC class I on IMG cells. When identically treated IMG cells were stained with the MHC class I H-2Kb specific antibody (AF6-88.5.5.3), no effect on the abundance of MHC class I was observed except at the 24 h time point. Data shown as mean of n≥3 experiments shown and analyzed using a two-tailed t-test, NS P>0.05, * P<0.05, ** P<0.01, * P<0.001. Error bars represent the standard deviation.

Figure 14:
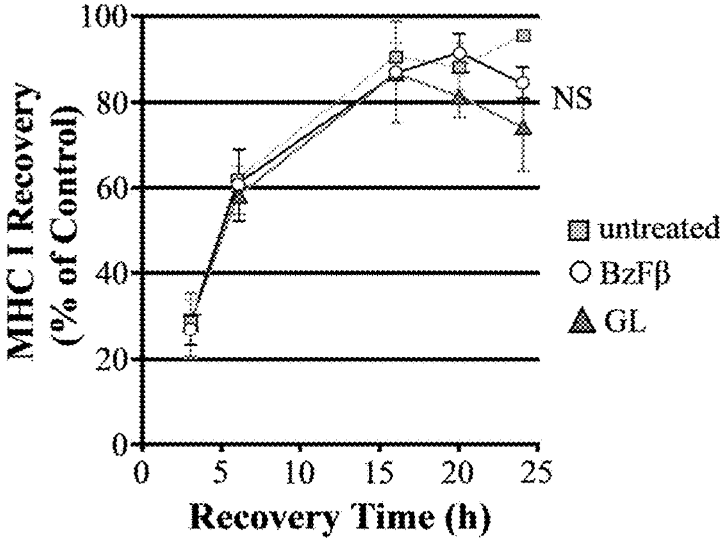

FIG. 14 is a graph showing the effect of BzFβ is not due to modulation of MHC class I expression. Acid-stripped DC2.4 were treated with BzFβ or GL during recovery and showed no increase in MHC class I production. Data shown as mean of n≥3 experiments shown and analyzed using a two-tailed t-test, for curves variance was measured through area under the curve, NS P>0.05, * P<0.05,  P<0.01, * P<0.001, **** P<0.0001. Error bars represent the standard deviation. Legend (grey squares=no treatment control; open circle=BzFβ; triangle=GL).

Figure 15:
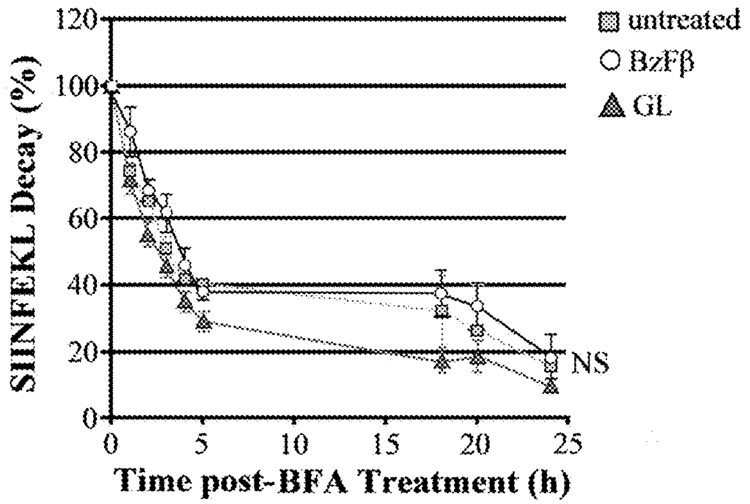

FIG. 15 is a graph showing the effect of BzFβ is not due to modulation of MHC class I expression. BFA treatment of DC2.4 following a 24 h exposure to BzFß or GL and then a 1 h pulse with 30 nM SIINFEKL showed no increase in overall stability when compared to the untreated controls at t-0 decay. Legend (black squares=no treatment control; triangle=BzFβ; triangle=GL). Data shown as mean of n≥3 experiments shown and analyzed using a two-tailed t-test, for curves variance was measured through area under the curve, NS P>0.05, * P<0.05,  P<0.01, * P<0.001, **** P<0.0001. Error bars represent the standard deviation.

Figure 16:
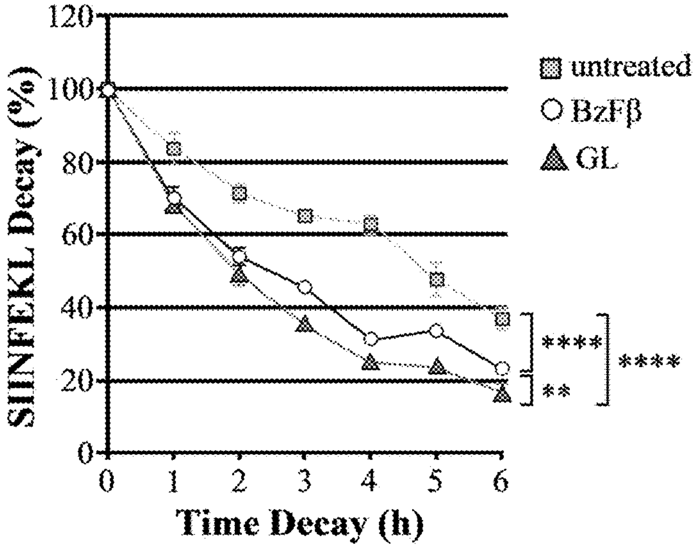

FIG. 16 is a graph showing BzFβ is able to displace peptide from surface MHC class I. The addition of 25 μg/mL (132.2 μM) BzFβ to DC2.4 cells after a 1 h pulse with 30 nM SIINFEKL revealed that BzFβ was able to significantly increase the rate of peptide turnover as compared to the untreated controls (p<0.0001). Data shown as mean of n≥3 experiments shown and analyzed using a two-tailed t-test, for curves variance was measured through area under the curve, NS P>0.05, * P<0.05,  P<0.01, * P<0.001, **** P<0.0001. Error bars represent the standard deviation. Legend (black squares=no treatment control; triangle=BzFβ; triangle=GL).

Figure 17A:
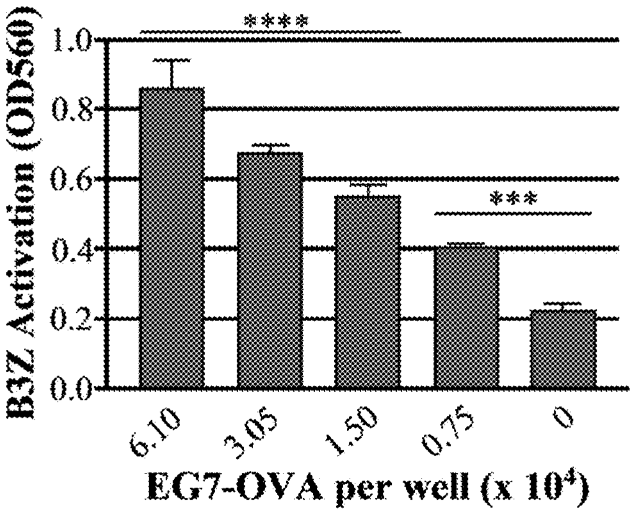

FIG. 17A is a graph showing that E.G7-OVA's endogenously produced SIINFEKL can activate B3Z cells. E.G7-OVA produces OVA endogenously and via processing is able to display the SIINFEKL peptide bound on its surface MHC class I H-2Kb. The resulting MHC class I/SIINFEKL complex can be presented to and activate B3Z cells. Coculture of 2-fold dilutions of E.G7-OVA cells with B3Z reveal the ability of E.G7-OVA to dose-dependently activate B3Z. Data shown as mean of n>3 experiments shown and analyzed using a two-tailed t-test, for curves variance was measured through area under the curve, NS P>0.05, * P<0.05,  P<0.01, * P<0.001, **** P<0.0001. Error bars represent the standard deviation.

Figure 17B:
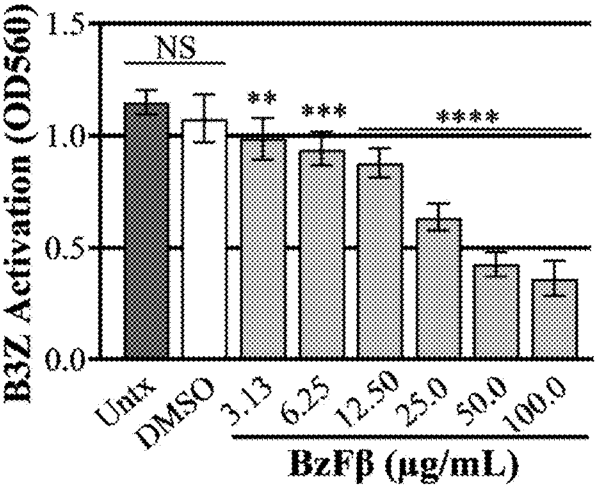

FIG. 17B is a graph showing BzFβ is able to displace peptide from surface MHC class I. Treatment of E.G7-OVA cells with increasing concentrations of BzFβ resulted in a dose-dependent reduction of surface MHCI/SIINFEKL complexes as detected in the B3Z assay. This apparent displacement of SIINFEKL from the surface of E.G7-OVA was significant at all doses tested. The percent of SIINFEKL decay is based on 100% of bound peptide at t=0. Data shown as mean of n≥3 experiments shown and analyzed using a two-tailed t-test, for curves variance was measured through area under the curve, NS P>0.05, * P<0.05,  P<0.01, * P<0.001, **** P<0.0001. Error bars represent the standard deviation.

Figure 18:
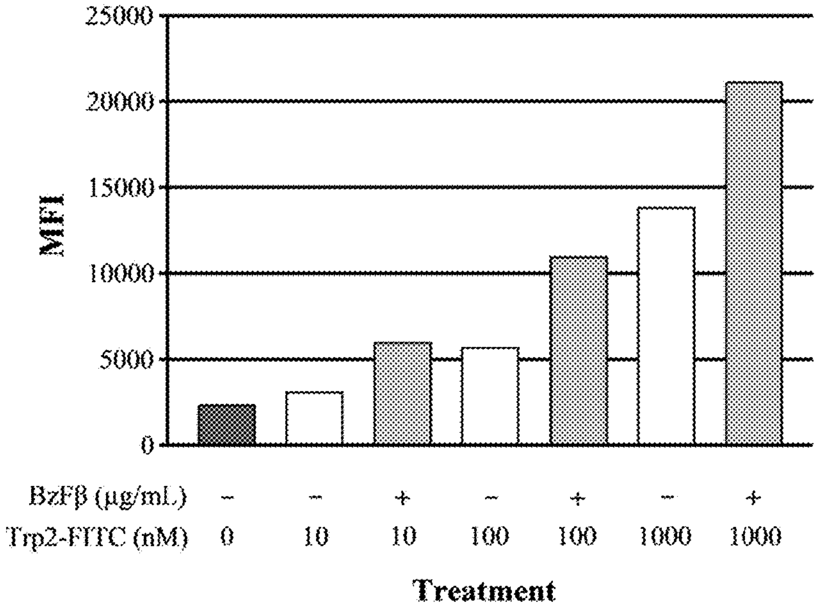

FIG. 18 is a graph showing BzFβ facilitates binding of peptides toTrp2 H-2Kb. Pretreatment of DC2.4 with 50 μg/mL BzFβ for 1 h, followed by a 1 h pulse with 0, 10, 100, or 1000 nM FITC-labeled melanoma Trp2 H-2Kb peptide, revealed enhancement of the direct binding of an H-2Kb peptide to DC2.4 cells.

Figure 19:
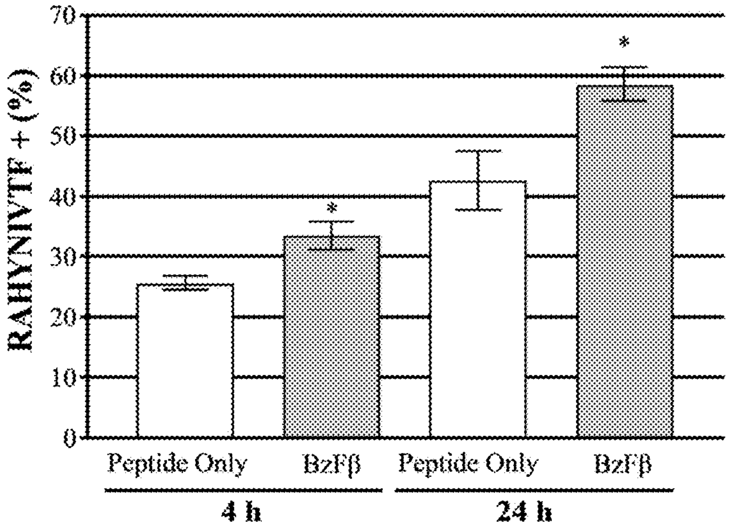

FIG. 19 is a graph showing BzFβ facilitates binding of a peptide to Trp2 H-2 Db. Treatment of DC2.4 with 25 μg/mL BzFβ for 4 or 24 h prior to a 1 h pulse with the H-2 Db N-terminal FITC-labeled HPV peptide, RAHYNIVTF, produced a significant increase in peptide binding (p=0.0250 and p=0.0339 respectively). Data shown as mean of n>3 experiments shown and analyzed using a two-tailed t-test, for curves variance was measured through area under the curve, * P<0.05. Error bars represent the standard deviation.

Figure 20A:
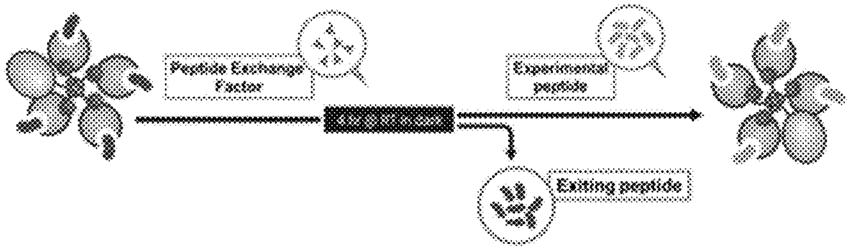

FIG. 20A is a cartoon showing the peptide exchange assay. The design of the QuickSwitch assay is shown. Image from the user manual supplied by MBL International (MBL Int'l Corp., Woburn, MA).

Figure 20B:
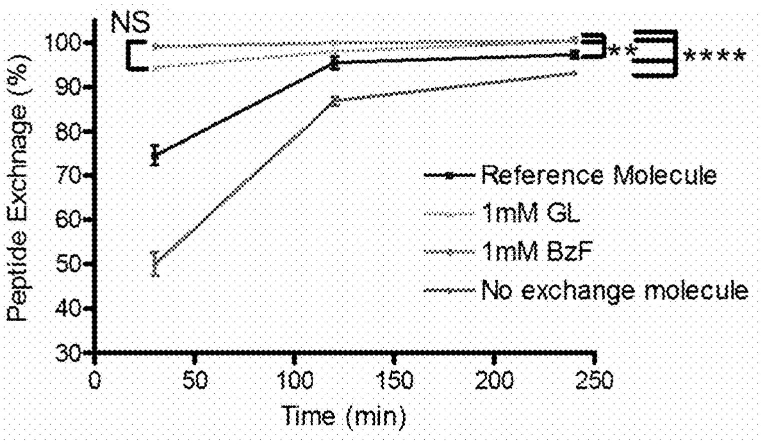

FIG. 20B is a graph showing the peptide exchange assay. BzFβ is significantly better at displacing a pre-bound peptide from the binding groove than when the reaction is performed without an exchange factor (p<0.001) or with the provided exchange molecule (p=0.0013) on H-2$K^b$ QuickSwitch.

Figure 20C:
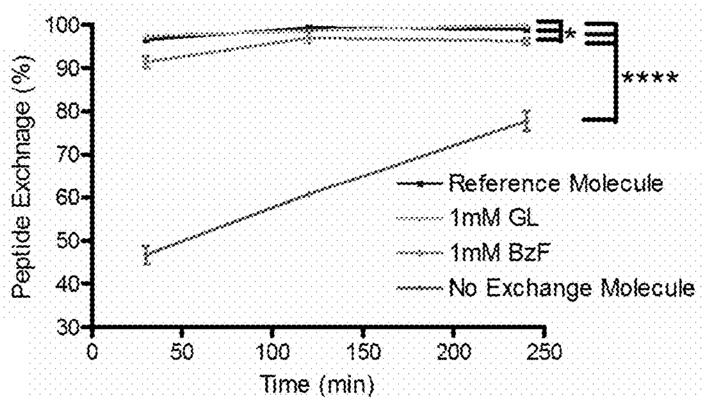

FIG. 20C is a graph showing the peptide exchange assay, demonstrating the ability of BzFβ to rapidly facilitate peptide exchange on HLA-A*02:01. This response was found to be highly significant (p<0.001).

Figure 21A:

FIG. 21A is an image showing molecular docking predicts that BzFβ's ability to function as a peptide exchange factor is associated with binding within the F pocket of MHC H-2$K^b$. Molecular docking was performed using AutoDock and the structure coordinates of H-2$K^b$ (PDB id: 39PL). BzFβ was predicted to bind within the F pocket of H-2$K^b$ by forming hydrogen bonds with Thr80 and Lys146. BzFβ is shown within the F pocket of class I molecules and forming hydrogen bonds with key amino acids that regulate peptide binding within the pocket.

Figure 21B:
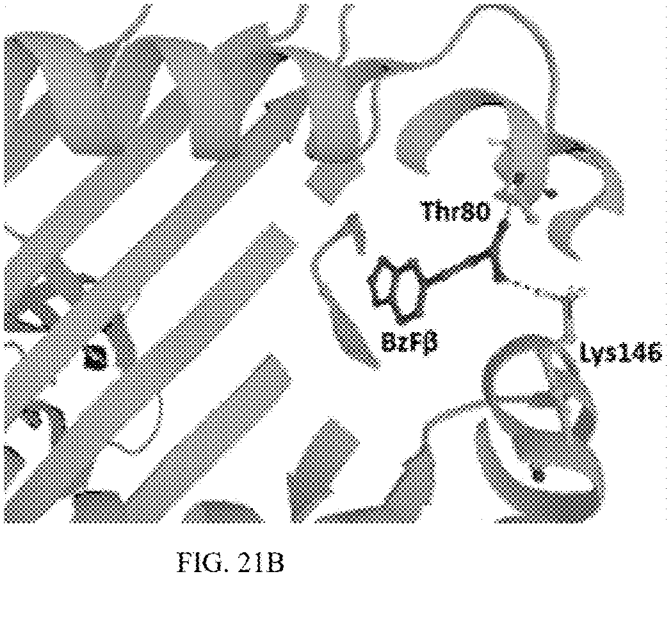

FIG. 21B is an image showing molecular docking predicts that BzFβ's ability to function as a peptide exchange factor is associated with binding within the F pocket of MHC H-2$K^b$. Molecular docking was performed using AutoDock and the structure coordinates of H-2$K^b$ (PDB id: 39PL). BzFβ was predicted to bind within the F pocket of H-2$K^b$ by forming hydrogen bonds with Thr80 and Lys146. BzFβ is shown within the F pocket of class I molecules and forming hydrogen bonds with key amino acids that regulate peptide binding within the pocket.

Figure 22A:
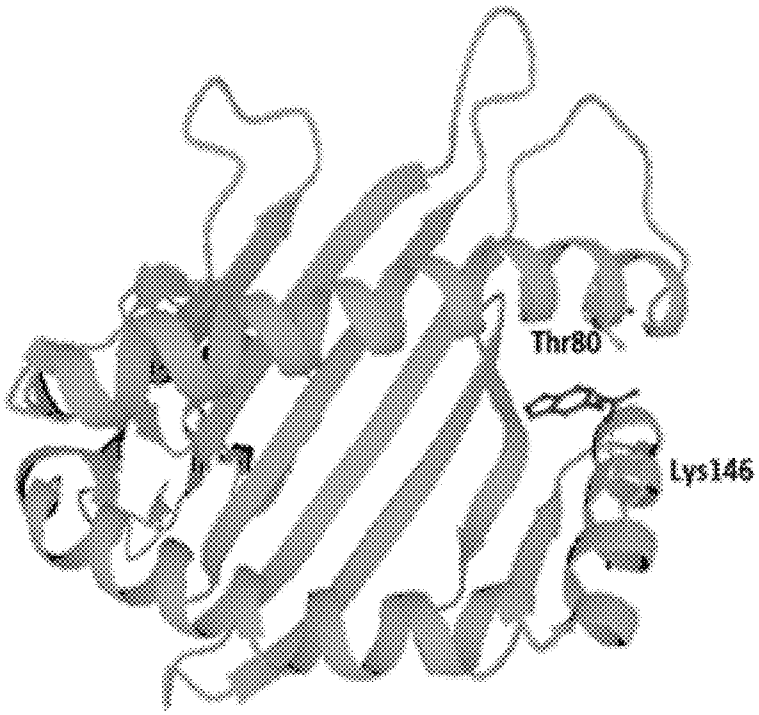

FIG. 22A is an image showing molecular docking predicts that BzFβ's ability to function as a peptide exchange factor is associated with binding within the F pocket of HLA-A*02:01. Molecular docking was performed using AutoDock and the structure coordinates of HLA-A*02:01 (PDB id: 3HLA). BzFβ was predicted to bind within the F pocket of HLA-A*02:01 by forming hydrogen bonds with just Lys146. BzFβ is shown within the F pocket of class I molecules and forming hydrogen bonds with key amino acids that regulate peptide binding within the pocket.

Figure 22B:
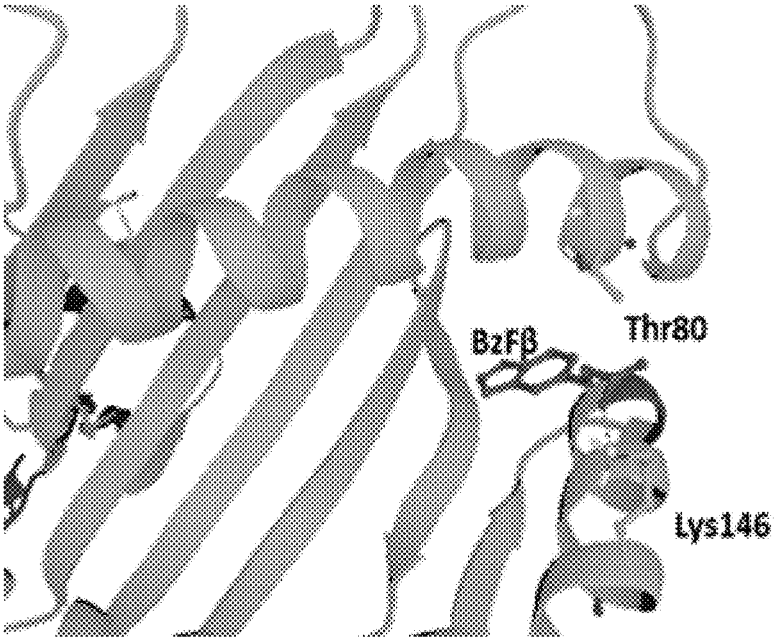

FIG. 22B is an image showing molecular docking predicts that BzFβ's ability to function as a peptide exchange factor is associated with binding within the F pocket of HLA-A*02:01. Molecular docking was performed using AutoDock and the structure coordinates of HLA-A*02:01 (PDB id: 3HLA). BzFβ was predicted to bind within the F pocket of HLA-A*02:01 by forming hydrogen bonds with just Lys146. BzFß is shown within the F pocket of class I molecules and forming hydrogen bonds with key amino acids that regulate peptide binding within the pocket.

Figure 23:
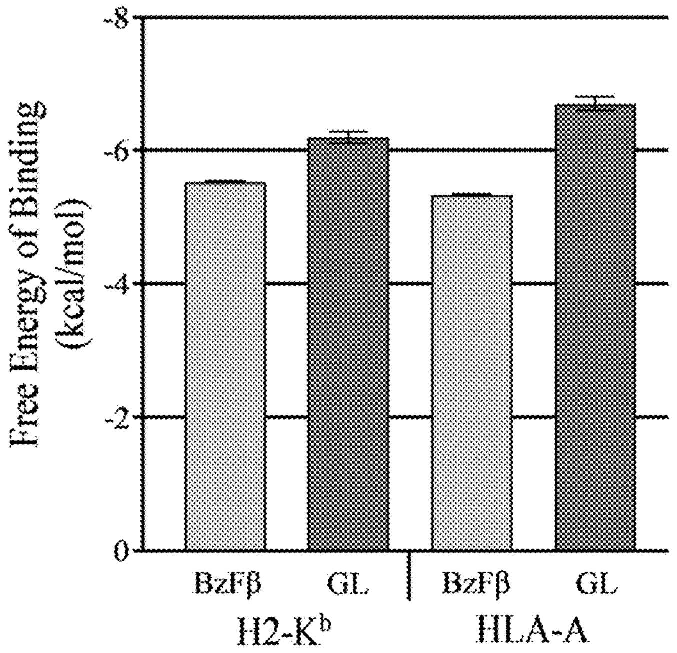

FIG. 23 is an image showing molecular docking predicts that BzFβ's ability to function as a peptide exchange factor is associated with binding within the F pocket of MHC H-2$K^b$ and HLA-A*02:01. Molecular docking was performed using AutoDock and the structure coordinates of H-2$K^b$ (PDB id: 3P9L) and HLA-A*02:01 (PDB id: 3HLA). BzFβ was predicted to bind within the F pocket of both class I molecules, H-2$K^b$ and HLA-A*02:01, by forming hydrogen bonds with key amino acids that regulate peptide binding within the pocket. The predicted average free energy of binding (kcal/mol) for the top 3 poses of BzFβ and GL for docking with H-2$K^b$ and HLA-A*02:01 is shown. Error bars represent the standard deviation derived from the top 3 poses.

Figure 24A:
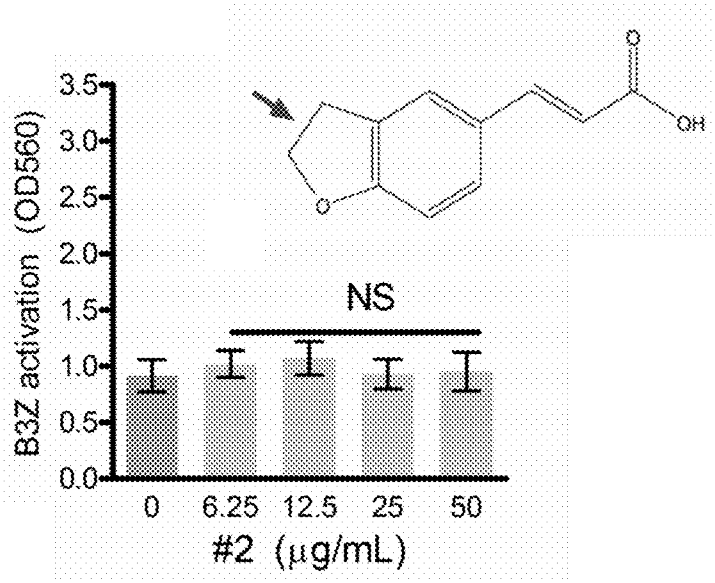

FIG. 24A is a graph with inset line drawing showing BzFβ's unique structure is integral for the enhancement of T cell response. DC2.4 cells treated with molecule #2, that is structurally similar to BzFβ, failed to evoke activation of the B3Z response. Red arrows denote structural variance from BzFβ. Data shown as mean of n≥3 experiments shown and analyzed using a two-tailed t-test, for curves variance was measured through area under the curve, NS P>0.05.

Figure 24B:
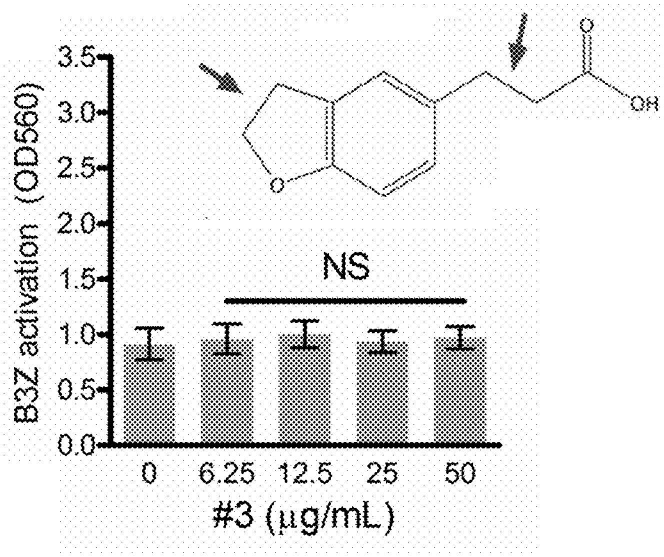

FIG. 24B is a graph with inset line drawing showing BzFβ's unique structure is integral for the enhancement of T cell response. DC2.4 cells treated with molecule #3, that is structurally similar to BzFβ, failed to evoke activation of the B3Z response. Red arrows denote structural variance from BzFβ. Data shown as mean of n≥3 experiments shown and analyzed using a two-tailed t-test, for curves variance was measured through area under the curve, NS P>0.05.

Figure 24C:
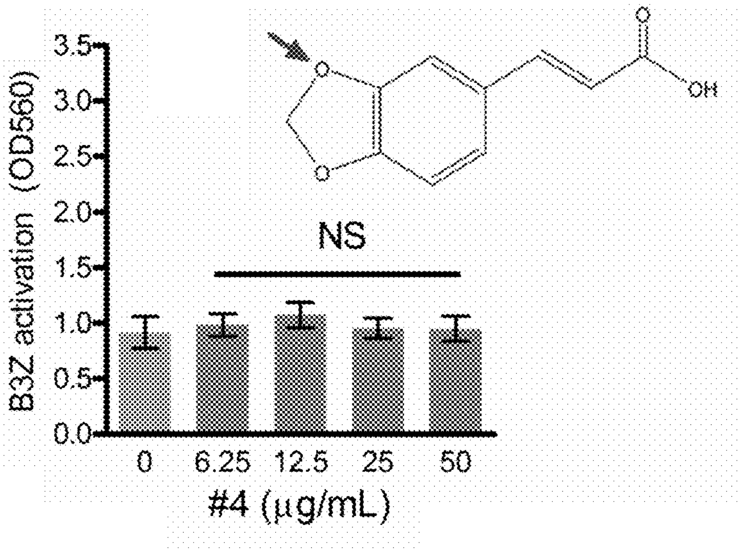

FIG. 24C is a graph with inset line drawing showing BzFβ's unique structure is integral for the enhancement of T cell response. DC2.4 cells treated with molecule #4, that is structurally similar to BzFβ, failed to evoke activation of the B3Z response. Red arrows denote structural variance from BzFβ. Data shown as mean of n≥3 experiments shown and analyzed using a two-tailed t-test, for curves variance was measured through area under the curve, NS P>0.05.

Figure 25:
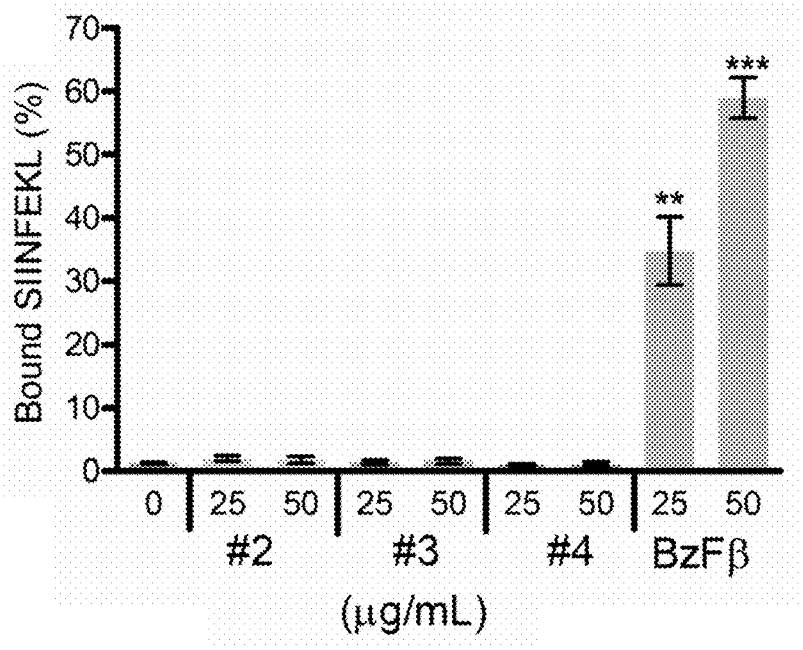

FIG. 25 is a graph showing BzFβ's unique structure is integral for the enhancement of T cell response. None of the BzFβ analogs, molecules #2 through #4, were found to facilitate binding of SIINFEKL to DC2.4. BzFβ at 25 and 50 μg/mL significantly enhance peptide binding (25 μg/mL BzFβ p-0.0034). Data shown as mean of n≥3 experiments and analyzed using a two-tailed t-test for curves variance was measured through area under the curve, NS P>0.05, * P<0.05,  P<0.01, * P<0.001. Error bars represent the standard deviation.

Figure 26:
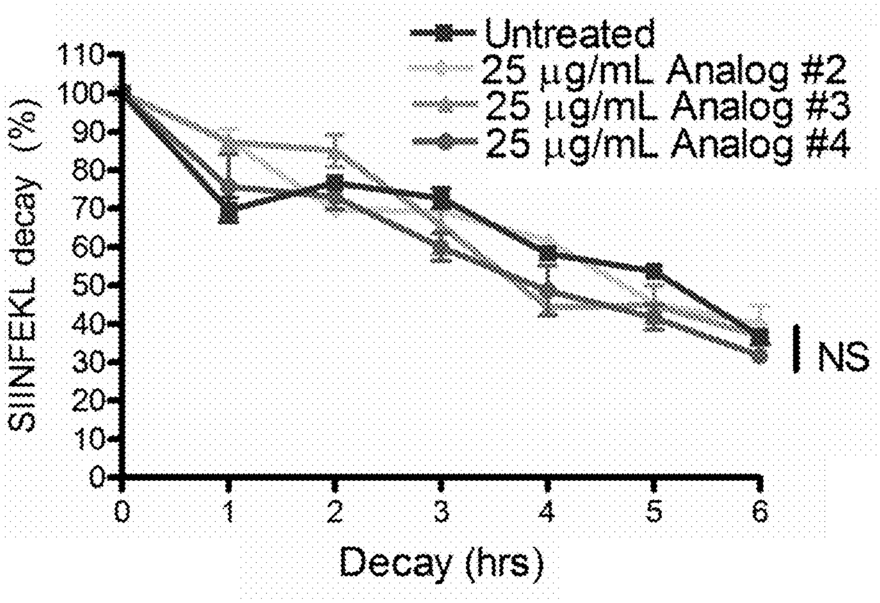

FIG. 26 is a graph showing BzFβ's unique structure is integral for the enhancement of T cell response. When compared to cells pulsed for 1 h with SIINFEKL (black squares), treatment with 25 μg/mL of each analog (purple diamonds, green triangles, red circles) did not affect the rate of SIINFEKL loss from the surface of the DC2.4 cells. Data shown as mean of n≥3 experiments and analyzed using a two-tailed t-test for curves variance was measured through area under the curve, NS P>0.05.

Figure 27A:
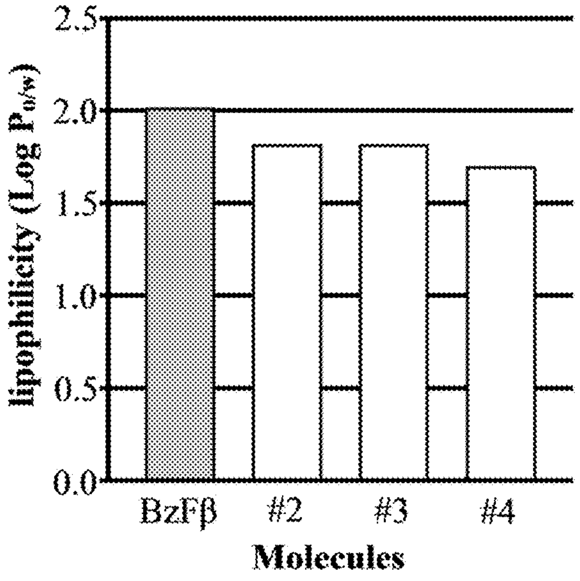

FIG. 27A is a graph showing the molecular properties predicted by Swiss ADME for BzFβ and its analogs. All four molecules are predicted to be similarly lipophilic. The consensus Log Pow is shown.

Figure 27B:
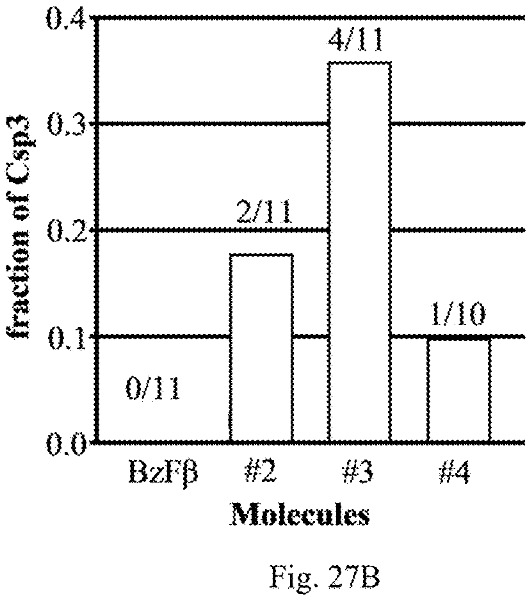

FIG. 27B is a graph showing the molecular properties predicted by Swiss ADME for BzFβ and its analogs. The molecules differ by the number of sp3 hybrid orbitals they contain. BzFβ has 0 of its 11 carbons, molecule #2 has 2 of its 11 carbons, molecule #3 has 4 of its 11 carbons, and molecule #4 has 1 of its 10 carbons with sp3 orbitals.

Figure 27C:
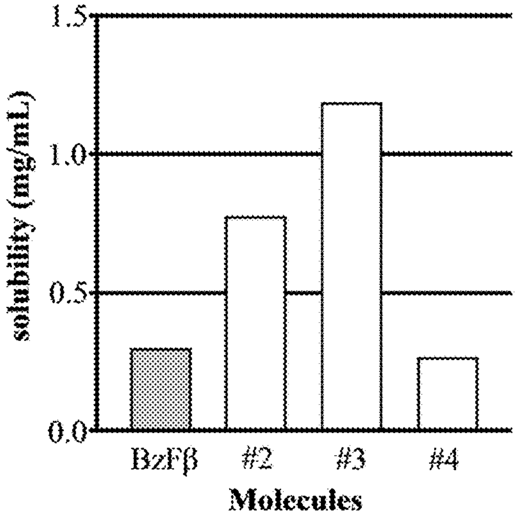

FIG. 27C is a graph showing the molecular properties predicted by Swiss ADME for BzFβ and its analogs. The predicted water solubility (expressed in mg of product soluble per mL of water) suggested that BzFβ and molecule #4 have similar water solubilities, while molecules #2 and #3 should be a bit more soluble.

Figure 28A:
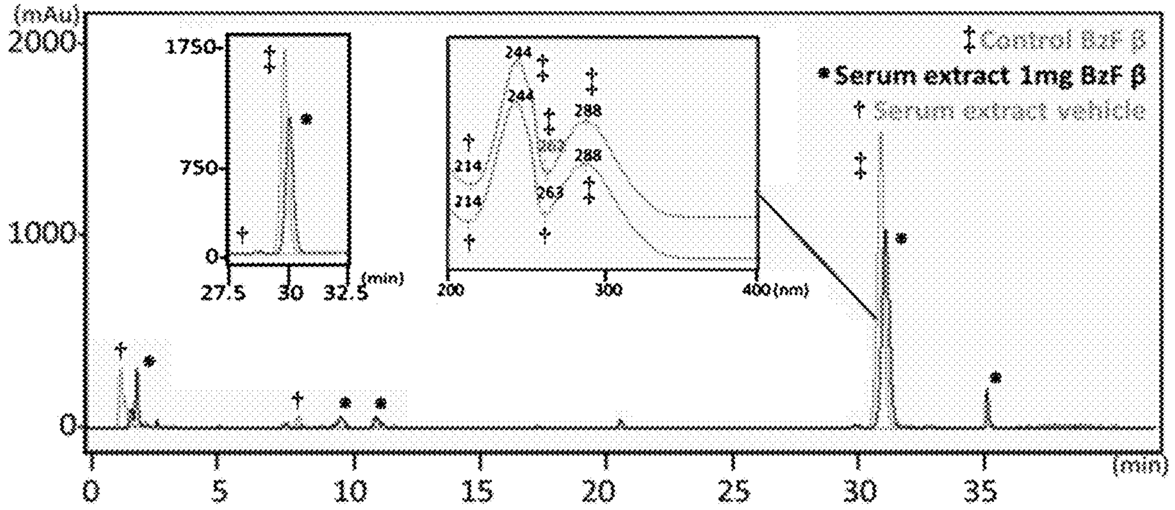

FIG. 28A is a graph showing BzFβ can be detected in the systemic circulation following delivery by oral gavage, iv, and im injections. A representative HPLC chromatogram from the serum of mice receiving 1 mg BzFβ po (*), compared to the tracing generated by the stock solution of BzFβ ($). The UV/VIS spectra of the BzFβ peaks at 30.5 and 30.7 min, respectively, is shown in the insert.

Figure 28B:
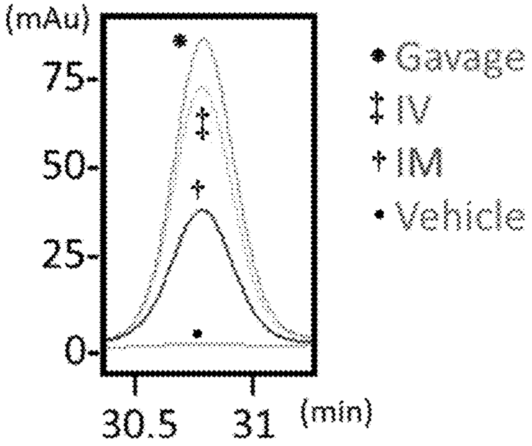

FIG. 28B is a graph showing BzFβ can be detected in the systemic circulation following delivery by oral gavage, iv, and im injections. Detection of BzFβ in the serum of mice that had received it by oral gavage, or iv or im injections compared to vehicle only.

Figure 28C:
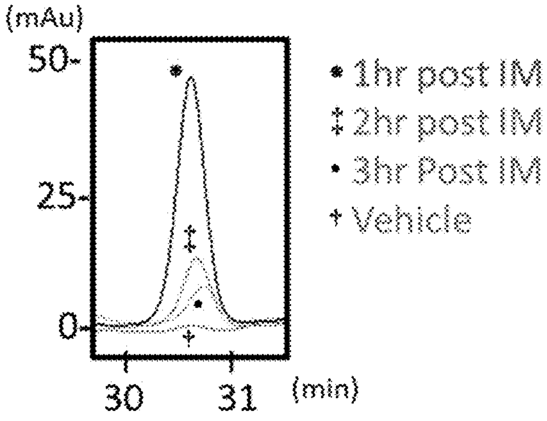

FIG. 28C is a graph showing BzFβ can be detected in the systemic circulation following delivery by intramuscular injections. The relative concentrations of BzFβ detected in serum samples 1, 2, or 3 h post-delivery.

Figure 29:
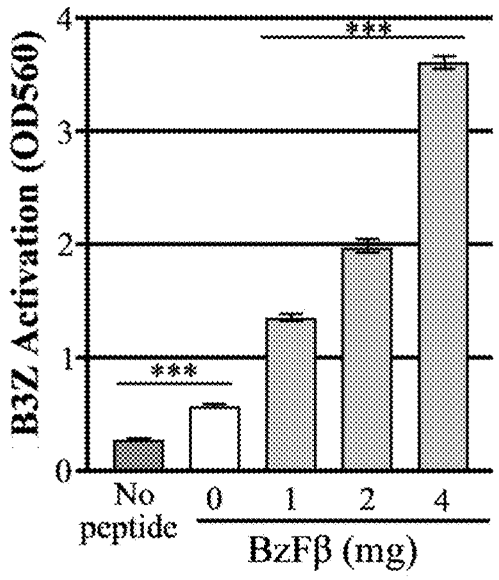

FIG. 29 is a graph showing in vivo administration of BzFβ and peptide increases peptide binding in vivo. Intravenous administration of 50 μg SIINFEKL peptide immediately followed by oral gavage with 1, 2, or 4 mg (50, 100, 200 mg/kg, respectively) of BzFβ significantly increased the ability of splenocytes to activate B3Z cells ex vivo. Data shown as mean of n≥3 mice analyzed using a two-tailed t-test CI=95%, NS P>0.05, * P<0.05,  P<0.01, * P<0.001. Error bars represent the standard deviation.

Figure 30:
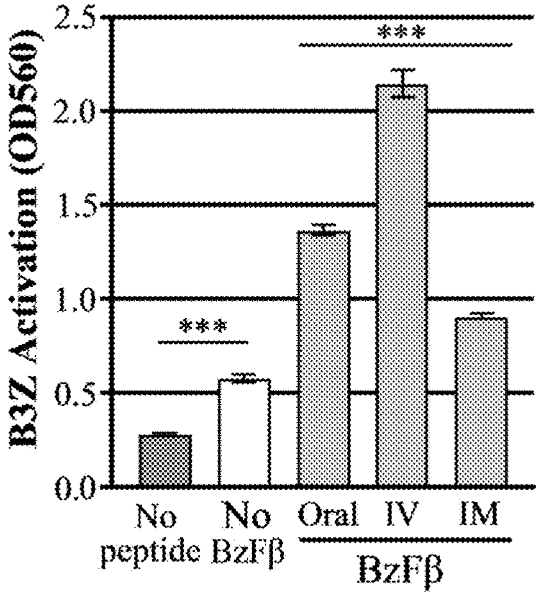

FIG. 30 is a graph showing in vivo administration of BzFβ and peptide increases peptide binding in vivo. The ability to enhance the in vivo binding of SIINFEKL was demonstrated following iv injection of 50 μg peptide and then either oral, iv, or im administration of BzFβ. Data shown as mean of n≥3 mice analyzed using a two-tailed t-test CI=95%, NS P>0.05, * P<0.05,  P<0.01, * P<0.001. Error bars represent the standard deviation.

Figure 31:
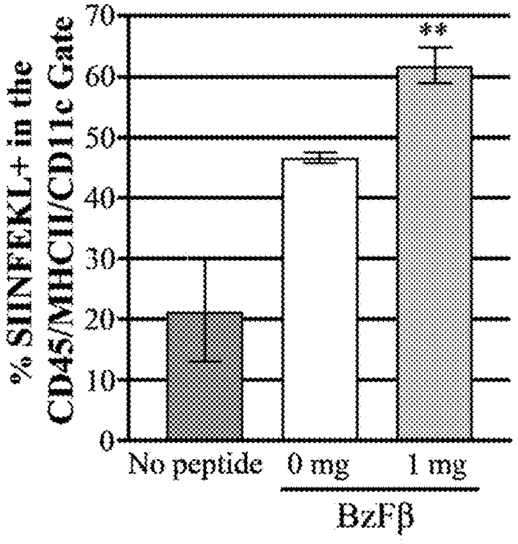

FIG. 31 is a graph showing in vivo administration of BzFβ and peptide increases peptide binding in vivo. Characterization of the splenocytes by flow cytometry shows that BzFβ enhances SIINFEKL binding in the CD45+/MHCII+/CD11c+ population in vivo (p=0.0079). Data shown as mean of n≥3 mice analyzed using a two-tailed t-test CI=95%, NS P>0.05, * P<0.05,  P<0.01, * P<0.001. Error bars represent the standard deviation.

Figure 32A:
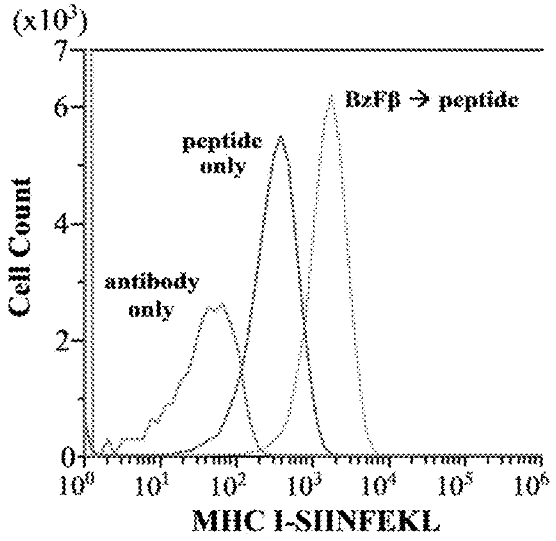

FIG. 32A is a graph showing BzFβ enhances loading of peptide at a dose compatible with the production of DC vaccines. Histograms of the peptide binding show that pre-treatment with BzFβ significantly enhanced SIINFEKL binding under conditions used to create peptide pulsed DC vaccines. BzFβ enhanced the number of SIINFEKL positive cells, but more significantly, it enhanced the amount of SIINFEKL per cell.

Figure 32B:
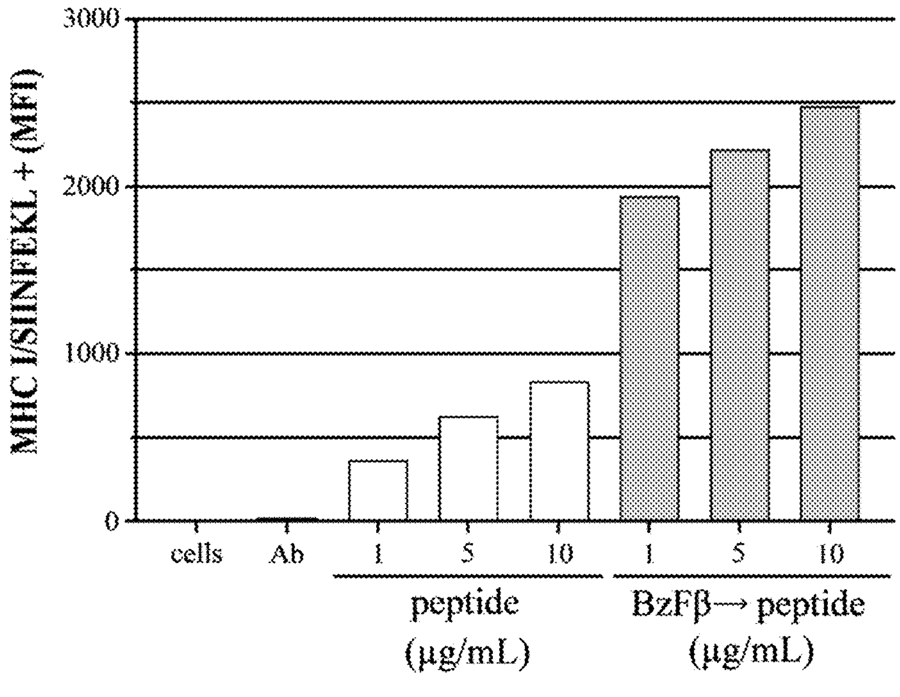

FIG. 32B is a graph showing BzFβ enhances loading of peptide at a dose compatible with the production of DC vaccines. DC2.4 cells ($1\times10^6$) were pre-treated for 1 h with 50 μg/mL BzFβ in 200 uL HBSS/2% FCS) at 37° C., washed, and then pulsed for 1 h with 1, 5, or 10 μg/mL SIINFEKL peptide. The cells were then stained with PE-labeled 25-D1.16 antibody at 10° C. for 30 min. Pre-treatment with BzFβ enhanced the binding of all three high doses of peptide commonly used to generate DC vaccines.

Figure 33A:
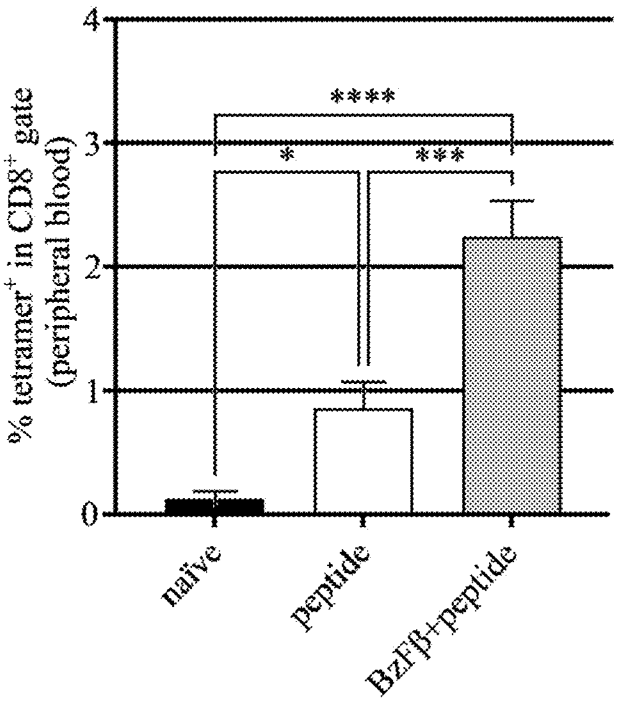

FIG. 33A is a graph showing immunization with DC2.4 cells treated in vitro with BzFβ and peptide enhances the resulting CD8+ antigen specific T cell response. Mice were vaccinated (primed then 1 week later they were boosted) by subcutaneous injection of $1.2\times10^6$ IFNγ matured DC2.4 cells that had been exposed in vitro to 50 μg/mL BzFβ for 2 h and then pulsed for 1 h with 1 μg/mL SIINFEKL peptide. Two weeks later, the percent of SIINFEKL specific CD8+ T cells in the peripheral blood were determined. Data shown as mean of n≥3 mice per group analyzed using a two-tailed t-test CI=95%, NS P>0.05, * P<0.05,  P<0.01, * P<0.001, **** P<0.0001. Error bars represent the standard deviation.

Figure 33B:
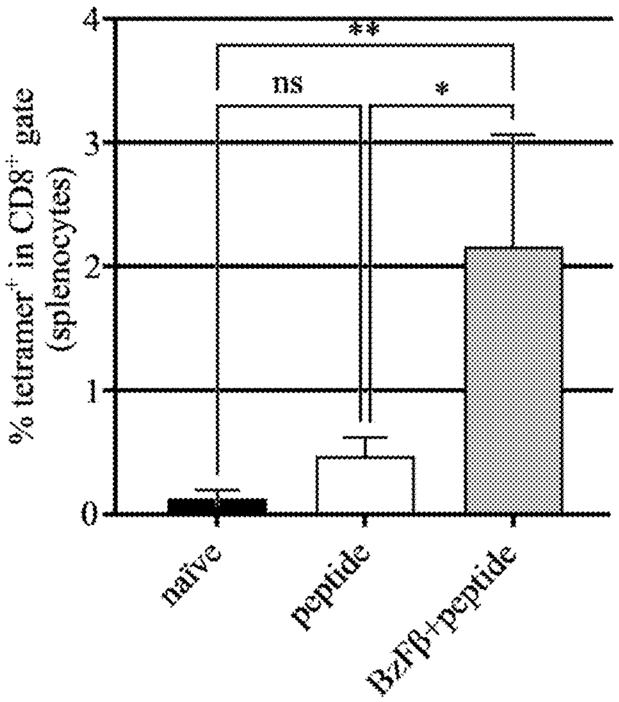

FIG. 33B is a graph showing immunization with in vitro treated DC2.4 cells with BzFβ and peptide enhances the resulting CD8+ antigen specific T cell response. Mice were vaccinated (primed then 1 week later they were boosted) by subcutaneous injection of $1.2\times10^6$ IFNγ matured DC2.4 cells that had been exposed in vitro to 50 μg/mL BzFβ for 2 h and then pulsed for 1 h with 1 μg/mL SIINFEKL peptide. Two weeks later, the percent of SIINFEKL specific CD8+ T cells in the splenocyte population were determined. Data shown as mean of n≥3 mice per group analyzed using a two-tailed t-test CI=95%, NS P>0.05, * P<0.05,  P<0.01, * P<0.001, **** P<0.0001. Error bars represent the standard deviation.

Figure 34:
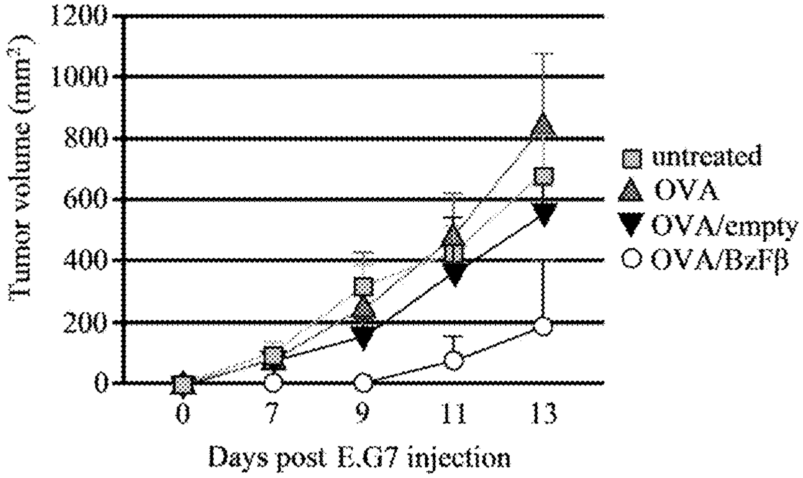

FIG. 34 is a graph showing PLGA encapsulated BzFβ enhances development of an anti-tumor response. Immunization of female C57BL/6crl mice with PLGA particles encapsulating whole ovalbumin, a mixture of empty and OVA containing particles (OVA/Empty), or a mixture of particles containing OVA or BzFβ (OVA/BzFβ) by intramuscular injection. The mice were then boosted with the same mixtures 10 days later. Ten days post the booster injections, $1\times10^6$ E.G7-OVA tumor cells were injected subcutaneously. Tumor growth was monitored every other day, and the width and lengths were measured. The tumor volumes were calculated as the (greatest width^2×greatest length)/2.

Figure 35:
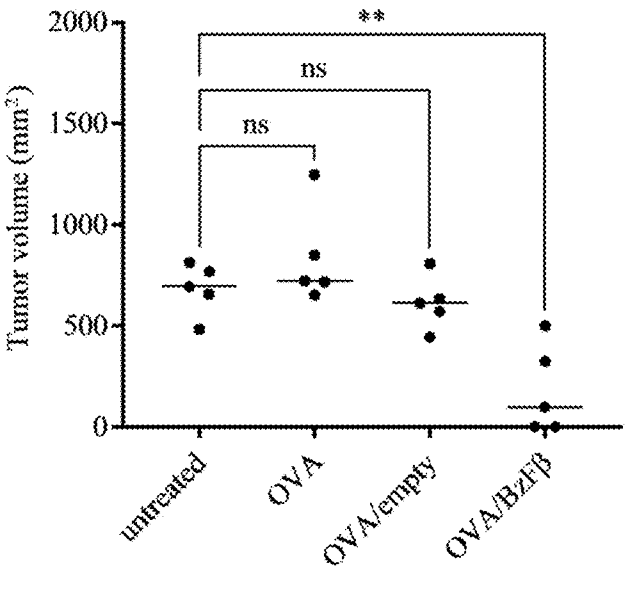

FIG. 35 is a graph showing PLGA encapsulated BzFβ enhances development of an anti-tumor response. Immunization of female C57BL/6crl mice with PLGA particles encapsulating whole ovalbumin, a mixture of empty and OVA containing particles (OVA/Empty), or a mixture of particles containing OVA or BzFβ (OVA/BzFβ) by intramuscular injection. The mice were then boosted with the same mixtures 10 days later. Ten days post the booster injections, $1\times10^6$ E.G7-OVA tumor cells were injected subcutaneously. Tumor volumes obtained at 13 days post tumor cell injection are shown. ns=non-significant; **=p≤0.01.

DETAILED DESCRIPTION OF THE INVENTION

As used herein, the singular forms "a", "an" and "the" include plural referents unless the context clearly dictates otherwise. Thus, for example, reference to "a compound" includes a mixture of two or more compounds and the like, unless specified to the contrary.

As used herein, "about" means approximately or nearly and in the context of a numerical value or range set forth means +/−15% of the numerical.

The term "administration", "administering", and variants thereof (e.g., "administering" a compound) is used throughout the specification to describe the delivery or introduction of the compound or a prodrug of the compound into the system of the animal in need of treatment. When a compound of the invention or prodrug thereof is provided in combination with one or more other active agents, "administration" and its variants are each understood to include concurrent and sequential introduction of the compound or prodrug thereof and other agents.

Compounds of the subject invention be administered a number of ways including, but not limited to, oral, parenteral (such term referring to intravenous and intra-arterial as well as other appropriate parenteral routes), intrathecal, intraventricular, intraparenchymal (including into the spinal cord, brainstem or motor cortex), intracisternal, intracranial, intrastriatal, intranigral, and transdermal, among others which term allows a compound of the subject invention to be carried to the ultimate target site where needed. A compound of the subject invention can be administered in the form of active compound, admixtures, or compositions thereof. The compositions according to the present invention may be used without adjuvant, without bio-absorption enhancing agent, without diluent. Alternatively, compositions according to the present invention may include one or more of the adjuvant, bio-absorption enhancing agent, and diluent.

Administration will often depend upon the type of vaccine, such as dendritic cell vaccines as compared to small molecule antigen vaccines, epitope vaccines, DNA vaccines, recombinant DNA vaccines, messenger RNA (mRNA) vaccines, subunit vaccines, recombinant vaccines, conjugate vaccines, or toxoid vaccines, as well as the disease or condition targeted by the vaccine. For example, administration may preferably be via administration into the cerebral spinal fluid or by direct administration into the affected tissue in the brain, intratumoral for solid cancers/proliferative disorders, or be via a parenteral route, for example, intravenously, for systemic diseases.

The therapeutic compound is administered and dosed in accordance with good medical practice, taking into account the clinical condition of the individual patient, the site and method of administration, scheduling of administration, patient age, sex, body weight, and other factors known to medical practitioners.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state. Preferably, the compound of the invention, (2E)-3-(1-benzofuran-5-yl)prop-2-enoic acid, is administered in an isolated or pure form.

The term "incubation period" as used herein refer to a period of time in which a cell is exposed to an external influence, either another cell type or compound. More particularly, the incubation period can refer to exposure of an antigen presenting cell to one or more compounds to elicit a change in the antigen loading or exposure of a leukocyte to an antigen presenting cell.

As used herein, the term "modulation" and variations thereof refers to a change of amount of immune response to a stimuli when compared to the amount or quality of activity prior to modulation. For example, modulation includes the change, either an increase (stimulation or induction) or a decrease (inhibition or reduction) in chemokine release. As further an example, the modulation includes an increase in t-cell responsiveness to an antigen stimulus, resulting in a change in the absolute or relative amount of a t-cell response.

As used herein, the term "therapeutically effective amount" refers to concentrations or amounts of components of the invention that enhance an active vaccine compound or agent, with or without other adjuvants, to elicit the biological or medicinal response in a tissue, system, animal or human that is being sought by a researcher, veterinarian, medical doctor or other clinician. In reference to a disease, illness, condition, infection, an effective amount comprises an amount sufficient to prevent or ameliorate the disease. In some embodiments, an effective amount is an amount sufficient to delay development of disease. The therapeutically effective amount can, when used for proliferative disorder therapy, result in the amelioration of cancer or other proliferative disorders or one or more symptoms thereof, prevent advancement of cancer or other proliferative disorder, or cause regression of cancer or other proliferative disorder.

A therapeutically effective amount of the therapeutic compound or a pharmaceutically acceptable salt, hydrate, or solvate thereof refers to that amount being administered which will enhance, to some extent, a vaccine. Nonlimiting examples of vaccines include dendritic cell vaccines, small molecule antigen vaccines, epitope vaccines, messenger RNA (mRNA) vaccines, DNA vaccines, recombinant DNA vaccines, subunit vaccines, recombinant vaccines, conjugate vaccines, or toxoid vaccines. In reference to the treatment of a proliferative cellular disorder, a therapeutically effective amount refers to the amount which: (1) reduces the size of a tumor, (2) inhibits (i.e. stopping or slowing to some extent) tumor metastasis, (3) inhibits (i.e. stopping or slowing to some extent) tumor growth, or (4) inhibits (i.e. stopping or slowing to some extent) cellular proliferation.

A "prophylactically effective amount" refers to concentrations or amounts of components such as the compound(s) of the invention along with an active vaccine compound or agent, with or without other adjuvants, that are sufficient to result in the prevention, recurrence, or spread of disease. The prophylactically effective amount may refer to the amount sufficient to prevent initial disease, recurrence or spread of the disease or the occurrence of the disease in a patient, including, but not limited, to patients particularly susceptible to the disease, or occurrence of disease in another patient, i.e. spread of disease.

As used herein, "treatment" refers to obtaining beneficial or desired clinical results. Beneficial or desired clinical results include, but are not limited to, any one or more of: alleviation of one or more symptoms, diminishment of extent of infection, stabilization (i.e., not worsening) of the state of infection, preventing or delaying spread of the disease (such as pathogen growth or replication), preventing or delaying occurrence or recurrence of the disease, delay or slowing of disease progression and amelioration of the disease state. The methods of the invention contemplate any one or more of these aspects of treatment. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

The term "patient" is used herein to describe members of the animal kingdom, such as but not milted to primates including humans, gorillas and monkeys; rodents, such as mice, fish, reptiles and to whom treatment, including prophylactic treatment, with the composition(s) according to the present invention, is provided. The patient may be any animal requiring therapy, treatment, or prophylaxis, or any animal suspected of requiring therapy, treatment, or prophylaxis. For treatment of those infections, conditions or disease states which are specific for a specific animal such as a human patient, the term patient refers to that specific animal.

As used herein, the term "proliferative disorders" broadly encompasses any neoplastic disease(s) including those which are potentially malignant (pre-cancerous) or malignant (cancerous) and covers the physiological condition in mammals that is typically characterized by unregulated cell growth. The term therefore encompasses the treatment of tumors. Examples of such proliferative disorders include cancers such as carcinoma, lymphoma, blastoma, sarcoma, and leukemia, as well as other cancers disclosed herein. The compositions disclosed herein are useful for treating all types of cancer, and include breast cancer; ovarian cancer, multiple myeloma tumor specimens, pancreatic cancer and blood malignancies, such as acute myelogenous leukemia, (Turkson, et al., U.S. Pat. No. 8,609,639; Jove, et al., WO 00/44774), multiple myeloma, acute myelogenous leukemia (Dalton, et al., PCT/US2000/001845), head and neck cancer, lung cancer, colorectal carcinoma, prostate cancer, melanoma, sarcoma, liver cancer, brain tumors, multiple myeloma, leukemia, cervical cancer, colorectal carcinoma, liver cancer, gastric cancer, prostate cancer, renal cell carcinoma, hepatocellular carcinomas, gastric cancers, and lymphomas (Li, et al., U.S. application Ser. No. 12/677,513), fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, a seminoma, an embryonal carcinoma, Wilms' tumor, testicular tumor, lung carcinoma, small cell lung carcinoma, bladder carcinoma, epithelial carcinoma, a glioma, an astrocytoma, medulloblastoma, craniopharyngioma, ependymoma, pinealoma, hemangioblastoma, acoustic neuroma, oligodendroglioma, meningioma, neuroblastoma, retinoblastoma; acute lymphocytic leukemia, acute myelocytic leukemia, chronic leukemia, and polycythemia vera (Jove, et al., U.S. application Ser. No. 10/383,707).

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

A "pharmaceutically acceptable" component is one that is suitable for use with humans and/or animals without undue adverse side effects (such as toxicity, irritation, and allergic response) commensurate with a reasonable benefit/risk ratio.

The pharmaceutical compositions of the subject invention can be formulated according to known methods for preparing pharmaceutically useful compositions.

As used herein, the phrase "pharmaceutically acceptable carrier" means any of the standard pharmaceutically acceptable carriers, such as a solvent, suspending agent or vehicle, for delivering the compound or compounds in question to the animal or human. The carrier may be liquid or solid and is selected with the planned manner of administration in mind. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Liposomes, micelles, FDA-approved poly(lactic-co-glycolic acid) (PLGA) microparticles and PLGA nanoparticles are also a pharmaceutical carrier. Examples of carriers include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W Easton Pa., Mack Publishing Company, 19.sup.th ed.) describes formulations which can be used in connection with the subject invention. The carrier includes any and all solvents, dispersion media, vehicles, coatings, diluents, antibacterial and antifungal agents, isotonic and absorption delaying agents, buffers, carrier solutions, suspensions, colloids, and the like. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The compounds of the present invention include all hydrates and pharmaceutically acceptable salts of the propanoic acids that can be prepared by those of skill in the art, for example by reacting the inventive compound with a sufficiently basic compound, such as an amine, affording a physiologically acceptable anion. Under conditions where the compounds of the present invention are sufficiently basic or acidic to form stable nontoxic acid or base salts, administration of the compounds as salts may be appropriate. Suitable inorganic salts may also be formed by reaching the compound with a basic compound, such as a basic salt of ammonium, calcium magnesium, potassium, or sodium, such as ammonium bicarbonate. When reference is made to a compound or administering a compound, the recitation of the compound includes a pharmaceutically acceptable salt thereof.

The compounds of the present invention can be formulated as pharmaceutical compositions and administered to a patient, such as a human patient, in a variety of forms adapted to the chosen route of administration, e.g., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard- or soft-shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient presenting the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the invention to the skin are disclosed in Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art (See, Borch et al., U.S. Pat. No. 4,938,949).

Accordingly, the invention includes a pharmaceutical composition comprising a compound of the present invention as described above, or a pharmaceutically acceptable salt thereof, in combination with a pharmaceutically acceptable carrier. Pharmaceutical compositions adapted for oral, topical or parenteral administration, comprising an amount of one or more compounds effective to treat a bacterial infection, are a preferred embodiment of the invention.

This invention addresses the severe need for new classes of adjuvant compounds to enhance vaccine treatment. The invention is now further described by way of the following examples, which, while illustrative of the invention, are not intended as limitations to the scope. It should be understood that the examples and embodiments described herein are for illustrative purposes only and that various modifications or changes in light thereof will be suggested to persons skilled in the art and are to be included within the spirit and purview of this application.

Two-tailed t-tests were conducted when comparing values against control only ANOVA was utilized when measuring variance between sample groups. Bonferroni's post-test was utilized to test statistical significance. GraphPad Prism 4 and 8 were used for analysis. NS P>0.05, * P<0.05,  P<0.01, * P<0.001, **** P<0.0001, error bars represent standard deviation.

Using the ovalbumin peptide, $SIINFEKL_{257-264}$ (SEQ ID NO: 1), an antibody recognizing SIINFEKL bound to MHC class I, and SIINFEKL-specific tetramers, the ability of BzFβ to enhance peptide exchange on both the human HLA-A2 and murine H-2Kb MHC class I complexes is revealed. Molecular docking studies predict that BzFβ could interact with the F-pocket of MHC class I in a way that would induce H-2Kb and HLA-A*02-01 peptide receptive states. This mechanism of action would allow peptides to bind with increased efficiency and could potentially enhance the efficacy of peptide-pulsed DC vaccines. Herein, BzFβ's ability to enhance peptide exchange in vitro and in vivo is demonstrated. The unmet need for the identification and development of bioavailable molecules capable of modulating antigen specific immune responses, motivated a search for non-peptide-based compounds proficient at enhancing the in vitro and in vivo presentation of antigen and/or antigen-specific T cell activation.

Example 1: Initial Screening

The initial screening process utilized the immortalized murine dendritic cell line, DC2.4 as the antigen-presenting cell and was chosen because it closely models primary bone marrow-derived dendritic cell responses and can readily present MHC class I antigens to CD8+ T cells. (Shen, et al., Cloned dendritic cells can present exogenous antigens on both MHC class I and class II molecules. J Immunol. 1997 Mar. 15;158 (6): 2723-30; Lin, et al., Soluble CD83 alleviates experimental autoimmune uveitis by inhibiting filamentous actin-dependent calcium release in dendritic cells. Fron Immunol. 2018 Jul. 9; 9:1567). The T cell hybridoma cell line, B3Z, is a CD8+ SIINFEKL peptide specific T-cell hybridoma expressing a beta-galactosidase (β-gal) reporter gene driven by NF-AT elements on the interleukin 2 (IL-2) promoter (Karttunen, et al., Detection of rare antigen-presenting cells by the lacZ T-cell activation assay suggests an expression cloning strategy for T-cell antigens. Proc Natl Acad Sci USA. 1992 Jul. 1;89 (13): 6020-4). Activation of B3Z leads to production of β-gal whose presence can be quantified using the optimized detection assay described by Jendresen et al. (Jendresen, et al., An improved CPRG colorimetric ligand-receptor signal transduction assay based on beta-galactosidase activity in mammalian BWZ-reporter cells. J Pharmacol Toxicol Methods. 2018 March-Apr; 90:67-75).

The DC2.4 cell line, provided by Dr. Kenneth Rock (University of Massachusetts). was routinely cultured in complete Dulbecco's Modified Eagle Medium (cDMEM) containing 4500 mg/mL glucose (Gibco™, Thermo Fisher Scientific Inc., Waltham, MA; cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems, Inc., Minneapolis, MN; cat. no. 11150H) at 37° C. in an atmosphere containing 5% $CO_2$ and 95% humidity. The B3Z.A3 cell line, provided by Dr. Nilabh Shastri (University of California Berkeley, Office of Technology Licensing) was cultured in RPMI 1640+GlutaMAX-1 (Gibco™; Cat. No. 61870-036) containing 2000 mg/mL glucose and supplemented with 40 μM 2-mercaptoethanol (B-Me) and 1 mM sodium pyruvate (Gibco™, cat. no. 11360-070). All culture media included 50 units/mL penicillin and 50 μg/mL streptomycin and 10% by volume heat inactivated fetal bovine serum (FBS) (Atlanta Biologicals, R&D Systems, Inc., Minneapolis, MN; cat. no. S12450H). Cells were cultured at 37° C., in an atmosphere containing 5% $CO_2$ and 95% humidity.

H-$2K^b$ OVA257-264 peptide, SIINFEKL (cat. no. AS-60193-1; SEQ ID NO: 1) was purchased from AnaSpec Inc (Fremont, CA). Chlorophenol red-β-D-galactopyranoside (CPRG, cat. no. 10884308001) was purchased from Sigma Chemical Co (St. Louis, MO). CPRG stock was prepared to 175 μg/mL in sterile $H_2O$ and a working solution of 1.75 μg/mL was used.

DC2.4 cells ($2.5\times10^4$ cells/well) were seeded at 100 μL/well in 96 well tissue culture white sided/white bottom plate and incubated overnight to allow for cell adherence. 37° C. in an atmosphere containing 5% $CO_2$ and 95% humidity. Following pre-treatment of the DC2.4 cells (1-24 h) with escalating doses of the test molecules, the cells were washed, pulsed with 0.5 nM of the MHC class I H-2Kb peptide, SIINFEKL, for 1 h, and then co-cultured with the CD8+ T cell hybridoma, B3Z.

The level of B3Z cell activation and the effects of the various test molecules on B3Z activation were quantified in cell lysates using the β-gal chromogenic substrate, CPRG. The media was removed and 100 μL of 250 μM CPRG reconstituted in the lysis buffer (1× DPBS, 0.2% v/v saponin, 20 mM magnesium chloride) was added directly to each well. Cells were maintained at 37° C. prior to measurement. The absorbance at 560 nm (700 nm for background) was intermittently monitored using a BioTek Synergy HTX multimode microplate reader (Winooski, VT) to detect β-gal activity. CPRG lysis buffer and B3Z cells only served as the negative controls. All treatments were performed in triplicate and all experiments were repeated a minimum of three times.

Figure 1:
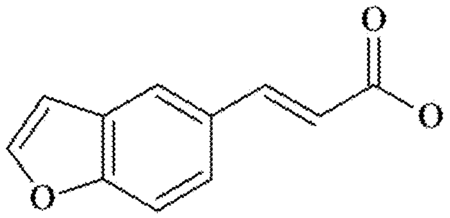
FIG. 1 is a line drawing showing the structure of (2E)-3-(1-benzofuran-5-yl) prop-2-enoic acid (BzFβ). Molecular weight: 188.18 g/mol.

This screening process (manuscript in preparation) led to the identification of BzFβ, (3-(1-benzofuran-5-yl) prop-2-enoic acid), seen in FIG. 1, as a promising hit.

Example 2: Toxicity

BzFβ was then examined for its effect on the viability of several murine and human cell lines and primary murine splenocytes. The cytotoxicity of BzFβ was assessed using the CellTiter-Glo colorimetric assay system according to manufacturer's instructions to determine BzFβ's effect on the viability of several murine and human cell lines and primary murine splenocytes.

DC2.4 cell line (Dr. Kenneth Rock, University of Massachusetts), RAW 264.7 cell line (American Type Culture Collection (ATCC), Manassas, VA; TIB 71), and IMG cell line (Millipore™, Merck KGaA, Burlington, MA; cat. no. SC-C134) were each cultured in complete Dulbecco's Modified Eagle Medium (cDMEM) containing 4500 mg/ml glucose (Gibco™, Thermo Fisher Scientific Inc., Waltham, MA; cat. no. 10566-016) and supplemented with GlutaMAX, 50 U/mL penicillin and 50 μg/mL streptomycin (Gibco™; cat. no. 15070-063) and 10% heat inactivated fetal bovine serum (FBS) (R&D Systems, Inc., Minneapolis, MN; cat. no. 11150H) at 37° C. in an atmosphere containing 5% $CO_2$ and 95% humidity. HEK293T was cultured in complete Dulbecco's Modified Eagle Medium (cDMEM) containing 4500 mg/mL glucose (Gibco™, cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems cat. no. 11150H) at 37° C. in an atmosphere containing 5% $CO_2$ and 95% humidity.

Six- to ten-week-old female C57BL/6NCrl mice (Charles River Laboratories, Wilmington, MA; cat. no. 027) were maintained in accord with the NIH Guide for the Care and Use of Laboratory Animals. Mice were maintained in an INOVIVE individually ventilated cage system with 3 mice per cage containing 100% virgin wood pulp bedding (Harlan Teklad™, Inotiv Inc., West Lafayette, IN; cat. no. 7099). Water and food (Harlan Teklad™, Inotiv Inc., West Lafayette, IN; cat. no. 8640) were available ad libitum. Spleens were collected in 4 mL of Hanks Balanced Salt Solution (HBSS) and converted to a single cell suspension using sterile pouches and a Steward Stomacher 80 Biomaster Blender (Fisher Scientific, cat. no. 14-285-27). The resulting cell suspension was pelleted and suspended in 4 mL freshly prepared red blood cell lysis buffer (150 mM $NH_4Cl$, 10 mM $NaHCO_3$, 0.1 mM EDTA in sterile distilled $H_2O$) for 1-3 minutes. The splenocytes were pelleted and filtered through 70 μM EASYstrainer filters (USA Scientific, cat. no. 5654-2070). The cell count was determined using the MUSE cell viability kit (MCH600103) and MUSE Cell Analyzer (Luminex Corp, Austin TX).

Murine splenocytes were cultured in complete RPMI (CRPMI) comprised of RPMI 1640+GlutaMAX-1 (Gibco™; cat. no. 61870-036) containing 2000 mg/mL glucose and supplemented with 40 μM 2-mercaptoethanol, 50 units/mL penicillin and 50 μg/mL streptomycin and 10% by volume heat inactivated fetal bovine serum (FBS) (Atlanta Biologicals, R&D Systems, Inc., Minneapolis, MN; cat. no. S12450H). Cells were cultured at 37° C., in an atmosphere containing 5% $CO_2$ and 95% humidity.

The cytotoxicity of BzFβ was assessed using the Invitrogen™ CellTiter-Glo cell colorimetric viability assay system (Thermo Fisher Scientific Inc., Waltham, MA; cat. no. P3566). according to manufacturer's instructions. Briefly, immortalized cells or murine splenocytes were plated in a volume of 100 μL into 96-well white flat-bottom tissue-culture plates at $1\times10^4$ or $5\times10^4$ cells per well, respectively, and incubated at 37° C., 5% $CO_2$ overnight for adherence. Two-fold serial dilutions of BzFβ were prepared in cDMEM and triplicate wells of cells were treated at each dose for 7, 24 or 48 h. CellTiter-Glo was added 1:1 in the media and the level of chemiluminescence was measured using luminescence at wavelengths of 200 nm to 700 nm through a photomultiplier on BioTek's Synergy HTX multimode microplate reader. All microplate viability measurements are reported as a percentage of vehicle only control cells.

Figure 2:
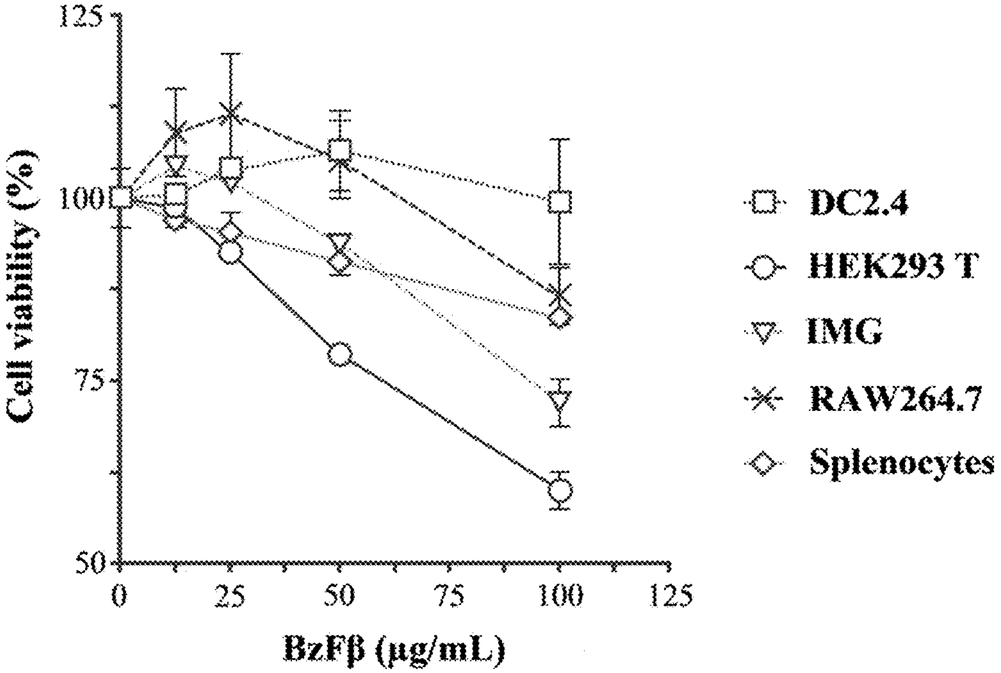
FIG. 2 is a graph showing the evaluation of BzFβ toxicity to murine and human immortalized cell lines, and to murine primary splenocytes was examined 24 h after being treated with increasing doses of BzFβ. Shown is the percent cell viability as compared to untreated cells.

It was found that across all the cell lines examined, except HEK293T, 24 h exposure to BzFβ at concentrations lower than 50 μg/mL (266 μM) had small effects on cell viability, as seen in FIG. 2. The viability of primary murine splenocytes was also minimally affected at concentrations below 50 μg/mL, as seen in FIG. 2. The IC50 for cell viability was calculated to be 1151 μM for DC2.4; 432 μM for HEK 293; 316 μM for IMG; 783 for RAW 264.7; and 402 μM for freshly isolated murine splenocytes. Based on these findings, all subsequent assays utilized doses of BzFβ less than or equal to 266 μM (50 μg/mL).

Example 3: BzFβ Enhances APC Presentation of an Exogenous Peptide to Antigen-Specific T Cells DC2.4 cells, provided by Dr. Kenneth Rock (University of Massachusetts), were routinely cultured in complete Dulbecco's Modified Eagle Medium (cDMEM) containing 4500 mg/mL glucose (Gibco™, cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems cat. no. 11150H) at 37° C. in an atmosphere containing 5% $CO_2$ and 95% humidity. B3Z.A3 cells, provided by Dr. Nilabh Shastri (University of California Berkeley, Office of Technology Licensing), were cultured in RPMI 1640+GlutaMAX-1 (Gibco™, cat. no. 61870-036) containing 2000 mg/mL glucose and supplemented with 40 μM 2-mercaptoethanol (B-Me) and 1 mM sodium pyruvate (Gibco™, cat. no. 11360-070). Murine splenocytes were cultured in complete RPMI (cRPMI) comprised of RPMI 1640+GlutaMAX-1 (Gibco™, cat. no. 61870-036) containing 2000 mg/mL glucose and supplemented with 40 μM 2-mercaptoethanol. All culture media included 50 units/mL penicillin and 50 μg/mL streptomycin and 10% by volume heat inactivated fetal bovine serum (FBS) (Atlanta Biologicals S12450H). Cells were cultured at 37° C., in an atmosphere containing 5% $CO_2$ and 95% humidity. BzFβ ((2E)-3-(1-benzofuran-5-yl) prop-2-eonic acid) (CAS no. 1210059-73-6, cat. no. CSSB00016286531) (SMILES OC(=O)/C=C\clccc2c (c1) cco2) was purchased from Chemspace (Monmouth Junction, NJ), and SIINFEKL (AnaSpec Inc., Fremont, CA; cat. no. AS-60193-1; SEQ ID NO: 1). The compound (2E)-3-(1,3-benzodioxol-5yl) acrylic acid (cat.

no. 146242) and chlorophenol red-β-D-galactopyranoside (CPRG, cat. no. 10884308001) were purchased from Sigma Chemical Co (St. Louis, MO). CPRG stock was prepared to 175 μg/mL in sterile $H_2O$ and a working solution of 1.75 μg/mL was used.

Activation of B3Z T cell hybridoma cells was assessed following their exposure to various MHC class I H-2Kb positive cell lines presenting the SIINFEKL peptide. B3Z are a CD8+ SIINFEKL peptide specific T-cell hybridoma expressing a beta-galactosidase (β-gal) reporter gene driven by NF-AT elements on the interleukin 2 (IL-2) promoter. (Karttunen, et al., Detection of rare antigen-presenting cells by the lacZ T-cell activation assay suggests an expression cloning strategy for T-cell antigens. Proc Natl Acad Sci USA. 1992 Jul. 1;89 (13): 6020-4). Activation of B3Z leads to production of β-gal whose presence can be quantified using the optimized detection assay described by Jendresen et al. (Jendresen, et al., An improved CPRG colorimetric ligand-receptor signal transduction assay based on beta-galactosidase activity in mammalian BWZ-reporter cells. J Pharmacol Toxicol Methods. 2018 March-Apr; 90:67-75).

To stimulate β-gal production in the B3Z, the H-2Kb murine cell lines, DC2.4, B16F10, and E.G7-OVA, or freshly isolated murine splenocytes, were plated at a density of 2.5 or $5\times10^4$ cells/well (100 μL/well in 96 well plates) and cultured overnight at 37° C. in an atmosphere containing 5% $CO_2$ and 95% humidity. The cells were washed with DPBS and then treated for 1-24 h with the indicated concentrations of BzFβ suspended in complete media. Vehicle controls were always included.

Following the pretreatment with BzFβ, the media was removed from DC2.4 cells or was removed following pelleting of nonadherent cells in the plate. The cells were then pulsed with various concentrations of SIINFEKL peptide (0.5 nM) for the indicated lengths of time (1 h if not otherwise indicated). The cells were washed and then 100 μL of complete DMEM containing $5\times10^4$ B3Z cells was added. The co-culture was incubated at 37° C. for 19 h to allow for B3Z activation.

To detect activation of the B3Z cells, the media was removed and 100 μL of 250 μM CPRG reconstituted in the lysis buffer (1× DPBS, 0.2% v/v saponin, 20 mM magnesium chloride) was added directly to each well. Cells were maintained at 37° C. prior to measurement. The absorbance at 560 nm (700 nm for background) was intermittently monitored using a BioTek Synergy HTX multimode microplate reader (Winooski, VT) to detect β-gal activity. CPRG lysis buffer and B3Z cells only served as the negative controls. All treatments were performed in triplicate and all experiments were repeated a minimum of three times.

Figure 3:
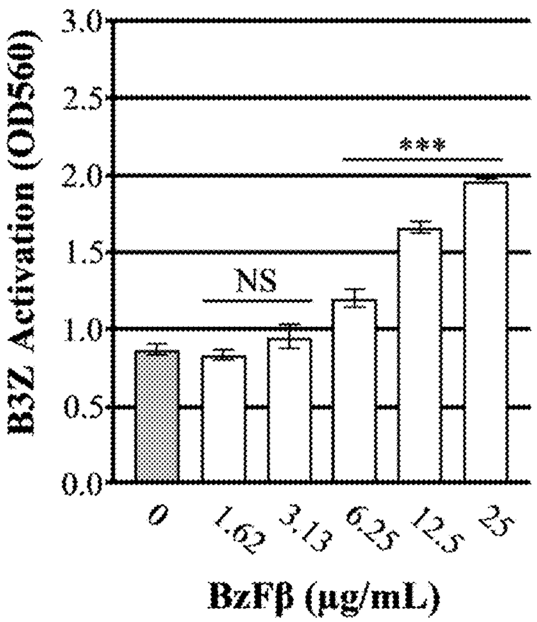
FIG. 3 is a graph showing BzFβ significantly enhances the ability of peptide pulsed DC2.4 to activate the CD8+ T cell hybridoma, B3Z. DC2.4 were treated with BzFβ as indicated for 6 h and then pulsed with 0.5 nM SIINFEKL peptide for 1h. Co-treatment of B3Z with the treated DC2.4 for 19 h resulted in significant enhancement of B3Z activation at doses above 6.25 μg/mL ($p<0.001$). Data shown is the mean of n≥3 experiments analyzed using a two-tailed t-test compared to control, NS $P>0.05$, * $P<0.05$,  $P<0.01$, * $P<0.001$. Error bars represent the standard deviation.
Figure 4:
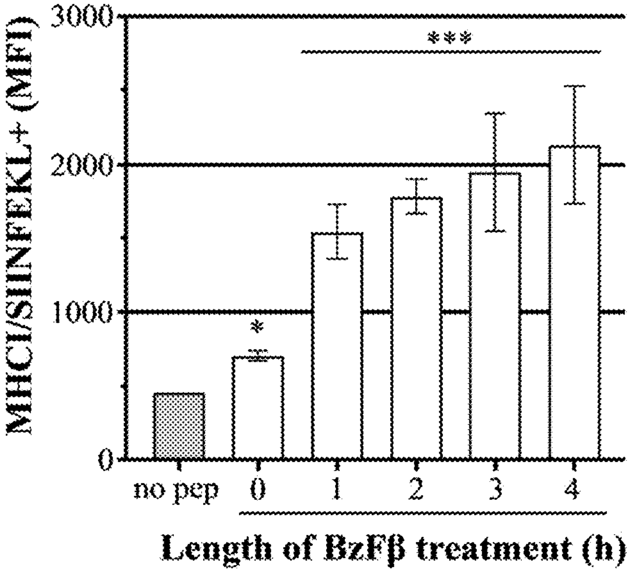
FIG. 4 is a graph showing BzFβ rapidly enhances the ability of DC2.4 to bind to peptide. Staining of DC2.4 cells with the MHC class I/SIINFEKL specific antibody (25-

When 100 μL of DC2.4 cells ($5\times10^5$/mL) were pretreated in 96 well plates with up to 25 μg/mL (133 μM) BzFβ for 6 h and then co-cultured for 19 h with an equal number of B3Z cells, doses greater than 3.13 μg/mL (17 μM) were found to significantly enhance B3Z cell activation, seen in FIG. 3 ($p<0.001$). Direct treatment of B3Z cells with BzFβ alone had no effect on cell viability or cell activation (data not shown). Examining the kinetics of the BzFβ activity revealed it capable of significantly enhancing binding of SIINFEKL to DC2.4 cells in less than 1 h, seen in FIG. 4, and activating B3Z in as little as 5 minutes, seen in FIG. 5. Such a rapid effect suggests that BzFβ likely functions by facilitating binding of peptides within the MHC class I complex.

To visualize the magnitude of effect the BzFβ has on the B3Z response, DC2.4 cells were co-treated for 1 h with low concentrations (15 pM to 1 nM) of SIINFEKL in the presence of 25 μg/mL BzFβ. After a 19 h coculture with B3Z, the BzFβ response was found to be significantly greater than that obtained with peptide pulsed DC2.4 alone, seen in FIG. 6 ($p<0.001$).

To detect binding of peptides to MHC class I H2Kb molecules on various murine cells, the cells were cultured as previously described and treated for various times as indicated in results and figure legends. Cells were centrifuged and washed using cold FACS buffer (DPBS with 5% FBS, 2 mM EDTA, 0.1% sodium azide). Cells were blocked using the bioLegend™ Fc block cat. no. 101320) for 10 min to 15 min to inhibit non-specific binding, followed by staining with fluorophore-conjugated antibody PE-labeled anti-MHC I/SIINFEKL (clone 25-D1.16; Invitrogen™, Thermo Fisher Scientific Inc., Waltham, MA; cat. no. 12-5743-82), for 30 min at 4° C. After washing, the cells were subjected to flow cytometric analysis with the Attune NXT Flow Cytometer (Invitrogen™). Cells were gated based on live single-cell populations and positives were assessed using isotype controls and fluor-minus-one analysis when needed. Data were analyzed using the Attune NXT software or FlowJo versions 10.7 and 10.8.

To evaluate the potential of BzFβ to enhance peptide loading under conditions used to prepare DC vaccines, $1\times10^6$ DC2.4 cells were pretreated with 50 μg/mL BzFß for 1 h in a total volume of 200 μL OptiMEM, then pulsed for 1 h with concentrations of SIINFEKL (1-10 μg/mL) often used for the in vitro production of DC vaccines. The cells were then stained for 30 min in 200 μL HBSS/2% FCS containing 0.4 μg PE-labeled MHC class I/SIINFEKL specific antibody, 25-D1.16. The cells were then examined using flow cytometry which revealed significant enhancement of peptide binding at all three doses of BzFβ, seen in FIG. 7. These results demonstrate the significant ability of BzFβ to enhance binding of peptide to MHC class I on the surface of APC, which leads to enhanced antigen presentation to and activation of the CD8+ T cell hybridoma, B3Z.

Example 4: Effects of BzFβ on Antigen Cross-Presentation by DC2.4 and Primary Splenocytes BzFβ was analyzed to determine if the compound could be affecting cross-presentation. To this end, DC2.4 cells were analyzed with OVA and SIINFEKL (SEQ ID NO: 1). It has been shown that the whole OVA enters the cell primarily through the mannose receptor and is then digested through proteasome degradation, prepared through the endoplasmic reticulum and Golgi, or via endosomal processing prior to the resulting peptide fragments being presented on the cell surface. (Blum, et al., Pathways of antigen processing. Ann Rev Immunol. 2013; 31:443-73; Belizaire & Unanue, Targeting proteins to distinct subcellular compartments reveals unique requirements for MHC class I and II presentation. Proc Natl Acad Sci USA. 2009 Oct. 13;106 (41): 17463-8). In contrast, the exogenously supplied SIINFEKL peptide can passively bind the cell surface MHC class I; therefore, does not need to enter the intracellular processing pathway. However, it has been reported that a small amount of SIINFEKL does enter the cell and is presented through canonical MHC class I presentation. (Day, et al., Direct delivery of exogenous MHC class I molecule-binding oligopeptides to the endoplasmic reticulum of viable cells. Proc Natl Acad Sci USA. 1997 Jul. 22;94 (15): 8064-9; Spiliotis, et al., Selective export of MHC class I molecules from the ER after their dissociation from TAP. Immunity. 2000 December; 13 (6): 841-51).

DC2.4 cells, provided by Dr. Kenneth Rock (University of Massachusetts) and B16F10 (CRL-6475; American Type Culture Collection (ATCC); cat. no. CRL-6475), were routinely cultured in complete Dulbecco's Modified Eagle Medium (cDMEM) containing 4500 mg/mL glucose (Gibco™, cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems cat. no. 11150H) at 37° C. in an atmosphere containing 5% $CO_2$ and 95% humidity. B3Z.A3 cells, provided by Dr. Nilabh Shastri (University of California Berkeley, Office of Technology Licensing), were cultured in RPMI 1640+GlutaMAX-1 (Gibco™, Cat. No. 61870-036) containing 2000 mg/mL glucose and supplemented with 40 μM 2-mercaptoethanol (B-Me) and 1 mM sodium pyruvate (Gibco™, cat. no. 11360-070). Murine splenocytes were cultured in complete RPMI (cRPMI) comprised of RPMI 1640+GlutaMAX-1 (Gibco™, Cat. No. 61870-036) containing 2000 mg/mL glucose and supplemented with 40 μM 2-mercaptoethanol. All culture media included 50 units/mL penicillin and 50 μg/mL streptomycin and 10% by volume heat inactivated fetal bovine serum (FBS) (Atlanta Biologicals S12450H). Cells were cultured at 37° C., in an atmosphere containing 5% $CO_2$ and 95% humidity.

BzFβ ((2E)-3-(1-benzofuran-5-yl) prop-2-eonic acid) (CAS no. 1210059-73-6, cat. no. CSSB00016286531) (SMILES OC(=O)/C=C\clccc2c (c1) cco2) was purchased from Chemspace (Monmouth Junction, NJ). Chicken ovalbumin (OVA, grade V) was purchased from Sigma (cat. no. A5503). Glycyl-L-leucine (cat. no. G0181) was purchased from TCI America (Portland, OR).

DC2.4 cells ($5\times10^5$ cells/ml) were seeded at 100 μL/well in 96 well plates and cultured overnight. The cells were washed with DPBS, and co-exposed to 0.5 mg/mL soluble whole OVA, along with increasing concentrations of BzFβ for 6 h, The cells were then co-cultured with equal number of B3Z cells at 37° C. for 19 h. Co-treatment of DC2.4 with increasing amounts of BzFβ and 0.5 mg/mL of OVA for 6 h were found to significantly enhance the B3Z response, seen in FIG. 8 ($p<0.001$ for all doses tested).

Murine splenocytes were plated at a density of 2.5 or $5\times10^4$ cells/well (100 μL/well in 96 well plates) and cultured overnight in cRPMI. The cells were washed with DPBS and then treated for 1-24 h with the indicated concentrations of BzFβ or co-treated with the indicated concentrations of BzFβ and 0.5 mg/mL OVA, suspended in complete media. Cells treated with BzFβ only were pulsed with 0.5 nM SIINFEKL pulsed for 1 h. The cells were then co-cultured with equal number of B3Z cells at 37° C. for 19 h. Co-treatment of murine splenocytes with increasing concentrations of BzFβ and 0.5 mg/mL OVA for 24 h enhanced their ability to activate B3Z, as seen in FIG. 9 ($p<0.0001$ for doses >6.25 μg/mL). Likewise, pre-treatment of murine splenocytes for 24 h with increasing concentrations of BzFβ, followed by pulsing them with 0.5 nM SIINFEKL for 1 h also enhanced their ability to activate the B3Z, seen in FIG. 9 ($p<0.0001$ for doses >12.5 μg/mL).

These observations suggest that BzFβ might either be affecting some aspects of cross-presentation, or more likely, stabilizing the surface expression of the MHC class I/peptide complex. This experiment was repeated using the murine melanoma cell line, B16F10, as the APC.

B16F10 were plated at a density of 2.5 or $5\times10^4$ cells/well (100 μL/well in 96 well plates) and cultured overnight in cDMEM. The cells were washed with DPBS and then treated for 1-24 h with the indicated concentrations of BzFβ or co-treated with the indicated concentrations of BzFβ and 1.0 mg/mL OVA, suspended in complete media. Cells treated with BzFβ only were pulsed with 2 nM SIINFEKL pulsed for 1 h. The cells were then co-cultured with equal number of B3Z cells at 37° C. for 19 h.

Since these cells lack the machinery for cross-presentation (Madden, The three-dimensional structure of peptide-MHC complexes. Ann Rev Immunol. 1995;13 (1): 587-622), it was not surprising that co-treatment with BzFβ and 1 mg/mL OVA failed to activate the B3Z cells. However, since they express adequate levels of surface MHC class I H-2Kb, they were able to significantly activate B3Z following pre-treatment with BzFβ and a 1 h pulse with 2 nM SIINFEKL, as seen in FIG. 10 (25 μg $p=0.0190$, 50 μg $p=0.0017$).

In this experiment the activity of the dipeptide, GL, was also examined, as it has been previously reported to function as a peptide exchange factor. (Saini, et al., Dipeptides catalyze rapid peptide exchange on MHC class I molecules. Proc Natl Acad Sci USA. 2015 Jan. 6;112 (1): 202-7; Saini, et al., Empty peptide-receptive MHC class I molecules for efficient detection of antigen-specific T cells. Sci Immunol. 2019 Jul. 19;4 (37): eaau9039). B16F10 were plated at a density of 2.5 or $5\times10^4$ cells/well (100 μL/well in 96 well plates) and cultured overnight in cDMEM. The cells were washed with DPBS and then co-treated for 24 h with 10 mM (1.88 mg/mL) of GL and 1.0 mg/mL OVA or were pulsed with 2 nM SIINFEKL for 1h following treatment with 10 mM GL in complete media. The cells were then co-cultured with an equal number of B3Z cells at 37° C. for 19 h.

Like BzFβ, GL had no effect on the uptake or processing of OVA but was able to significantly enhance B3Z activation by SIINFEKL pulsed splenocytes, as seen in FIG. 10 ($p=0.0013$).

To further investigate the potential role of cross-presentation in BzFβ's ability to enhance the B3Z response, cells were exposed to various cellular pathway inhibitor molecules. A list of the small molecule inhibitors used in the assessment of BzFβ's mechanism of action is summarized in Table 1. The cytotoxicity of all inhibitors was assessed using CellTiter96 Aqueous One (Promega (Madison WI, USA); cat. no. G3580).

Briefly, doses of inhibitor, found to be nontoxic and within the range of activity, were applied to DC2.4 in 100 μL cDMEM 1h prior to cotreatment with BzFβ. Mitomycin C (MMC) was applied to cells 30 min prior to BzFβ addition. The cells were then washed 2× before addition of BzFβ. Cells exposed to the other inhibitors were incubated with an appropriate concentration of each inhibitor, seen in Table 1 in cDMEM at 37° C., 5% $CO_2$. After a 1 h pretreatment with the other inhibitors, 100 μL of a 2× solution containing 50 μg/mL BzFβ (final concentration of 25 μg/mL) or vehicle control, with or without 0.5 mg/mL OVA, was added to each well. Cells were then incubated for 6 h. Before B3Z addition the inhibitor and BzFβ were removed, and the cells washed with warm DPBS. If testing peptide presentation, the DC2.4 cells were pulsed with 0.5 nM SIINFEKL for 1 h prior to being cocultured with B3Z.

TABLE 1

| List of Small Molecule Inhibitors | | | | | |
|---|---|---|---|---|---|
| Inhibitor Target | Compound Identifier | CAS No. | Source | Product ID | Conc. |
| NF-κB | Bay11 | 19542-67-7 | Cayman | 14795 | 5-10 μM |
| NF-κB | Dexamethasone | 50-02-2 | Cayman | 20340 | 2 μM |
| NF-κB | RO106-9920 | 62645-28-7 | Cayman | 15373 | 5-8 μM |
| Iκ Kinase | TPCA-1 | 507475-17-4 | Fisher Sci | NC1561402 | 50 nM |
| ERK | FR180204 | 865362-74-9 | Cayman | 15544 | 5 μM |
| ERK | SCH722984 | 942183-80-4 | Cayman | 19166 | 1.25 μM |
| mTOR | Torin 1 | 1222998-36-8 | Cayman | 10997 | 250 nM |
| mTOR | Rapamycin | 53123-88-9 | Sigma | 553211 | 5 nM |
| AP-1 | SR11302 | 160162-42-5 | Cayman | 16338 | 25 μM |
| Protein Transport | Brefeldin A | 20350-15-6 | Sigma | B6542 | 3 μg/mL |
| Endosome acidification | Bafilomycin A1 | 88899-55-2 | Cayman | 11038 | 100 nM |
| Endocytosis† | Cytochalasin D | 22144-77-0 | Fisher Sci | NC9996786 | 0.5 μM |
| Autophagy‡ | 3-Methyladenine | 5142-23-4 | Cayman | 13242 | 2.5 mM |
| Endosome acidification | Chloroquine | 54-05-7 | Sigma | C6628 | 4.32 μM |
| Translation | Cycloheximide | 66-81-9 | Sigma | C1988 | 15-30 ng/mL |
| Transcription | Doxorubicin | 23214-92-8 | Santa Clara Biotech | SC-280681 | 100 nM |
| Cell cycle | Mitomycin C | 50-07-7 | Sigma | M4287 | 30 μg/mL |

†Eisen, et al., Promiscuous binding of extracellular peptides to cell surface class I MHC protein. Proc Natl Acad Sci USA. 2012 Mar. 20; 109(12): 4580-5.
‡Wu, et al., Dual role of 3-methyladenine in modulation of autophagy via different temporal patterns of inhibition on class I and III phosphoinositide 3-kinase. J Biol Chem. 2010 Apr. 2; 285(14): 10850-61.

DC2.4 cells were pretreated for 1 h with 3 μg/mL BFA, a specific inhibitor of exocytosis and the intracellular transport of newly synthesized class I molecules as described above, then treated for 6 h with 25 μg/mL BzFβ and pulsed with 0.5 nM SIINFEKL or 0.5 mg/mL OVA As anticipated, B3Z activation using OVA as the antigen source was significantly suppressed by BFA while B3Z activation using DC2.4 cells treated with BzFβ and the exogenously supplied SIINFEKL peptide was unaffected, as seen in FIG. 11. The finding that BFA treatment suppressed B3Z activation by DC2.4 that had been pulsed with peptide alone (NoTx), suggests BzFβ's primary mechanism of action involves an ability to extracellularly stabilize surface expression of peptide bound MHC class I complexes. The response to GL was similar to that produced by BzFβ.

Continued interrogation of the effects of BzFβ on cross-presentation utilized DC2.4 treated with a number of small molecule inhibitors known to disrupt the conventional cross-presentation pathway, seen in Table 1, was undertaken similar to that of BFA. Bafilomycin A1 and chloroquine inhibit endosomal acidification, cytochalasin D inhibits endocytosis, 3-methyladenine inhibits autophagy, cycloheximide inhibits translation, and doxorubicin inhibits transcription. All of these inhibitors failed to inhibit the ability of BzFβ to enhance B3Z activation by DC2.4 pulsed with the exogenously supplied peptide, SIINFEKL (data not shown). Since these inhibitors work on nearly every part of the cross-presentation pathway, their inability to significantly affect the magnitude of B3Z activation by the DC2.4 cells treated with BzFβ and SIINFEKL supports the hypothesis that BzFß works extracellularly.

Together these data strongly suggest that BzFβ's primary mechanism of action is based on its ability to affect peptide binding to the surface expressed MHC class I complex. However, it does not completely rule out any effects on the intracellular mechanisms of cross-presentation.

Example 5: The Effect of BzFβ is not Due to Modulation of MHC Class I Expression To examine the potential effects of BzFβ on the surface expression of the MHC class I complex, the abundance and stability of MHC I H-2Kb was measured via flow cytometry.

The DC2.4, provided by Dr. Kenneth Rock (University of Massachusetts) and the IMG cell line (Millipore™, Merck KGaA, Burlington, MA; cat. no. SC-C134) were routinely cultured in complete Dulbecco's Modified Eagle Medium (cDMEM) containing 4500 mg/mL glucose (Gibco™, cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems cat. no. 11150H) at 37° C. in an atmosphere containing 5% $CO_2$ and 95% humidity.

The B3Z.A3 cell line was provided by Dr. Nilabh Shastri (University of California Berkeley, Office of Technology Licensing) while E.G7-OVA (CRL-2113) and THP-1 (TIB-202) cells were purchased from ATCC. These cells were cultured in RPMI 1640+GlutaMAX-1 (Gibco™, Cat. No. 61870-036) containing 2000 mg/mL glucose and supplemented with 40 μM 2-mercaptoethanol (B-Me) and 1 mM sodium pyruvate (Gibco™, cat. no. 11360-070). Murine splenocytes were cultured in complete RPMI (cRPMI) comprised of RPMI 1640+GlutaMAX-1 (Gibco™, Cat. No. 61870-036) containing 2000 mg/mL glucose and supplemented with 40 μM 2-mercaptoethanol. All culture media included 50 units/mL penicillin and 50 μg/mL streptomycin and 10% by volume heat inactivated fetal bovine serum (FBS) (Atlanta Biologicals S12450H). Cells were cultured at 37° C., in an atmosphere containing 5% $CO_2$ and 95% humidity.

BzFβ ((2E)-3-(1-benzofuran-5-yl) prop-2-eonic acid) (CAS no. 1210059-73-6, cat. no. CSSB00016286531) (SMILES OC(=O)/C=C\c1ccc2c(c1)cco2) was purchased from Chemspace (Monmouth Junction, NJ). Chicken ovalbumin (OVA, grade V) was purchased from Sigma (cat. no.

A5503). Glycyl-L-leucine (GL; TCI America, Tokyo Chemical Industry Co., Ltd. (Portland, OR); cat. no. G0181).

By using an MHC class I H-2Kb specific antibody, a relative comparison of the surface MHC class I was measured before and after BzFβ treatment of DC2.4 and IMG cells. These cells were treated with 25 μg/mL BzFβ for 0-4 h. Cells were centrifuged and washed using cold FACS buffer (DPBS with 5% FBS, 2 mM EDTA, 0.1% sodium azide). Cells were blocked with Fc block (bioLegend™; cat. no. 101320) for 10 min to 15 min to inhibit non-specific binding, followed by staining with fluorophore-conjugated antibodies; one set of cells was stained with the PE-labeled MHC/SIINFEKL specific antibody (clone 25-D1.16, Invitrogen™, Thermo Fisher Scientific Inc., Waltham, MA; cat. no. 12-5743-82), and the other set was stained with the PE-labeled MHC class I H-2Kb specific antibody (AF6-88.5.5.3, Invitrogen™, Thermo Fisher Scientific Inc., Waltham, MA; cat. no. 12-5958-82) PE-labeled MHC class I H-2 kb specific (clone AF6-88.5.5.3; Invitrogen™, Thermo Fisher Scientific Inc., Waltham, MA; cat. no. 12-5958-82), for 30 min at 4° C. After washing, the cells were subjected to flow cytometric analysis with the Attune NXT Flow Cytometer (Invitrogen™). Cells were gated based on live single-cell populations and positives were assessed using isotype controls and fluor-minus-one analysis when needed. Data were analyzed using the Attune NxT software or FlowJo versions 10.7 and 10.8.

Cells stained with the PE-labeled MHC/SIINFEKL specific antibody (clone 25-D1.16, (Invitrogen™, Thermo Fisher Scientific Inc., Waltham, MA; cat. no. 12-5743-81) demonstrate the enhancement of peptide binding by BzFβ, seen in FIGS. 12A and 13A, while the PE-labeled MHC class I H-2Kb specific antibody (AF6-88.5.5.3) determines if BzFβ, in the absence of exogenous peptide was affecting the levels of surface expressed MHC class I, as seen in FIGS. 12B and 13B. While BzFβ was able to enhance the binding of SIINFEKL to the surface MHC class I of both DC2.4 and IMG cells, flow cytometric analysis of these cells revealed no significant effect of BzFβ on the overall surface expression (MFI) of MHC class I between 1-4 h, but a significant increase was observed in cells treated for 24 h, seen in FIGS. 12A and 13A.

To determine if BzFβ affects synthesis or cycling of the MHC class I molecules, the class I molecule/peptide complexes were stripped from the surface of DC2.4 cells using a citric acid buffer, then treated with 25 μg/mL BzFβ, 5 mM of the dipeptide GL, or 3 μg/mL BFA (see Example 4) as a negative control.

An acid wash to strip the cell surface of MHC class I was performed as described with modifications. (Montealegre, et al., Dissociation of B2-microglobulin determines the surface quality control of major histocompatibility complex class I molecules. FASEB. 2015 July; 29 (7): 2780-8). DC2.4 were incubated overnight at 37° C. at $1\times10^5$. Cells were washed for 2 min in acidic buffer [(pH 2.5) 465 mM Citric acid, 35 mM sodium citrate, in PBS with 1% v/v FBS] or neutral buffer [(pH 7.4) PBS with 1% v/v FBS]. Afterwards the pH was neutralized by the addition of cDMEM. The cells were washed with PBS and treated with BzFβ or GL in cDMEM for various times to allow for MHC class I recovery at 37° C. Cells were washed and stained with an H-2Kb-specific antibody (Invitrogen™, cat. no. 12-5958-82) and analyzed by flow cytometry as described previously MHC I recovery on the cell surface at various time points was detected by flow cytometry using the PE-labeled MHC class I H-2Kb specific antibody (AF6-88.5.5.3). Cells treated with BzFβ post-stripping did not show an increase in MHC class I recovery as compared to vehicle control when treated for 4-24 h. At 6 hours >60% of the MHC class I molecules recovered, seen in FIG. 14. When DC2.4 cells were exposed to the same acid stripping protocol and then used in the B3Z assay, it was observed that BzFβ was still able to increase the B3Z response post acid-stripping when the cells were treated during recovery (data not shown). This data suggests that BzFβ works to stabilize existing MHC class I complexes rather than enhancing the production of new ones, and further confirms that BzFβ increases peptide binding irrespective of the class I molecule abundance.

The relative kinetic stability or off-rate of the SIINFEKL peptide (SEQ ID NO: 1) was determined using the BFA decay experiment as previously described. (Boulanger, et al., The B3Z.A3 cell line was provided by Dr. Nilabh Shastri (University of California Berkeley, Office of Technology Licensing) while E.G7-OVA (CRL-2113) and THP-1 (TIB-202) cells were purchased from ATCC. These cells were cultured in RPMI 1640+GlutaMAX-1 (Gibco™, Cat. No. 61870-036) containing 2000 mg/mL glucose and supplemented with 40 μM 2-mercaptoethanol (B-Me) and 1 mM sodium pyruvate (Gibco™, cat. no. 11360-070). Murine splenocytes were cultured in complete RPMI (cRPMI) comprised of RPMI 1640+GlutaMAX-1 (Gibco™, Cat. No. 61870-036) containing 2000 mg/mL glucose and supplemented with 40 μM 2-mercaptoethanol. All culture media included 50 units/mL penicillin and 50 μg/mL streptomycin and 10% by volume heat inactivated fetal bovine serum (FBS) (Atlanta Biologicals S12450H). Cells were cultured at 37° C., in an atmosphere containing 5% $CO_2$ and 95% humidity.

BzFβ ((2E)-3-(1-benzofuran-5-yl) prop-2-eonic acid) (CAS no. 1210059-73-6, cat. no. CSSB00016286531) (SMILES OC(=O)/C=C\c1ccc2c(c1)cco2) (Chemspace, Monmouth Junction, NJ), 3 chlorophenol red-β-D-galactopyranoside (CPRG, cat. no. 10884308001) were purchased from Sigma Chemical Co (St. Louis, MO). CPRG stock was prepared to 175 μg/mL in sterile $H_2O$ and a working solution of 1.75 μg/mL was used. Vaccine grade high molecular weight polyinosinic-polycytidylic acid (Poly (I: C) (cat. no. VPIC-264) and ultrapure LPS, *E. coli* 0111: B4 were obtained from InvivoGen (cat. no. tlrl-3pelps).

Chicken ovalbumin (OVA, grade V) was purchased from Sigma (cat. no. A5503). The H-2 $D^b$ binding peptide, HPV E749-57 (AnaSpec Inc., Fremont, CA; cat. no.AS-61022) and the H-2$K^b$ $OVA_{257-264}$ peptide, SIINFEKL (AnaSpec Inc., Fremont, CA; cat. no. AS-60193-1; SEQ ID NO: 1). The Trp2 (tyrosinase-related protein 2) peptide ($SVYDFFVWL_{180-188}$; (SEQ ID NO: 2) was modified at AnaSpec Inc. by replacing the Trp (W) with a lysine (K) containing an attached molecule of FITC (SVYDFFVK (FITC) L; SEQ ID NO: 3). The HPV E749-57 peptide RAHYNIVTF (SEQ ID NO: 4), modified at the N-terminus by labeling with FITC, was purchased from AnaSpec Inc. (cat. no. SQ-ASPE-77874). Glycyl-L-leucine (GL; TCI America, Tokyo Chemical Industry Co., Ltd. (Portland, OR); cat. no. G0181).

Activation of B3Z T cell hybridoma cells was assessed following their exposure to various MHC class I H-2$K^b$ positive cell lines presenting the SIINFEKL peptide. To stimulate β-gal production in the B3Z, the H-2Kb murine cell lines, DC2.4 and E.G7-OVA were plated at a density of 2.5 or $5\times10^4$ cells/well (100 μL/well in 96 well plates) and cultured overnight at 37° C. in an atmosphere containing 5% $CO_2$ and 95% humidity. The cells were washed with DPBS and then treated for 1-24 h with the indicated concentrations of BzFβ suspended in complete media. Vehicle controls were always included. Cells being examined for the uptake and processing of soluble OVA were co-treated with BzFβ and 0.5 mg/mL grade V chicken ovalbumin for 6-24 h, and then washed and cocultured with B3Z as indicated.

Following the pretreatment with BzFβ, the media was removed from adherent cells (DC2.4 or B16F10) or was removed following pelleting of nonadherent cells in the plate. The cells were then pulsed with various concentrations of SIINFEKL peptide (typically 0.5 nM was used) for the indicated lengths of time (typically 1 h). The cells were washed and then 100 μL of complete DMEM containing $5\times10^4$ B3Z cells was added. The co-culture was incubated at 37° C. for 19 h to allow for B3Z activation. To detect activation of the B3Z cells, the media was removed and 100 μL of 250 μM CPRG reconstituted in the lysis buffer (1× DPBS, 0.2% v/v saponin, 20 mM magnesium chloride) was added directly to each well. Cells were maintained at 37° C. prior to measurement. The absorbance at 560 nm (700 nm for background) was intermittently monitored using a BioTek Synergy HTX multimode microplate reader (Winooski, VT) to detect β-gal activity. CPRG lysis buffer and B3Z cells only served as the negative controls. All treatments were performed in triplicate and all experiments were repeated a minimum of three times.

For peptide loading studies, cultured cells were treated for various times as indicated in results and figure legends. Cells were centrifuged and washed using cold FACS buffer (DPBS with 5% FBS, 2 mM EDTA, 0.1% sodium azide). Cells were blocked using Fc block (bioLegend™; cat. no. 101320) for 10 min to 15 min to inhibit non-specific binding, followed by staining with fluorophore-conjugated antibody PE-labeled anti-MHC I/SIINFEKL (clone 25-D1.16, Invitrogen™ 12-5743-82), for 30 min at 4° C. For N-terminal FITC labeled H-2 Db peptide RAHYNIVTF (AnaSpec Inc., Fremont, CA; cat. no.; SEQ ID NO: 4) cells were incubated with peptide for 1-4 h before washing and analysis. After washing, the cells were subjected to flow cytometric analysis with the Attune NxT Flow Cytometer (Invitrogen™). Cells were gated based on live single-cell populations and positives were assessed using isotype controls and fluor-minus-one analysis when needed. Data were analyzed using the Attune NxT software or FlowJo versions 10.7 and 10.8.

Interestingly, while pre-treatment with BzFβ showed no effects on kinetic stability of the SIINFEKL-MHC class I complex, when BzFβ was provided post-peptide addition, a significantly greater loss of the surface complex was observed. Treatment of DC2.4 cells with 25 μg/mL BzFβ or 5 mM GL following a 1 h peptide pulse (30 nM SIINFEKL) significantly reduced the MHCI/SIINFEKL complex staining when compared to the untreated cells, as seen in FIG. 16 ($p<0.0001$, $p=0.0027$, respectively).

The apparent ability of BzFβ to enhance turnover of preexisting, high affinity, MHC class I bound peptides could allow for the targeted binding of more appropriate or clinically desirable peptides to a variety of cells, including immune cells or tumor cells. Evidence supporting this hypothesis was obtained by examining BzFβ's ability to affect E.G7-OVA cells activation of B3Z cells. E.G7-OVA is a murine H-2Kb+ cell line expressing OVA endogenously and able to generate and present bound to MHC class I, the SIINFEKL peptide, as seen in FIG. 17A. Treatment of these cells with increasing concentrations of BzFβ (0-100 μg/mL), dose-dependently reduced the ability of these cells to activate B3Z, as seen in FIG. 17B. This effect was significant at a dose as low as 6.25 μg/mL.

Example 7: BzFβ Enhances Peptide Binding to H-2 db MHC Class I and HLA-A*02:01

DC2.4 are a C57Bl/6 lineage murine cell line and as such they express MHC class I H-2Kb and H-2 Db. These two alleles exhibit slightly different requirements for peptide binding. H-2Kb favors a bulkier hydrophobic residue at position five (Tyr, Phe), while H-2 Db favors a hydrophilic residue at position five (Asn). Tyrosine or proline is preferred by H-2 Db at position three. Both alleles prefer a hydrophobic residue (Met, Ile, Leu or Val) at the C-terminus to interact with the F pocket of the MHC class I binding groove. The H-2 Db requires the peptide to arch out between residues 6 and 7 for interaction with the T cell receptor, and as such requires peptides to have a length of at least nine residues. In H-2Kb this region is deeper and favors binding to peptides that are 8 residues in length. (Reynisson, eta al., NetMHCpan-4.1 and NetMHCIIpan-4.0: improved predictions of MHC antigen presentation by concurrent motif deconvolution and integration of MS MHC eluted ligand data. Nucleic Acids Res. 2020 Jul. 2;48 (W1): W449-W5422).

DC2.4 cells (Dr. Kenneth Rock, University of Massachusetts) and IMG cell line (Millipore™, Merck KGaA, Burlington, MA; cat. no. SC-C134) were cultured in cDMEM containing 4500 mg/mL glucose supplemented with GlutaMAX, 50 U/mL penicillin and 50 μg/mL streptomycin, and FBS, as outlined in more detail in Example 3.

Cells were cultured as previously described and treated for various times as indicated in results and figure legends. Cells were centrifuged and washed using cold FACS buffer (DPBS with 5% FBS, 2 mM EDTA, 0.1% sodium azide). Cells were stained with N-terminal fluorophore-conjugated antibodies FITC labeled Trp2180-188 peptide (SVYDFFVWL; SEQ ID NO: 2) and N-terminal FITC labeled H-2 Db peptide RAHYNIVTF (Anaspec, Inc.; SEQ ID NO: 4) cells were incubated with Fc block (bioLegend™; cat. no. 101320) for 10 min to 15 min to inhibit non-specific binding, followed by peptide for 1-4 h, before washing and analysis. After washing, the cells were subjected to flow cytometric analysis with the Attune NxT Flow Cytometer (Invitrogen™). Cells were gated based on live single-cell populations and positives were assessed using isotype controls and fluor-minus-one analysis when needed. Data were analyzed using the Attune NXT software or FlowJo versions 10.7 and 10.8.

While H-2Kb is the dominant haplotype, BzFβ was investigated to determine if the compound could assist peptide binding on H-2Kb and H-2 Db. Using the N-terminal FITC labeled Trp2180-188 peptide (SVYDFFVWL; SEQ ID NO: 2) and the N-terminal FITC labeled HPV49-57 peptide (RAHYNIVTF; SEQ ID NO: 4) that bind with high affinity to H-2Kb and H-2 Db, respectively, BzFβ was found to enhance peptide binding on both haplotypes, seen in FIGS. 18 and 19. This demonstrates that the phenomenon is not solely restricted to binding of the SIINFEKL peptide (SEQ ID NO: 1).

A tetramer quick switch assay was performed according to manufacturer's instructions for flow cytometric analysis using both the QuickSwitch Quant HLA-A*02:01 tetramer Kit (MBL International Corporation TB-7300-K1) and the H-2Kb kit (TB-7400-K2). The abilities of MBL's proprietary peptide exchange factor (unknown concentration), 1 mM of the glycl-leucine dipeptide, was compared to 1 mM of BzFβ to promote peptide exchange. The QuickSwitch assay utilizes an antibody specific for an irrelevant exchangeable low affinity "exiting peptide" to quantify its removal from an MHC class I tetramer and replacement with a higher affinity peptide of choice. All volumes and concentrations were as instructed in the protocol provided. Briefly, the given reference peptide was mixed with the QuickSwitch tetramer, then the kit's peptide exchange factor, BzFβ, or GL were added in the volumes described in the manufacturer's protocol. With the aim of comparing the molecule's peptide exchange rate, peptide exchange was measured at various timepoints. The tetramer-peptide-molecule mix was maintained at 25° C. in the dark, and 5 μL of the sample was removed at each time point. This mixture was added to the supplied magnetic capture beads and shaken in the dark for 45 min at 25° C. After this, the sample was washed with a 1× assay buffer and FITC-labeled exiting peptide antibody was added to the mixture and the incubation was repeated. After washing, each sample was analyzed by flow cytometry. The percent of peptide exchange was calculated using the online QuickSwitch Quant-Peptide-Exchange-Calculator (MBL Int'l Corp., Woburn, MA) to compare peptide exchange over time.

This peptide exchange reaction is catalyzed by the presence of an "exchange factor" which they supply with the kit, as seen in FIG. 20A. When BzFβ and GL were used in place of their proprietary exchange factor, it was discovered that nearly all (99%) of the exiting peptide bound to the MHC class I H-2Kb tetramer had been displaced by 30 min. The kit supplied exchange factor required 2 h to exchange >90% of the peptide and 4 h to produce the same level of exchange achieved with BzFβ, seen in FIG. 20B.

When 1 mM BzFβ and GL were used in place of the kit's exchange factor, along with the HLA-A*02:01 tetramer, >90% exchange was achieved within 30 min, but 4 h was required to exchange 96% of the test peptide. The proprietary exchange factor was able to exchange 99% of the test peptide within 2 h, as seen in FIG. 20C. Compared to exchange in the absence of exchange factor, BzFβ was significantly able to increase peptide turnover on both murine and human class I complexes ($p<0.001$), seen in FIGS. 20A through 20C, but like GL, it appeared to be more efficient with HLA A*02:01. These results demonstrate that BzFβ is not only facilitating rapid peptide turnover, but rather peptide exchange on MHC class I complexes already bound with peptide.

Example 8: Molecular Docking Predicts BzFβ Interaction with the MHC Class I F Pocket The crystal structure of H-2Kb in complex with high affinity peptide SIINFEKL (PDB ID: 3P9L) and the HLA A*02-01 with octomeric tax peptide (PDB ID: 3HLA) were obtained from the Protein Data Bank and served as starting structures for molecular docking analysis. Ligand structures were drawn using PubChem Sketcher v2.4, saved in the MDL molfile (sdf) format, and converted into the Sybyl Mol2 (mol2) PDB format using Open Babel GUI v3.1.1. The mol2 file was opened in AutoDock Tools v1.5.6 and converted into a ligand by adding gasteiger charges, merging nonpolar hydrogen atoms with their attached carbon atoms to form united atoms, and setting rotatable bonds. It was then saved in the PDBQT format. The grid box for each receptor was created to include the F-pocket with a spacing of 0.375 Å, followed by the docking of BzFβ to each receptor was initiated. The structural models were collected from the lowest-energy docking solutions of each receptor. The inhibition constant was calculated in AutoDock using the formula:

$$Ki = \exp(\Delta G \times 1000)/(Rcal \times TK)$$

where ΔG is the docking energy, Rcal is 1.98719, and TK is 298 (Iman, et al., Molecular docking analysis and molecular dynamics simulation study of ameltolide analogous as a sodium channel blocker. Turk J Chem. 2015;39 (2): 306-316).

Based on the observations that BzFβ's activity is similar to that described for dipeptide exchange factors like GL (Saini, et al., Dipeptides catalyze rapid peptide exchange on MHC class I molecules. Proc Natl Acad Sci USA. 2015 Jan. 6;112 (1): 202-7; Saini, et al., Empty peptide-receptive MHC class I molecules for efficient detection of antigen-specific T cells. Sci Immunol. 2019 Jul. 19;4 (37): eaau9039), computational molecular docking was utilized to determine if BzFβ is predicted to interact with the MHC class I and HLA-A peptide binding grooves in a manner described for the dipeptides. Using the AutoDock Suite to perform the docking studies (Morris, et al., AutoDock4 and AutoDockTools4: Automated docking with selective receptor flexibility. J Comput Chem. 2009 December; 30 (16): 2785-91), it was predicted that BzFβ interacts with the F pocket of the H-2K$^b$ MHC class I and HLA-A*02:01 peptide binding grooves in a manner similar to that described for the SIINFEKL peptide and the GL dipeptide. (Madden, The three-dimensional structure of peptide-MHC complexes. Ann Rev Immunol. 1995;13 (1): 587-622; Hein, et al., Peptide-independent stabilization of MHC class I molecules breaches cellular quality control. J Cell Sci. 2014 Jul. 1; 127 (13): 2885-97). In the top three predicted poses, the benzofuran portion of BzFβ is observed deep within the hydrophobic F pocket, while its carboxylic acid group is hydrogen-bonded to a key amino acid, Lys146, affecting conformation of the F pocket, as seen in FIGS. 21A through 22B.

Lys146 and Tyr84 are two amino acids that are conserved across all MHC class I and HLA-A, B, and C haplotypes and are believed to be universally involved in peptide binding and F pocket opening. (Remesh, et al., Unconventional peptide presentation by major histocompatibility complex (MHC) class I allele HLA-A* 02:01: BREAKING CONFINEMENT. J Biol Chem. 2017 Mar. 31;292 (13): 5262-70). Lys146 forms a partial lid above the F pocket that is held in position by the hydrogen bond interaction with the carboxyl terminus of the peptide. Lifting of Lys 146 opens the F pocket, especially in the presence of extended peptides with negatively charged residues near their carboxyl end. Tyr84 has been found to swing out in the presence of extended peptides with positive charges near their carboxyl end. This also allows for the opening of the F pocket. (Remesh, et al., Unconventional peptide presentation by major histocompatibility complex (MHC) class I allele HLA-A* 02:01: BREAKING CONFINEMENT. J Biol Chem. 2017 Mar. 31;292 (13): 5262-70). Therefore, the finding that BzFβ interacts with key amino acids on H-2K$^b$ and HLA-A02: 01 could explain its ability to stabilize the open conformation and displace previously bound peptides. Similar to BzFβ, the GL dipeptide and the C-terminal residue of SIINFEKL also form hydrogen bonds with Lys146, as well as with Tyr84. (Hein, et al., Peptide-independent stabilization of MHC class I molecules breaches cellular quality control. J Cell Sci. 2014 Jul. 1;127 (13): 2885-97).

When compared with the free energy of binding (binding affinity) predicted for GL binding in the F pocket of H-2K$^b$ (−6.20 kcal/mol) and HLA-A*02:01 (−6.71 kcal/mol), AutoDock predicted that BzFβ required similar free energy for binding to H-2$K^b$ (−5.54 kcal/mol) and HLA-A*02:01 (−5.36 kcal/mol), as seen in FIG. 23.

In the same simulations it can be seen that GL binds in a similar manner as BzFβ, forming a hydrogen bond with Lys146 and burying its hydrophobic region deep into the F pocket. These results show that like the GL dipeptide and the C-terminal amino acids of MHC class I peptides, BzFβ is predicted to interact with the F pocket of H-2$K^b$ and HLA-A*02:01 and potentially induce a change in conformation that is more receptive to exogenous full-length peptides.

Example 9: The Unique Structure of BzFβ is Critical to its Enhancement of the CD8+ T Cell Response The DC2.4 cell line was provided by Dr. Kenneth Rock (University of Massachusetts). These cell lines were routinely cultured in complete Dulbecco's Modified Eagle Medium (cDMEM) containing 4500 mg/mL glucose (Gibco™, cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems cat. no. 11150H) at 37° C. in an atmosphere containing 5% $CO_2$ and 95% humidity.

The B3Z.A3 cell line was provided by Dr. Nilabh Shastri (University of California Berkeley, Office of Technology Licensing) while E.G7-OVA (CRL-2113). These cells were cultured in RPMI 1640+GlutaMAX-1 (Gibco™, Cat. No. 61870-036) containing 2000 mg/mL glucose and supplemented with 40 μM 2-mercaptoethanol (B-Me) and 1 mM sodium pyruvate (Gibco™, cat. no. 11360-070). Murine splenocytes were cultured in complete RPMI (cRPMI) comprised of RPMI 1640+GlutaMAX-1 (Gibco™, Cat. No. 61870-036) containing 2000 mg/mL glucose and supplemented with 40 μM 2-mercaptoethanol. All culture media included 50 units/mL penicillin and 50 μg/mL streptomycin and 10% by volume heat inactivated fetal bovine serum (FBS) (Atlanta Biologicals S12450H). Cells were cultured at 37° C., in an atmosphere containing 5% $CO_2$ and 95% humidity.

TABLE 2

BzFβ analog molecules examined.

| Molecule Name | Abbreviation | Structure | Molecular Weight |
|---|---|---|---|
| (2E)-3-(1-benzofuran-5-yl)prop-2-enoic acid | BzFβ | 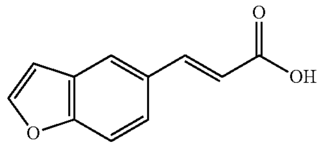 [SMILES: O=C(O)/C=C/c1ccc2occc2c1] | 188.18 |
| 3-(2,3-dihydro-1-benzofuran-5-yl)acrylic acid | Analog #2 | 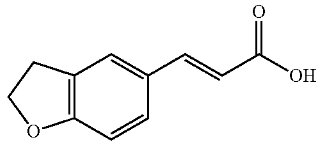 [SMILES: O=C(O)/C=C/c1ccc2c(c1)CCO2] | 190.20 |
| 3-(2,3-dihydrobenzofuran0-5-yl)propanoic acid | Analog #3 | 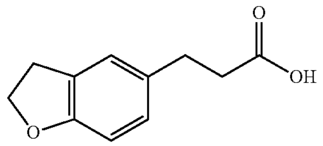 [SMILES: O=C(O)CCc1ccc2c(c1)CCO2] | 192.22 |
| (2E)-3-(1,3-benzodioxol-5yl)acrylic acid | Analog #4 | 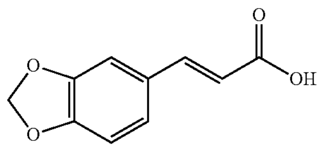 [SMILES: O=C(O)/C=C/c1ccc2c(c1)OCO2] | 192.17 |
| 4-(1-benzofuran-5-yl)butan-2-one | Analog #5 | 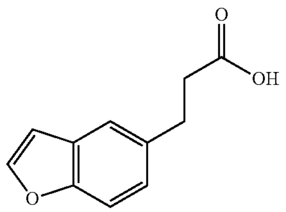 [SMILES: O=C(O)CCc1ccc2occc2c1] | 190.19 |

TABLE 2-continued

| BzFβ analog molecules examined. | | | |
|---|---|---|---|
| Molecule Name | Abbreviation | Structure | Molecular Weight |
| Glycine-leucine dipeptide | GL | 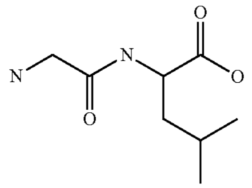 | 188.22 |

BzFβ ((2E)-3-(1-benzofuran-5-yl) prop-2-eonic acid) (CAS no. 1210059-73-6, cat. no. CSSB00016286531) (SMILES OC(=O)/C=C\c1ccc2c(c1)cco2) (Chemspace, Monmouth Junction, NJ), 3-(2,3-dihydro-1-benzofuran-5-yl) acrylic acid (Matrix Scientific, Columbia, SC; cat. no. 007326) and 3-(2,3-dihydrobenzofuran0-5-yl) propanoic acid (Matrix Scientific, Columbia, SC; cat. no. 007325), (2E)-3-(1,3-benzodioxol-5yl) acrylic acid (Sigma Chemical Co., St. Louis, MO; cat. no. 146242) and chlorophenol red-β-D-galactopyranoside (CPRG, Sigma Chemical Co., St. Louis, MO; cat. no. 10884308001) were purchased acquired as indicated. CPRG stock was prepared to 175 μg/mL in sterile $H_2O$ and a working solution of 1.75 μg/mL was used.

DC2.4 were plated at a density of 2.5 or $5\times10^4$ cells/well (100 μL/well in 96 well plates) and cultured overnight in cDMEM. The cells were washed with DPBS and then treated for 1-24 h with the indicated concentrations of BzFβ or an analog, seen in Table 2, suspended in complete media. Following the pretreatment with BzFß or an analog, seen in Table 2, the media was removed from adherent cells. The cells were then pulsed with various concentrations of SIINFEKL (SEQ ID NO: 1) peptide (typically 0.5 nM was used) for the indicated lengths of time (typically 1 h). The cells were washed and then 100 μL of complete DMEM containing $5\times10^4$ B3Z cells was added. The co-culture was incubated at 37° C. for 19 h to allow for B3Z activation.

To detect activation of the B3Z cells, the media was removed and 100 μL of 250 μM CPRG reconstituted in the lysis buffer (1× DPBS, 0.2% v/v saponin, 20 mM magnesium chloride) was added directly to each well. Cells were maintained at 37° C. prior to measurement. The absorbance at 560 nm (700 nm for background) was intermittently monitored using a BioTek Synergy HTX multimode microplate reader (Winooski, VT) to detect β-gal activity. CPRG lysis buffer and B3Z cells only served as the negative controls. All treatments were performed in triplicate and all experiments were repeated a minimum of three times.

To illuminate how the structure of BzFβ informs its ability to enhance peptide binding, a series of molecules differing from BzFβ by one or two structural modifications were obtained, as seen in Table 2. All of the analogs were tested at doses up to 50 g/mL (265 μM) and pulsed with 0.5 nM SIINFEKL. When compared to BzFβ, they all failed to enhance B3Z activation, as seen in FIGS. 24A through 24C. These analogs were further analyzed for their ability to increase SIINFEKL binding, as well as altering surface MHC class I abundance. Treatment of DC2.4 cells with 25 or 50 μg/mL of each analog for up to 24 h failed to enhance SIINFEKL peptide binding, seen in FIG. 25, and did not increase MHC class I abundance (data not shown). These molecules were then tested for the ability to displace the SIINFEKL peptide from the H-$2K^b$ complex on DC2.4 cells. Using the same conditions that had been used to test BzFβ, treatment with 25 μg/mL of each analog after a 1 h pulse with SIINFEKL did not enhance peptide displacement at any time point tested, as seen in FIG. 26. This limited examination of the structure activity relationship revealed the importance of the double bond in the furan for BzFβ activity.

Example 10: In Silico Assessment of BzFβ Shows Drug-Like Features

SwissADME, a component of a web-based suite of tools that utilizes a pool of predictive models for examining the physicochemical properties, pharmacokinetics, and drug-likeness of target molecules provided by the Swiss Institute of Bioinformatics (Ndombera, et al., Pharmacokinetic, physicochemical and medicinal properties of n-glycoside anti-cancer agent more potent than 2-deoxy-d-glucose in lung cancer cells. J Pharm Pharamcol. 2019; 7 (4): 165-76; Daina, et al., SwissADME: a free web tool to evaluate pharmacokinetics, drug-likeness and medicinal chemistry friendliness of small molecules. Sci Rep. 2017 Mar. 3;7 (1): 1-13), was used to predict the ADME profile of BzFβ. This database assesses the structure of the input molecule to inform the behavior of the molecule in vivo for characteristics such as: physicochemical properties, lipophilicity, water solubility, pharmacokinetics, synthetic accessibility, and drug-likeness. The structure of BzFβ was drawn using Chem Axons Marvin JS (Chemaxon Ltd., Budapest, Hungary) with 2D features.

Evaluation of BzFβ indicated it to be drug-like in four of the five rule-based filters, with the only violation being that its molecular weight is lower than 200 daltons. In addition, the software was used to evaluate a combination of molecular properties, determining if BzFβ is similar to already known drugs in electronic distribution, hydrophobicity, lipophilicity, solubility, polarity, level of conjugation, hydrogen bonding characteristics, molecular flexibility, and size. (Anjanappa, et al., Structures of peptide-free and partially loaded MHC class I molecules reveal mechanisms of peptide selection. Nat Commun. 2020 Mar. 11;11 (1): 1314). One of the most interesting predictions is that BzFβ has a high probability of being able to cross the blood brain barrier and/or be absorbed through the GI tract. If this is the case, examining BzFβ's therapeutic potential could be quite beneficial.

When structurally similar analogs of BzFβ were examined for physicochemical properties, lipophilicity, water solubility, pharmacokinetics, synthetic accessibility, and drug-likeness, BzFβ's lipophilicity (consensus LogPow), seen in FIG. 27A, the ratio of sp3 hybridized carbons over the total carbon count of the molecule (Fraction Csp3), seen in FIG. 27B, and water solubility, seen in FIG. 27C, separated BzFß from the non-active analogs that were tested. BzFβ, like the other 3 molecules is predicted to be approximately twice as soluble in n-octanol as it is in water (2.00, 1.81, 1.83, and 1.68 respectively). The distinguishing characteristic of BzFβ is its fraction of sp3 hybridized carbons. BzFβ possesses no saturated carbons (0 out of its 11 total carbons) while the analogs contain 0.18, 0.36, and 0.1 of their carbons possessing sp3 orbitals. This rigidness in structure and lipophilic nature of BzFβ could help explain its enhanced affinity for the hydrophobic region of the F pocket and the inability of the structurally similar analogs to affect peptide binding. Further work needs to be done to verify the importance of these properties.

Example 11: BzFβ can be Detected in the Blood for at Least 3 h Post-IV, -IM, or -Oral Administration Six-to ten-week-old male and female C57BL/6NCrl mice (Charles River Laboratories, Wilmington MA; cat. no. 027) were used for all animal studies. The mice were maintained in accord with the NIH Guide for the Care and Use of Laboratory Animals. Experimental procedures were performed in accord with research protocols approved by the Tampa Bay Research Institute's Institutional Animal Care and Use Committee. Mice were maintained in an INOVIVE individually ventilated cage system with 3 mice per cage containing 100% virgin wood pulp bedding (Harlan Teklad™, Harlan Sprague Dawley Inc., Indianapolis, IA; cat. no. 7099). Water and food (Harlan Teklad™, cat. no. 8640) were available ad libitum. The mice were maintained on a cycle of 12 h of light and 12 h of dark in an environment with a temperature of 74-76° C. and 40-60% humidity. All cages underwent 40 air changes hourly in the negative pressure mode, in accordance with manufacturer's recommendations. Both the intake and exhaust air from the system were filtered through HEPA filters to maintain a clean environment. Stock solutions of BzFβ were solubilized in alkaline water (pH 10) and then sterile filtered through 0.22 μm syringe filters. BzFβ used for iv or im injections was diluted in 0.9% saline (normal saline). The stock solutions of the SIINFEKL peptide (SEQ ID NO: 1) were prepared in 1× calcium/magnesium free Dulbecco's phosphate-buffered saline (DPBS; ThermoFisher Scientific, cat. no. 14190144).

BzFβ ((2E)-3-(1-benzofuran-5-yl) prop-2-eonic acid) (CAS no. 1210059-73-6, cat. no. CSSB00016286531) (SMILES OC(=O)/C=C\c1ccc2c(c1)cco2) was purchased from Chemspace (Monmouth Junction, NJ), 3-(2,3-dihydro-1-benzofuran-5-yl) acrylic acid (cat. no. 007326) and 3-(2, 3-dihydrobenzofuran0-5-yl) propanoic acid (cat. no. 007325) were purchased from Matrix Scientific (Columbia, SC).

After overnight fasting, six-to ten-week-old mice were gavaged with 1-2 mg of BzFβ solubilized in 200 μL alkaline water or were injected intramuscular (IM) or intravenous with 100 μg diluted in normal saline. After various times mice were anesthetized using 2.0% isoflurane with $O_2$ at 1 L/min, and 200-500 μL of blood was collected in a microfuge tube containing 700 μL of 50 mM EDTA in DPBS as an anticoagulant. The blood samples were centrifuged at 4500×g for 20 min to separate the plasma from the cells. The resulting plasma (200 μL) was removed and extracted with 4 mL methanol. This mixture was vortexed for 30 s and centrifuged at 4000×g for 10 min at 4° C. The supernatant was collected and dried using a SpeedVac (SC210A) under a vacuum of 0.4 torr at 65° C. When dry, the sample was removed and resuspended in 100 μL methanol and then re-centrifuged to remove any precipitates. A 20 μL sample of this mixture was analyzed by HPLC.

BzFβ was detected in the serum using a Shimadzu high performance liquid chromatography (HPLC) system. The Shimadzu system consisted of two LC-20AR pumps, a SPD-M20A diode array UV-Vis detector, and a 20 μL injection loop onto a Phenomenex Luna 5 μm Analytical PFP column 100 A (cat. no. 00F-4448-E0). Analysis and data collection were conducted using Shimadzu LabSolutions software. Samples (20 μL) were injected onto the column and separated using a gradient of acetonitrile (ACN) and water as the mobile phase. The gradient started with 10% ACN and increased stepwise to 80% ACN for peak clarity. Buffer B was water adjusted to pH 2.5 using phosphoric acid. The column was kept at a constant temperature of 30° C. (Chai, et al., Comprehensive study of the intestinal absorption of four phenolic compounds after oral administration of *Ananas comosus* leaf extract in vivo and in vitro. Afr J Pharm Pharmacol. 2013 Jul. 15;7 (26): 1781-92).

Following up on the prediction that BzFβ should be able to be absorbed through the GI tract and gain access to the systemic circulation, C57Bl/6crl mice were gavaged (po) with either 200 μL of alkaline water (negative control) or with 2 mg of BzFβ solubilized in 200 μL alkaline water. Fifteen minutes later, peripheral blood was obtained. The serum was extracted with methanol, lyophilized, and then examined by HPLC for the presence of BzFβ. Analysis of the HPLC chromatogram revealed the presence of BzFβ, as seen in FIG. 28A. BzFβ was then administered to another group of mice iv (100 μg), im (100 μg), and po (1 mg). After 15 min, the serum was collected, extracted with methanol, and then analyzed by HPLC. HPLC analysis revealed the presence of the appropriate peak in mice receiving BzFβ by each of the different routes of administration, as seen in FIG. 28B. The persistence of BzFβ within the peripheral blood was examined by sampling the serum 1, 2, and 3 h post im injection of 1 mg BzFβ that had been diluted in 50 μL normal saline. HPLC analysis revealed that while the serum levels of BzFβ were declining over the 3 h period, it was still detectable, as seen in FIG. 28C.

Example 12: Oral, Intravenous, or Intramuscular Administration of BzFβ Significantly Enhances the In Vivo Binding of an MHC I Peptide Having detected the presence of BzFβ in the serum of mice following administration via po, iv, and im delivery, BzFβ was analyzed to determine if the compound could enhance peptide loading in vivo.

Six-to ten-week-old male and female C57BL/6NCrl mice (Charles River Laboratories, Wilmington MA; cat. no. 027) were used for all animal studies. The mice were maintained in accord with the NIH Guide for the Care and Use of Laboratory Animals. Experimental procedures were performed in accord with research protocols approved by the Tampa Bay Research Institute's Institutional Animal Care and Use Committee. Mice were maintained in an INOVIVE individually ventilated cage system with 3 mice per cage containing 100% virgin wood pulp bedding (Harlan Teklad™, Harlan Sprague Dawley Inc., Indianapolis, IA; cat. n.o 7099). Water and food (Harlan Teklad™; cat. no. 8640) were available ad libitum. The mice were maintained on a cycle of 12 h of light and 12 h of dark in an environment with a temperature of 74-76° C. and 40-60% humidity. All cages underwent 40 air changes hourly in the negative pressure mode, in accordance with manufacturer's recommendations. Both the intake and exhaust air from the system were filtered through HEPA filters to maintain a clean environment. Stock solutions of BzFβ were solubilized in alkaline water (pH 10) and then sterile filtered through 0.22 μm syringe filters. BzFβ used for iv or im injections was diluted in 0.9% saline (normal saline). The stock solutions of the SIINFEKL peptide (SEQ ID NO: 1) were prepared in 1× calcium/magnesium free Dulbecco's phosphate-buffered saline (DPBS; ThermoFisher Scientific, cat. no. 14190144).

Since the oral route of drug delivery is preferred, various doses of BzFβ (1, 2, 4 mg) were administered by oral gavage, immediately following an iv injection of 50 μg SIINFEKL peptide. One-hour post-treatment the blood and spleens from each mouse was collected. Blood samples were processed as described above. Spleens were collected in 4 mL of Hanks Balanced Salt Solution (HBSS) and converted to a single cell suspension using sterile pouches and a Steward Stomacher 80 Biomaster Blender (Fisher Scientific, cat. no. 14-285-27). The resulting cell suspension was pelleted and suspended in 4 mL freshly prepared red blood cell lysis buffer (150 mM $NH_4Cl$, 10 mM $NaHCO_3$, 0.1 mM EDTA in sterile distilled $H_2O$) for 1-3 minutes. The splenocytes were pelleted and filtered through 70 μM EASYstrainer filters (USA Scientific, cat. no. 5654-2070). The cell count was determined using the MUSE cell viability kit (MCH600103) and MUSE Cell Analyzer (Luminex Corp, Austin TX).

One hour later the splenocytes were isolated and immediately tested for peptide loading or used to activate B3Z cells. For T-cell activation, splenocytes were prepared to $5\times10^5$/mL in cRPMI, then 100 μL of cells was added to wells of clear round-bottom 96 well tissue culture plates. The cells were incubated with 100 μL of B3Z cells, at a concentration of $5\times10^5$/mL, were added to each well. The cells were cocultured for 19 h. After 19 h, the media was removed and 100 μL of freshly prepared CPRG lysis buffer was added. The colorimetric response was allowed to develop for 15-240 min and the OD 560 nm was measured at various time points using a Synergy HTX plate reader. This assay was performed in replicates with both male and female C57BL/6 mice.

For peptide loading, splenocytes were prepared to $5\times10^5$/mL in cRPMI, then 100 μL of cells was added to wells of clear round-bottom 96 well tissue culture plates. The cells were incubated at 37° C. and treated for various times as indicated in results and figure legends. Cells were centrifuged and washed using cold FACS buffer (DPBS with 5% FBS, 2 mM EDTA, 0.1% sodium azide). Cells were blocked using Fc block (bioLegend™; cat. no. 101320) for 10 min to 15 min to inhibit non-specific binding, followed by staining with fluorophore-conjugated antibodies as specified: Super Bright 600-labeled MHC class II (I-A/I-E) (Invitrogen™, Thermo Fisher Scientific Inc., Waltham, MA; cat. no. 63-5321-82) FITC-labeled CD54 (Invitrogen™; cat. no. 11-0541-81), PE-labeled MHC class I H-2 kb specific (clone AF6-88.5.5.3; Invitrogen™; cat. no. 12-5958-82), PE-labeled anti-MHC I/SIINFEKL (clone 25-D1.16, Invitrogen™; cat. no. 12-5743-82), FITC-labeled CD45.2 (Invitrogen™; cat. no. 11-0454-82), APC-labeled CD11c (Invitrogen™; cat. no. 17-0114-81) for 30 min at 4° C. After washing, the cells were subjected to flow cytometric analysis with the Attune NxT Flow Cytometer (Invitrogen™). Cells were gated based on live single-cell populations and positives were assessed using isotype controls and fluorminus-one analysis when needed. Data were analyzed using the Attune NxT software or FlowJo versions 10.7 and 10.8.

If BzFβ had facilitated the in vivo loading of SIINFEKL it was expected that the peptide-bearing splenocytes would be able to activate B3Z. Since the oral route of drug delivery is preferred, various doses of BzFβ (1, 2, 4 mg) were administered by oral gavage, immediately following an iv injection of 50 μg SIINFEKL peptide. One hour later the splenocytes were isolated and immediately used to activate B3Z cells. If BzFβ had enhanced the in vivo loading of SIINFEKL it was expected that the peptide-bearing splenocytes would be able to enhance B3Z activation. As shown in FIG. 29, the splenocytes indeed activated the B3Z cells and did so in a manner that was dependent on the dose of BzFβ that had been administered. These splenocytes elicited a significantly greater response from the B3Z than those from the mice administered peptide alone.

To determine if BzFβ could facilitate peptide exchange when delivered by other routes, mice were injected iv with 50 μg of SIINFEKL, then immediately either gavaged with 1 mg BzFβ, iv injected with 50 μg BzFβ, or im injected with 100 μg of BzFβ. One hour later, the splenocytes from these mice were used ex vivo to stimulate B3Z activation. All three routes of administration were successful at enhancing the ability of the splenocytes to activate B3Z. As anticipated, the delivery of peptide and BzFβ via iv injection produced the greatest response, as seen in FIG. 30.

When splenocytes within the CD45+/MHC II/CD11c+ population were examined by flow cytometry, it was discovered that significantly more of these cells from the BzFβ treated mice co-expressed MHCI bound SIINFEKL, as seen in FIG. 31 ($p<0.001$). Since this phenotype is most often associated with classic dendritic cells, these results suggest that administration of BzFβ could potentially enhance the targeting of therapeutically relevant peptides to dendritic cells, which could lead to enhancement of a clinically relevant immune response.

Example 13: BzFβ is Nontoxic Following Oral Gavage or Intramuscular Injection Six-to ten-week-old male and female C57BL/6NCrl mice (cat. no. 027, Charles River Laboratories, Wilmington MA) were used for all animal studies. The mice were maintained in accord with the NIH Guide for the Care and Use of Laboratory Animals. Experimental procedures were performed in accord with research protocols approved by the Tampa Bay Research Institute's Institutional Animal Care and Use Committee. Mice were maintained in an INOVIVE individually ventilated cage system with 3 mice per cage containing 100% virgin wood pulp bedding (Harlan Teklad™, Harlan Sprague Dawley Inc., Indianapolis, IA; cat. no. 7099). Water and food (Harland Teklad™; cat. no. 8640) were available ad libitum. The mice were maintained on a cycle of 12 h of light and 12 h of dark in an environment with a temperature of 74-76° C. and 40-60% humidity. All cages underwent 40 air changes hourly in the negative pressure mode, in accordance with manufacturer's recommendations. Both the intake and exhaust air from the system were filtered through HEPA filters to maintain a clean environment. Stock solutions of BzFβ were solubilized in alkaline water (pH 10) and then sterile filtered through 0.22 μm syringe filters. BzFβ used for iv or im injections was diluted in 0.9% saline (normal saline).

Mice were gavaged with BzFβ at doses ranging from 25 mg/kg body to 100 mg/kg body weight, injected intravenously (iv) with 50 μg BzFβ or injected intramuscularly with BzFβ at 25 to 40 mg/kg body weight. For two weeks post-treatment, water intake and weight were monitored. At the end of the two-week period, the body and organ weights were measured to evaluate health outcomes, but no differences were measured. The limit to the solubility of BzFβ in alkaline water is 4 mg, therefore no further doses were tested. These results demonstrate that at the doses tested, in vivo administration of BzFβ is non-toxic.

Example 14: BzFβ Enhances the In Vitro Peptide Loading of DC Under Conditions Used to Generate DC Vaccines The DC2.4 (Dr. Kenneth Rock, University of Massachusetts) were routinely cultured in complete Dulbecco's Modified Eagle Medium (cDMEM) containing 4500 mg/mL glucose (Gibco™, cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems cat. no. 11150H) at 37° C. in an atmosphere containing 5% $CO_2$ and 95% humidity.

Cultured cells were treated for various times as indicated in results and figure legends. Cells were centrifuged and washed using cold FACS buffer (DPBS with 5% FBS, 2 mM EDTA, 0.1% sodium azide). Cells were blocked using Fc block (bioLegend™; cat. no. 101320) for 10 min to 15 min to inhibit non-specific binding, followed by staining with fluorophore-conjugated antibody PE-labeled anti-MHC I/SIINFEKL (clone 25-D1.16, Invitrogen™ 12-5743-82), for 30 min at 4° C. with Fc block (bioLegend™; cat. no. 101320) to inhibit non-specific binding. After washing, the cells were subjected to flow cytometric analysis with the Attune NXT Flow Cytometer (Invitrogen™). Cells were gated based on live single-cell populations and positives were assessed using isotype controls and fluor-minus-one analysis when needed. Data were analyzed using the Attune NxT software or FlowJo versions 10.7 and 10.8.

Previous experiments demonstrated that BzFβ can significantly enhance the binding of low concentrations (nM) of SIINFEKL. When dendritic cells are pulsed in vitro with peptide for the generation of DC vaccines, higher concentrations (1-10 μM) of peptide are often used. Since a pulse with 1 μg/mL of peptide is most commonly reported, the effects of a 2 h pretreatment with 50 μg/mL BzFβ prior to pulsing DC2.4 cells for 1 h with 1, 5, or 10 μg/mL SIINFEKL were examined. Surface levels of MHC class I/SIINFEKL complexes were detected by flow cytometry following staining with the PE-labeled 25-D1.16 antibody. While peptide alone was able to bind to nearly all of the DC2.4 cells, as seen in FIG. 32A, significantly more peptide was detected per cell if they had been pre-treated with BzFβ, seen in FIG. 32B.

Example 15: Immunization Using DC2.4 Cells Matured by Exposure to IFNγ and then Pre-Treated In Vitro with BzFβ and then with an MHC I Peptide, Enhances Generation of Antigen Specific CD8+ T Cells The DC2.4 cells (Kenneth Rock, University of Massachusetts) were routinely cultured in complete Dulbecco's Modified Eagle Medium (cDMEM) containing 4500 mg/mL glucose (Gibco™, cat. no. 10566-016) and supplemented with GlutaMAX, 50 U/mL penicillin and 50 μg/mL streptomycin (Gibco™, cat. no. 15070-063) and 10% heat inactivated fetal bovine serum (FBS) (R&D Systems cat. no. 11150H) at 37° C. in an atmosphere containing 5% $CO_2$ and 95% humidity.

DC2.4 cells that had been matured by an overnight treatment with 20 ng/ml murine IFNγ (He, et al., Interferon gamma stimulates cellular maturation of dendritic cell line DC2.4 leading to induction of efficient cytotoxic T cell responses and antitumor immunity. Cell Mol Immunol. 2007; 4 (2): 105-11) were treated with 30 μg/mL mitomycin C to block replication and were then pulsed for 1 h with 1 μg/mL SIINFEKL peptide (Group 2), or with 50 μg/mL BzFβ for 1 h and then with 1 μg/mL SIINFEKL peptide for 1 h (Group 3).

Six-to ten-week-old male and female C57BL/6NCrl mice (cat. no. 027, Charles River Laboratories, Wilmington MA) were used for all animal studies. The mice were maintained in accord with the NIH Guide for the Care and Use of Laboratory Animals. Experimental procedures were performed in accord with research protocols approved by the Tampa Bay Research Institute's Institutional Animal Care and Use Committee. Mice were maintained in an INOVIVE individually ventilated cage system with 3 mice per cage containing 100% virgin wood pulp bedding (Harlan Teklad™, Harlan Sprague Dawley Inc., Indianapolis, IA; cat. no. 7099). Water and food (Harland Teklad™; cat. no. 8640) were available ad libitum. The mice were maintained on a cycle of 12 h of light and 12 h of dark in an environment with a temperature of 74-76° C. and 40-60% humidity. All cages underwent 40 air changes hourly in the negative pressure mode, in accordance with manufacturer's recommendations. Both the intake and exhaust air from the system were filtered through HEPA filters to maintain a clean environment. Stock solutions of BzFβ were solubilized in alkaline water (pH 10) and then sterile filtered through 0.22 μm syringe filters. BzFβ used for iv or im injections was diluted in 0.9% saline (normal saline). The stock solutions of the SIINFEKL peptide (SEQ ID NO: 1) were prepared in 1× calcium/magnesium free Dulbecco's phosphate-buffered saline (DPBS; ThermoFisher Scientific, cat. no. 14190144).

Female C57BL/6crl mice were separated into 3 groups with 6 mice per group. The mice in Group 1 served as the naïve, no treatment group, Group 2 treated with by subcutaneous injection of $1.2\times10^6$ DC2.4 cells primed with IFNγ, mitomycin C and SIINFEKL, and Group 3 treated by subcutaneous injection of $1.2\times10^6$ DC2.4 cells primed with BzFβ and SIINFEKL as outlined above. One week later, the same mice were boosted with $1.2\times10^6$ DC2.4 cells that had been treated as described. Fourteen days later, the number of MHC class I/SIINFEKL tetramer positive CD8' cells in the peripheral blood and spleen were determined.

On day 21 (14 days after the last immunization) blood was collected from the retro-orbital plexus. The red blood cells were lysed using RBC lysis buffer and the white blood cells (WBC) were pelleted at 500× g for 2 min. The WBC were washed in FACS buffer (DPBS containing 2% FBS and 0.1% sodium azide), pelleted, and suspended in 50 μL FACS buffer containing 10 μL of the iTAG APC-labeled class I H-$2K^b$ OVA (SIINFEKL) tetramer (MBL International, cat. no. TB-5001-2). The cells were incubated for 30 min at room temperature while being protected from the light. Next, 40 μL of FACS buffer containing 0.4 μL of FITC-labeled anti-CD8 (clone KT15) (Fisher Scientific, cat. no. MA5-16759) and 1 μL of eFluor450-labeled anti-CD19 (clone eBio1D3 (1D3)) (Fisher Scientific, cat. no. 48-0193-80) was added and incubated at 10° C. for 30 min. The cells were washed with 3 mL FACS buffer, pelleted, and fixed for 1 h at 10° C. in 1 mL of FACS buffer containing 0.5% paraformaldehyde. The number of CD19 negative/CD8 positive/SIINFEKL tetramer positive cells was determined by flow cytometric analysis following collection of positive events detected in the lymphocyte gate.

Spleens were isolated and processed as previously described and then stained with antibodies specific for CD19, CD8, and tetramers specific for TCR's recognizing $H_2K^b$ presenting the SIINFEKL peptide.

The results show an enhanced SIINFEKL-specific CD8+ T cell response in mice immunized with BzFβ treated DC2.4, as seen in FIGS. 33A and 33B.

Example 16: PLGA Encapsulated BzFβ Enhances the Anti-Tumor Immune Response Generated by PLGA Encapsulated Whole Ovalbumin Six-to ten-week-old male and female C57BL/6NCrl mice (cat. no. 027, Charles River Laboratories, Wilmington MA) were used for all animal studies. The mice were maintained in accord with the NIH Guide for the Care and Use of Laboratory Aanimals. Experimental procedures were performed in accord with research protocols approved by the Tampa Bay Research Institute's Institutional Animal Care and Use Committee. Mice were maintained in an INOVIVE individually ventilated cage system with 3 mice per cage containing 100% virgin wood pulp bedding (Harland Teklad, cat. no. 7099). Water and food (Harland Teklad cat. no. 8640) were available ad libitum. The mice were maintained on a cycle of 12 h of light and 12 h of dark in an environment with a temperature of 74-76° C. and 40-60% humidity. All cages underwent 40 air changes hourly in the negative pressure mode, in accordance with manufacturer's recommendations. Both the intake and exhaust air from the system were filtered through HEPA filters to maintain a clean environment. Stock solutions of BzFβ were solubilized in alkaline water (pH 10) and then sterile filtered through 0.22 μm syringe filters. BzFβ used for iv or im injections was diluted in 0.9% saline (normal saline). The stock solutions of the SIINFEKL peptide were prepared in 1× calcium/magnesium free Dulbecco's phosphate-buffered saline (DPBS; ThermoFisher Scientific, cat. no. 14190144).

PLGA microparticles were prepared by dissolving 200 mg PLGA (poly(D,L-lactide-co-glycolide, Resomer® RG 752 H, acid terminated, lactide: glycolide 75:25, $M_w$ 4,000-15, 000 from Sigma) in 2 mL solvent (ethyl acetate, EtAc) in a 15 mL polypropylene centrifuge tube. Whole ovalbumin (40 mg, Fraction V, Sigma) was solubilized in 400 μL 1% polyvinyl alcohol (PVA, average mw of 30,000-70,000; Sigma) in a 5 ml conical centrifuge tube by vortexing for several minutes. The solubilized ovalbumin was then added, dropwise into the 2 mL PLGA mixture with continuous vortexing. To create an O/W emulsion, the mixture was placed into an ice bath and subjected to sonication (40% power, 50% pulses for 1 minute). The resulting emulsion was mixed with 8 mL of 1% PVA and sonicated as described above for 1 minute. The emulsion was then transferred to a 100 ml beaker containing 50 mL of 0.1% PVA. This was stirred with a magnetic stirrer (700 rpm) for a minimum of 3 h to evaporate the ethyl acetate and harden the particles.

The PLGA/BzFβ particles were prepared by adding 190 mg of PLGA and 20 mg BzFβ to a 15 mL polypropylene test tube. One milliliter of EtAc was added to the tube and then vortexed on high until the powders had completely dissolved (~10 min). A solution of 0.1% PVA was prepared and 2 mL placed of into a separate 15 mL tube and vortexed on high. While this was being vortexed, the 1 mL of the PLGA/BzFβ/EtAc solution was added dropwise into the 0.1% PVA. Once the polymer solution had been added to the PVA, the mixture was vortexed for an additional 15 sec. The emulsified polymers were immediately placed in an ice bath and the probe (⅛" diameter) of a Branson Sonifier 450 ultrasonicator was placed into the tube. The mixture was sonicated in three 10 sec bursts using 30% amplitude. The emulsion was move up and down the probe to ensure even sonication, being careful to avoid touching the probe to the sides or bottom of the test tube. Sonication was paused between each ten second pulse to allow the solution to cool before proceeding. Next, 50 ml of 0.1% PVA was added to a 200 ml glass beaker which was placed on a magnetic stir plate and stirred at 600 rpm. The emulsion was added to the beaker and stirred for a minimum of 3 hours. This allowed the solvent to evaporate and the particles to harden.

The number of OVA encapsulated in the PLGA particles was determined using the micro-bicinchoninic acid (BCA) assay kit (Pierce, Rockford, IL) following the manufacturer's instructions. Briefly, a standard curve of 2-fold serial dilutions of OVA (50-0 μg/mL) was prepared in particle lysis buffer (0.1% SDS and 0.1 N NaOH). Then, for each lot of OVA particles, 2-fold serial dilutions were prepared in particle lysis buffer (50% down to 7.8%). One hundred and fifty microliters of each dilution were mixed with 150 μL of the Micro BCA assay solution, incubated at 37° C.×2h, cooled to room temperature, and the next day the absorbance was read at 562 nm. The standard curve was used to determine the concentration of OVA in each of the particle dilutions.

FITC-labeled ovalbumin was encapsulated in PLGA as follows. Dissolved 200 mg PLGA in 2 mL ethyl acetate (75:25) in a 5 mL polypropylene centrifuge tube. Dissolved 40 mg of ovalbumin and 0.5 mg FITC-labeled ovalbumin (ThermoFisher cat #023020) in 400 μL H2O. To create an O/W emulsion, the PLGA solution was added dropwise into the OVA solution while vigorously vortexing. The mixture was then homogenized with a handheld homogenizer (TISSUEMISER, Fisher Scientific) at top speed for 3 min on ice. To form the W/O/W mixture, the resulting emulsion was mixed with 8 mL of 5% PVA in a 50 mL glass beaker and stirred with a magnetic stirrer for 5 min. The emulsion was then transferred to a 250 ml beaker containing 200 mL of 0.1% PVA and was stirred with a magnetic stirrer for 3 h to evaporate the ethyl acetate and harden the particles. The resulting mixture was transferred into four Oakridge centrifuge tubes and the particles were pelleted at 20,000×g for 15 min. Each pellet was suspended in 30 mL DPBS and pelleted 3 more times. After the last wash, the particles were suspended in a total of 4 mL H2O and 1 mL aliquots were transferred into four 5 mL polypropylene conical centrifuge tubes. The particles were lyophilized overnight. One of the lyophilized pellets was suspended in 1 mL H2O.

PLGA particles were collected as follows. The resulting solution was transferred into a 50 mL polypropylene centrifuge tube and very large particles were pelleted at 50× g for 2 min. The smaller particles remained in suspension and were transferred into two Oak Ridge tubes that were then placed in a Beckman JA-20 fixed angle rotor and pelleted at 20,000×g for 15 min. The pellets were each washed with 20 mL H2O, combined in a single tube and re-pelleted. The single pellet was washed in a total of 30 mL H2O and pelleted (20,000×g for 15 min). The particles were suspended in a total of 4 mL water, sonicated in a Vevor, Model JPS-30A, 180W ultrasonic water bath for 3 min to break up any clumps of particles that occurred during centrifugation. The particles were transferred in 1 mL aliquots into 5 mL pre-weighed polypropylene tubes, lyophilized overnight in a system composed of a Savant SC210A SpeedVac concentrator, a Savant RVT 5105 refrigerated vapor trap, and a VLP 120 vacuum pump. After lyophilization, the tubes were weighed to determine the mass of PLGA particles. The particles in one of the tubes were suspended in 1 mL water and the amount of ovalbumin or BzFβ that had been encapsulated was determined. The remaining tubes were kept at 10° C.

BzFβ encapsulated PLGA particles were quantified as follows. The lyophilized pellet in one of the tubes was suspended in 1 mL sterile H2O by vigorous vortexing. Dilutions of the PLGA/BzFβ particles were prepared in triplicate wells of a 96 well UV-transparent plate (UV-STAR ultraviolet transparent plate, USA Scientific, Ocala, FL). To the first set of wells was added 175 μL particle lysis buffer (0.1% SDS and 0.1 N NaOH) and 25 μL of BzFβ particles (makes a 12.5% solution). Starting with the 12.5% dilution, two more 2-fold dilutions were prepared in particle lysis buffer (making solutions containing 6.25% and 3.13% of the particles). The absorbance at 280 nm was obtained and the concentration of BzFβ determined from the standard curve (after subtracting the absorbance obtained from the lysis buffer only).

FITC-OVA PLGA particles were uptaken by DC2.4 cells as follows. DC2.4 cells (1 mL at $4\times10^4$/mL) were seeded into wells of a 24 well plate and allowed to adhere overnight. The next day, various dilutions of the FITC-OVA particles were added to the cells for 2 h. The wells were washed with HBSS and then the cells were released by incubating them for 10 min in 100 μL DPBS containing 3% EDTA. The cells were suspended in 1 mL FACS buffer (DPBS containing 5% FBS, 2 mM EDTA, and 0.1% sodium azide) and examined for particle uptake using ThemoFisher Scientific's ATTUNE NxT flow cytometer.

In triplicate wells of a 96 well flat bottom plate, 100 μL of complete DMEM (cDMEM, 10% FCS, 100 U/mL penicillin, and 100 μg/mL streptomycin) containing DC2.4 at $2\times10^5$/mL were plated and allowed to adhere for 4 hours. The cells were then treated by adding 100 μL of media containing enough particles to deliver 320, 160, 80, 40, 20, 10, or 5 μg/mL of ovalbumin. The cells were treated overnight. The next day, the cells in each well were washed with HBSS×3 and then a total of $2\times10^4$ B3Z cells were added and co-incubated overnight. The next day, the media was removed from the cells and 100 μL of CPRG lysis buffer (DPBS containing 0.2% saponin, 20 mM MgCl2, 100 mM β2ME, and 100 mM chlorophenol red-β-D-galactopyranoside) was added. The plate was incubated at 37° C. The absorbance at 560 nm was measured at various time intervals (1-20 h) to detect activation of the NFAT-driven lacZ gene.

To test the effects of PLGA encapsulated BzFβ on the uptake, processing, and presentation of separately encapsulated whole ovalbumin by DC2.4, cells were plated at $2\times10^4$ DC2.4 cells in 100 μL cDMEM per well of a flat bottom 96 well clear plate. Allowed the cells to adhere for 1 h and then the media and non-adherent cells were flicked off. The media in triplicate wells was replaced with the following, 100 μL of cDMEM only, 50 μL of 160 μg/mL whole OVA in PLGA particles plus 50 μL cDMEM (OVA NP only), 50 μL of 80 μg/mL whole OVA and then 50 μL of 100 μg/mL BzF-NP, or 50 μL of 40 μg/mL whole OVA and then 50 μL of 100 μg/mL BzF-NP. The cells were then incubated overnight at 37° C. in an atmosphere of 5% $CO_2$. The next day, the media was flicked off the cells and the cells were washed 3 times with 100 μL DPBS. Then, $2\times10^4$ B3Z cells, suspended in 100 μL cRPMI, were added to all wells and incubated for 19 h. The media was flicked off the cells (B3Z cells adhere to the DC2.4 cells) and 200 μL of CPRG lysis buffer was added. Four hours later, the absorbance at 560 nM was measured and plotted.

Immunization using PLGA particles containing ovalbumin or BzFß was performed as follows. Tubes containing empty lyophilized PLGA particles or particles encapsulating ovalbumin or BzFβ, were freshly suspended in DPBS. Ten-week-old female C57Bl/6crl mice were randomly segregated into 4 groups with 5 mice per group. On days 0 and 10 the mice in Group 1 received an intramuscular (i.m., right rear leg) injection of 50 μL DPBS, the mice in Group 2 received the i.m. injection with enough particles to produce a dose of 50 μg ovalbumin (680 μg/40 μL of particles+10 μL DPBS), the mice in Group 3 received the injection of particles containing a mixture of empty particles (280 μg/9.7 μL of particles)+particles containing 50 μg ovalbumin (680 μg/40 μL of particles). The mice in Group 4 were injected i.m. with a mixture of particles containing 50 μg ovalbumin (680 μg/40 μL of particles) and 50 μg BzFβ (280 μg/10 μL particles).

On day 20, 10 days post the booster injection, the mice in all groups were shaved on their right flank and then injected subcutaneously with $1\times10^6$ live E.G7-OVA cells in 50 μL of 0.9% saline. Palpable tumors began to appear within 5-7 days. The width and length of the tumors were measured using digital calipers and the tumor volumes were calculated using the formula, $$\text{Volume} = (\text{greatest width}^{\wedge}2 \times \text{greatest length})/2$$

When the tumors became >15-20 mm in any dimension the mice were euthanized by $CO_2$ asphyxiation in their home cage. The flow rate of $CO_2$ was controlled by an AVMA approved EP-2200 Dual Preset Tank Regulator with Restrictors (EZ Systems, Palmer, PA).

Female C57BL/6crl (5 per group) were immunized by an intramuscular injection of 50 μL DPBS only (NoTx), 50 μL of OVA PLGA particles encapsulating 50 μg of OVA (OVA), and 50 μL of a mixture of OVA PLGA particles (50 μg OVA) and BzFβ PLGA particles encapsulating 50 μg of BzFβ (OVA/BzFβ). The mice were boosted with the same mixtures 10 days later. Ten days post-booster, the mice were injected with $1\times10^6$ E.G7-OVA tumor cells subcutaneously into the right flank. The greatest width and greatest length of the resulting tumors were measured every other day once palpable tumors had appeared, as seen in FIGS. 34 and 35. In FIGS. 8 through 11, it was demonstrated that BzFβ could significantly enhance the cross-presentation of whole ovalbumin by the dendritic cell line, DC2.4. To enhance the targeting of OVA to phagocytic APC in vivo, the protein was encapsulated in PLGA particles. BzFß was encapsulated in a separate preparation of PLGA particles. When mice were immunized with OVA particles, a mixture of OVA and empty particles, or a mixture of OVA and BzFβ particles, it was found that only the mix of OVA and BzFβ was able to significantly ($p\leq0.01$) suppress tumor growth, as seen in FIGS. 34 and 35. Neither OVA particles or the mix of OVA plus empty particles induced a tumor suppressive response. Therefore, the independent delivery of PLGA encapsulated BzFβ is able to enhance the presentation of Class I peptides generated from exogenously delivered whole proteins

Example 17

Herein, the mechanism by which BzFβ [(2E)-3-(1-benzofuran-5-yl) prop-2-eonic acid)] interacts with dendritic cells to subsequently enhance their ability to activate CD8+ T cells was examined. BzFβ is able to support peptide loading and displacement on H-2K$^b$, H-2 D$^b$, and HLA-A*02:01 MHC class I structures. Through the use of both peptides and whole proteins, the mechanism by which BzFβ is capable of enhancing cell surface display of peptides presented through both direct and cross-presentation was elucidated. Although there has been some debate of whether CD8+ T cell functional response is dependent on cross-presentation directly, or if direct presentation plays an underlying role (Wu, et al., Dual role of 3-methyladenine in modulation of autophagy via different temporal patterns of inhibition on class I and III phosphoinositide 3-kinase. J Biol Chem. 2010 Apr. 2;285 (14): 10850-61), data suggests that both modes of peptide presentation are enhanced via treatment with BzFβ. Enhancing peptide loading speed and capacity is critical for the development of practical DC-based vaccines, as current DC vaccine protocols are expensive and time consuming. (Wang, et al., Direct loading of CTL epitopes onto MHC class I complexes on dendritic cell surface in vivo. Biomaterials. 2018 November; 182:92-103). BzFβ allows for quick peptide loading within a span of hours, and more importantly, it functions in vivo, even after oral delivery, to enhance the loading of exogenous antigens.

The ability for BzFβ to exchange peptides was examined using a variety of methods. Not only was BzFβ able to rapidly exchange peptide in a cell-free setting for the creation of both A*02:01 and H-2K$^b$ tetramers, but it also facilitated peptide exchange on a variety of cell types (dendritic cells, microglial cells, and melanoma cells) that resulted in activation of a reporter CD8$^+$ T cell hybridoma, as seen in FIGS. 3 through 11. The versatility of BzFβ is also highlighted in its ability to displace both high and lower affinity peptides. When applied after the high affinity SIINFEKL peptide, BzFß was able to displace it, as seen in FIGS. 16 through 17B. The same activity was detected when HLA-A*02:01 tetramers were used in the QuickSwitch Quant assay, as seen in FIGS. 20A through 20C. This ability to facilitate rapid peptide exchange will allow BzFβ to be used in the rapid creation of MHC multimers for various immunodiagnostics. Furthermore, the in vivo data shows that this ability is translatable to use as a vaccine adjuvant allowing increased peptide loading in vitro and in vivo. This activity could be used to increase selection of peptide specific CD8+ T cells and increase their functional competence in a manner found in high peptide-dose vaccination protocols, but without the need for further peptide dose escalation. (Carretero-Iglesia, et al., High peptide dose vaccination promotes the early selection of tumor antigen-specific CD8 T-cells of enhanced functional competence. Front Immunol. 2020 Jan. 8; 10:3016).

Although the possibility remains that BzFβ could be affecting peptide binding by interacting with other regions of the MHC class I complex, the molecular docking studies support the experimental data that BzFβ binds with high affinity in the F pocket of the MHC class I and HLA-A*02:01 peptide binding grooves, as seen in FIGS. 21A through 22B. Among the binding pockets, the F pocket is the most important for the stability of the MHC class I peptide and accommodates the carboxyl terminal residue of the peptide. The stability of peptide binding is provided by hydrogen bonding between the peptide and specific residues in the vicinity of the F pocket. (Abualrous, et al., F pocket flexibility influences the tapasin dependence of two differentially disease-associated MHC Class I proteins. Eur J Immunol. 2015 April; 45 (4): 1248-57). According to docking studies, BzFβ is predicted to facilitate MHC class I stability and peptide binding though hydrogen bonding with the same residues previously reported to be critical for the binding of H-2K$^b$ peptides and the dipeptide, GL. (Saini, et al., Dipeptides promote folding and peptide binding of MHC class I molecules. Proc Natl Acad Sci USA. 2013 Sep. 17;110 (38): 15383-8). This binding motif could possibly facilitate not only exchange of bound peptides, but also result in an increased binding efficiency while the F pocket remains in the peptide receptive state. (Anjanappa, et al., Structures of peptide-free and partially loaded MHC class I molecules reveal mechanisms of peptide selection. Nat Commun. 2020 Mar. 11;11 (1): 1314). Data support both of these actions. BzFß not only works to increase turnover, as seen in FIGS. 16 through 17B, but when cells are treated with BzFβ for prolonged periods of time the density of MHC class I complexes increases on the cell's surface, as seen in FIGS. 12B and 13B.

Like BzFβ, dipeptides, including GL, have been described as being able to increase MHC class I stability and facilitate peptide exchange. (Saini, et al., Dipeptides catalyze rapid peptide exchange on MHC class I molecules. Proc Natl Acad Sci USA. 2015 Jan. 6;112 (1): 202-7; Hein, et al., Peptide-independent stabilization of MHC class I molecules breaches cellular quality control. J Cell Sci. 2014 Jul. 1; 127 (13): 2885-97). However, even though both BzFβ and GL interact with the MHC class I F pocket, the concentration of dipeptides required to either displace or enhance peptide binding is significantly higher (3-fold) than that required by BzFβ, as seen in FIG. 16. Also, unlike dipeptides which are rapidly destroyed in vivo (Newey H, Smyth D. The intestinal absorption of some dipeptides. J Physiol. 1959 Jan. 28;145 (1): 48-56; Adibi, et al., Influence of molecular structure on half-life and hydrolysis of dipeptides in plasma: importance of glycine as N-terminal amino acid residue. Metabolism. 1986 September; 35 (9): 830-6), BzFß is much more stable in the GI tract and bloodstream, providing more time to interact with cells and facilitate a functional peptide exchange, as seen in FIG. 29 through 31.

Detection of BzFβ in the blood plasma of mice, as quickly as 30 minutes and for as long as 3 h following oral administration, confirmed the predictions of the SwissADME program (Daina, et al., SwissADME: a free web tool to evaluate pharmacokinetics, drug-likeness and medicinal chemistry friendliness of small molecules. Sci Rep. 2017 Mar. 3;7 (1): 1-13) that BzFβ could be absorbed into the bloodstream from the GI tract. The BzFβ absorbed through the GI tract was intact and functional, seen in FIGS. 28A, 28B and 29. Although in vitro kinetic stability has been found to correlate with in vivo CD8+ T cell response in C57BL/6 mice, the true applicability in vivo immunological action has been debated. (Thirdborough, et al., Tapasin shapes immunodominance hierarchies according to the kinetic stability of peptide-MHC class I complexes. Eur J Immunol. 2008 February; 38 (2): 364-9; Celli, et al., Decoding the dynamics of T cell-dendritic cell interactions in vivo. Immunol Rev. 2008 February; 221 (1): 182-7). As such studies were undertaken in a murine model to determine the translational ability of BzFβ. In these studies, mice were injected intravenously with SIINFEKL peptide and then immediately thereafter, received BzFβ by gavage, intravenous, or intramuscular injections. One hour later, the splenocytes were isolated and co-cultured with reporter CD8+ T cell hybridoma cells (B3Z). The results demonstrated that the splenocytes from mice receiving both SIINFEKL and BzFβ, regardless of the route of BzFβ delivery, were able to activate the CD8+ B3Z cells to an extent significantly greater than that produced by splenocytes from mice receiving peptide alone, as seen in FIGS. 29 through 31. Upon further analysis of these splenocytes it was found that BzFβ was able to increase SIINFEKL binding in the dendritic cell population, as seen in FIG. 31. These findings suggest that BzFβ has the potential to be used in vivo to facilitate therapeutically and immunologically relevant peptide exchange.

In a cursory examination of the structure-activity relationship, it became clear that BzFβ's structure, particularly its state of conjugation, is critical for its function. When molecules that differed from BzFβ by their level of saturation, and hence their loss of aromaticity and reduction in hydrophobicity, were tested in the B3Z activation assay, SIINFEKL binding assay, and the peptide displacement assay, they all failed to achieve the same activity as BzFβ, as seen in FIGS. 24A through 26. These findings implicate the specific BzFβ structure in its ability to modulate MHC class I peptide binding.

BzFβ specifically targets MHC class I structures on the cell surface without interfering with common metabolic or inflammatory pathways (data not shown). This specificity allows BzFβ to be used in combination with known vaccine adjuvants and has the potential to increase efficacy of a wide range of modalities. Targeting extracellular surface receptors that are functionally used in the immune response has been shown to have the most potent effect in vivo when compared to other vaccine mechanisms (Kastenmüller, et al., Dendritic cell-targeted vaccines—hope or hype? Nat Rev Immunol. 2014 October; 14 (10): 705-11). It has been well established that immunotherapies in cancer are most effective when a multi-faceted approach is taken, BzFβ's targeted effect would allow for the use of other adjuvants, such as PD-1/PD-L1 checkpoint blockade or toll-ligand activators, in combination with BzFβ for a robust response. As previously mentioned, nearly all nucleated cells possess MHC class I on their cell surface, used for self-recognition, MHC class I peptides are nearly ubiquitous in the body. (Davis, et al., Natural killer cell adoptive transfer therapy: exploiting the first line of defense against cancer. Cancer J (Sudbury, Mass). 2015 November-Dec; 21 (6): 486-91). As such, the binding of BzFβ on the MHC class I molecule allows for its use on non-antigen presenting cells and opens the possibility for its use in other disease mechanisms that are exacerbated by diminished MHC class I functionality. BzFß might also be utilized to change the peptide profile on tumors that have induced a state of tolerance.

To test the hypothesis that BzFβ can enhance the generation of Class I antigen-specific anti-tumor responses, two clinically relevant vaccine models were examined. The first utilized the in vitro generation of a dendritic cell vaccine and monitored the in vivo development of antigen specific CD8+ T cells. As shown in FIG. 33A, immunization of mice with IFNγ matured DC cells that had been treated for 2 hours with BzFβ and then pulsed for 1 hour with SIINFEKL peptide, generated significantly more SIINFEKL specific tetramer positive CD8+ T cells in the peripheral blood and the spleen. DC that had been pulsed with SIINFEKL, but not pre-treated with BzFβ, generated much weaker responses. Vaccines aimed at inducing CD8+ T cell responses have seen promise in targeting and clearing pathogens. (Sei, et al., Peptide-MHC-I from endogenous antigen outnumber those from exogenous antigen, irrespective of APC phenotype or activation. PLOS Pathog. 2015 Jun. 24;11 (6): e1004941).

The second model utilized whole OVA and BzFβ that had been separately encapsulated in PLGA microparticles to induce an anti-tumor immune response. Immunization with OVA particles failed to produce a response capable of suppressing the growth of E.G7-OVA tumor cells. However, when the mice were immunized with a mixture of OVA and BzFβ particles, a significant suppression of tumor growth was observed, as seen in FIGS. 34 and 35. These findings strongly suggest that whether it is used in vitro to generate dendritic cell vaccines, or delivered orally, intravenously, intramuscularly, or via PLGA particles, BzFβ is capable of significantly enhancing the in vivo generation of a Class I CD8+ T cell vaccine response. The findings support BzFβ's therapeutic potential to be examined for use in nanoparticle, mRNA, DNA, peptide, dendritic cell vaccines, and to synergize with chemo- or immunotherapeutics to generate in situ anti-tumor vaccines.

In conclusion, the presentation of class I peptides is central to the generation of $CD8^+$ T cell responses. $CD8^+$ T cell responses are vital for tumor surveillance and immunological protection against intracellular pathogens. As such, the discovery of an orally available, non-peptide-based, small molecule, capable of modulating peptide exchange in vivo, is an important addition to the therapeutic arsenal. The ability of BzFβ to enhance peptide loading in vivo is currently being examined for the ability to enhance antitumor and antiviral immune responses generated by mRNA-, peptide-, CAR-T therapies, dendritic cell-based, and micro/nano particle vaccines. Furthermore, as demonstrated by its ability to alter peptide display on tumor cells (B16F10 melanoma and E.G7-OVA T cell lymphoma), as seen in FIDs. 10 and 16 through 17B, the potential of BzFβ to enhance tumor targeting by CTL and to alter peptide display on targets of cell-mediated autoimmune responses are being examined.

Example 18: BzFβ Niosome Microvesicle Carriers

Niosomes have shown benefits over liposomes in that the synthetic niosomes appear more chemically stable as vesicles, are easier to transport and store, are less expensive to manufacture, and possess increased permeability to the blood brain barrier. It is composed of synthetic amphiphilic surfactants and cholesterol that make up a bilayer membrane that is able to entrap hydrophilic solutions in the aqueous core of the vesicle.

Exemplary surfactants include, without limiting the scope of the invention, crown ether amphiphiles bearing a steroidal moiety, 1,2-dialkyl glycerol polyoxyethylene ether, hexadecyl poly-5-oxyethylene ether, hexadecyl poly-5-oxyethylene ether ($C_{16}EO_5$); octadecyl poly-5-oxyethylene ether ($C_{18}EO_5$); hexadecyl diglycerol ether ($C_{16}G_2$); sorbitan monopalmitate (Span 40) and sorbitan monostearate (Span 60), Solulan™ C24 (poly-24-oxyethylene cholesteryl ether), polysorbate 20, Span detergents, Brij detergents, such as Brij-35, and polyoxyethylene. Crown ethers are known in the art (Montserrat, et al., Light-induced charge injection in functional crown ether vesicles. J Am Chem Soc. 1980 Aug. 1; 102 (17): 5527-5529; Darwish & Uchegbu, The evaluation of crown ether based niosomes as cation containing and cation sensitive drug delivery systems. Int J Pharm. 1997 Dec. 15; 159 (2): 207-213; Uchegbu & Duncan, Niosomes containing N-(2-hydroxypropyl) methacrylamide copolymer-doxorubicin (PK1): effect of method of preparation and choice of surfactant on niosome characteristics and a preliminary study of body distribution. Int J Pharm. 1997 Sep. 12; 155 (1): 7-17). Exemplary solvents involved in noisome formation may include glycerol, oil, water, and combinations thereof.

Cholesterol stabilizes the vesicles by decreasing the permeability and enhancing solute retention (Uchegbu & Florence, Non-ionic surfactant vesicles (niosomes): physical and pharmaceutical chemistry. Adv Colloid Interface Sci. 1995 Jun. 27; 58 (1): 1-55; Nasseri, Effect of cholesterol and temperature in the elastic properties of niosomal membranes. Int J Pharm. 2005 Aug. 26; 300 (1-2): 95-101). In addition, negative charged molecules may be added to the bilayer-producing compounds, such as dicetyl phosphate, cetyl sulphate, phosphatidic acid, phosphatidyl serine, oleic acid, palmitic acid, which provide electrostatic stabilization to the vesicles and prevents vesicle aggregation (Uchegbu & Vyas, Non-ionic Surfactant Based Vesicles (Niosomes) in Drug Delivery. Int J Pharm., 1998 Oct. 15; 172 (1-2): 33-70; Manosroi, et al., Characterization of vesicles prepared with various non-ionic surfactants mixed with cholesterol. Colloids Surf B. 2003 Jul. 1; 30 (1-2): 129-138). The ability of the surfactant to form a vesicle depends on two factors, the Hydrophobic Lipophilic Balance (HLB) and the Critical Packing Parameter (CPP). The HLB is calculated using $$HLB = 20 \times Mh/M$$

where Mh is the molecular mass of the hydrophilic portion of the surfactant, and Mis the molecular mass of the whole niosome, giving a result on an arbitrary scale of 0 to 20. For the surfactant sorbitan monostearate, an HLB number between 4 and 8 was found to be compatible with vesicle formation (Uchegbu & Vyas, Non-ionic Surfactant Based Vesicles (Niosomes) in Drug Delivery. Int J Pharm., 1998 Oct. 15; 172 (1-2): 33-70).

The CPP is a dimensionless number that predicts the ability of the amphiphile to form aggregates, with values of 0.5-1.0 predicting that the amphiphile will form a vesicle. (Israelachvili, Intermolecular and Surface Forces: With Applications to Colloidal and Biological Systems. 3d Ed. 2011, Orlando: Academic Press). CPP is calculated using $$CPP = v/l_c a_o$$

where v=hydrocarbon chain volume, $1_c$=critical hydrophobic chain length (the length above which the chain fluidity of the hydrocarbon may no longer exist), and $a_o$=area of hydrophilic head (Uchegbu & Florence, Non-ionic surfactant vesicles (niosomes): physical and pharmaceutical chemistry. Adv Colloid Interface Sci. 1995 Jun. 27; 58 (1): 1-55).

The niosomes are formed from the self-assembly of non-ionic amphiphiles in aqueous media resulting in closed bilayer structures (Uchegbu & Vyas, Non-ionic surfactant based vesicles (niosomes) in drug delivery. Int J Pharm., 1998 Oct. 15; 172 (1-2): 33-70). The assembly into bilayers is rarely spontaneous and usually involves some input of energy such as physical agitation or heat. Span 60, a surfactant, a cholesterol, and, optionally, dicetyl phosphate and/or sorbitan monosterate, a negatively charged molecule, are added to a flask in an organic solvent at a ratio of 1:1: (0.1), surfactant to cholesterol to dicetyl phosphate. The solution is mixed by agitation over a 60° C. bath until the solids dissolve and the solution transferred to an evaporator, such as a buchï rotary evaporator with nitrogen gas until a film forms on the flask. The flask is allowed to further dry for at least 12 hours, and the film hydrated using a solution of BzFβ. The solution is further dried in the rotary evaporator until the thin film dissolves and the niosomes extruded at 60° C., resulting in size-limited niosomes containing BzFβ. The niosomes are separated from unincorporated BzFβ by centrifugation at 60000 rpm for 40 minutes.

These niosomes have been found to exhibit a linear behavior in their size distribution as the concentration of the hydrophilic component increases from 5 millimolar to 15 millimolar. (Alcantar, et al., U.S. Pat. No. 9,522,114).

Example 19: Protein Niosome Microvesicle Carriers

Protein-loaded niosomes are useful in combination with systemic administration of BzFβ. The protein-loaded niosomes are formed from the self-assembly of non-ionic amphiphiles in aqueous media resulting in closed bilayer structures (Uchegbu & Vyas, Non-ionic surfactant based vesicles (niosomes) in drug delivery. Int J Pharm., 1998 Oct. 15; 172 (1-2): 33-70). A solution of Span 60, a surfactant, a cholesterol, and, optionally, dicetyl phosphate and/or sorbitan monosterate, a negatively charged molecule, are added to a flask in an organic solvent at a ratio of 1:1: (0.1), surfactant to cholesterol to dicetyl phosphate. The solution is mixed by agitation over a 60° C. bath until the solids dissolve and the solution transferred to an evaporator, such as a buchï rotary evaporator with nitrogen gas until a film forms on the flask. The flask is allowed to further dry for at least 12 hours, and the film hydrated using a solution containing the antigen protein is mixed by agitation over a 60° C. bath until the solids dissolve and the solution transferred to an evaporator, such as a buchï rotary evaporator with nitrogen gas until a film forms on the flask. The flask is allowed to further dry for at least 12 hours, and the film hydrated using the compound in solution, as described in Example 18. The solution is further dried in the rotary evaporator until the thin film dissolves and the niosomes extruded at 60° C., resulting in size-limited niosomes containing BzFβ. The niosomes are separated from unincorporated BzFβ by centrifugation at 60000 rpm for 40 minutes.

Example 20: Combined BzFβ-Protein Niosome Microvesicle Carriers

The niosomes are formed from the self-assembly of non-ionic amphiphiles in aqueous media resulting in closed bilayer structures (Uchegbu & Vyas, Non-ionic surfactant-based vesicles (niosomes) in drug delivery. Int J Pharm., 1998 Oct. 15; 172 (1-2): 33-70). The assembly into bilayers is rarely spontaneous and usually involves some input of energy such as physical agitation or heat. Span 60, a surfactant, a cholesterol, and, optionally, dicetyl phosphate and/or sorbitan monosterate, a negatively charged molecule, are added to a flask in an organic solvent at a ratio of 1:1: (0.1), surfactant to cholesterol to dicetyl phosphate. The solution is mixed by agitation over a 60° C. bath until the solids dissolve and the solution transferred to an evaporator, such as a buchï rotary evaporator with nitrogen gas until a film forms on the flask. The flask is allowed to further dry for at least 12 hours, and the film hydrated using the compound in solution, as described in Example 1. The solution is further dried in the rotary evaporator until the thin film dissolves and the niosomes extruded at 60° C., resulting in size-limited niosomes containing BzFβ. The niosomes are separated from unincorporated BzFβ by centrifugation at 60000 rpm for 40 minutes.

Example 21: Niosome Target Microvesicle Carriers

Molecules are loaded onto the niosomes to permit the niosome delivery system to target cancer cells. Examples of methods to incorporate target molecules into the vesicle membrane are known in the art, but can include by way of non-limiting example, anti-integrin molecules specific to antigen presenting cells (APCs). Examples of integrin molecules specific to APCs include BDCA-1, CD1a, CD1c, CD11b, CD11c, CD123, CD141, CD207, and CD303, alone or in combination, as seen in Table 3. (Collin & Bigley, Human dendritic cell subsets: an update. Immunology. 2018 May; 154 (1): 3-20). Accordingly, anti-BDCA-1, anti-CD1a, anti-CD1c, anti-CD11b, anti-CD11c, anti-CD123, anti-CD141, anti-CD207, and anti-CD303, alone or in combination are loaded onto the niosomes. While the epitopes listed are for conventional dendritic cells (myeloid dendritic cells, it is within the skill of one of ordinary skill in the art to use the disclosed information to target other APC cell types.

TABLE 3

List of common integrins on human dendritic cells.

| Cell type | Conventional surface markers | Extended markers |
|---|---|---|
| Plasmacytoid DC | CD123 | FCER1 |
| | CD303, CLEC4c, BDCA-2 | ILT3, ILT7 |
| | CD304, NRP1, BDCA-4 | ILT3, ILT7 |
| Myeloid cDC1 | CD141, BDCA-1 | CLEC9A |
| | | CADM1 |
| | | XCR1 |
| | | BTLA |
| | | CD26 |
| | | DNAM-1, CD226 |
| Myeloid cDC2 | CD1c, BDCA-1 | CD-2 |
| | CD-11c | FCER1 |
| | CD-11b | SIRPA |
| | | ILT1 |
| | | DCI1, CLEC4A |
| | | CLEC10A |
| Langerhans cell | CD207 | EpCAM |
| | CD1a | TROP2 |
| | E-Caderin | |

Niosomes are prepared, as described in any of Examples 17 through 19, using PEG molecules that are modified to introduce an amino group. (Hong, et al., Efficient tumor targeting of hydroxycamptothecin loaded PEGylated niosomes modified with transferrin. J Control Release. 2009 Jan. 19; 133 (2): 96-102). Target molecules are conjugated to the PEG-amino group using an oxidation reaction, by oxidizing the target molecule and introducing the oxidized target molecule to the amino-PEG-niosomes. (Hong, et al., Efficient tumor targeting of hydroxycamptothecin loaded PEGylated niosomes modified with transferrin. J Control Release. 2009 Jan. 19; 133 (2): 96-102).

Example 22: Liposome Microvesicle Carriers

Lipid nanoparticles have been shown as an effective transport vehicle to deliver the compounds to biologic target cells. Such lipid nanoparticles are made by mixing a cationic lipid, non-cationic lipid, a polyethyleneglycol (PEG) conjugated lipid, and a structural lipid in a method similar to Example 16, and loaded with BzFβ, protein, or a combination of BzFβ and protein, as provided in Examples 15 through 19. In some variations, the lipid nanoparticles can be synthesized using a mixture of ionizable cationic lipid/phosphatidylcholine/cholesterol/PEG-lipid at a ratio of 50:10:38.5:1.5 mol/mol (cationic lipid: phosphatidylcholine: cholesterol: PEG-lipid), and encapsulate the BzFβ. The interaction between the liposomes and the cargo usually relies on hydrophobic interactions or charge attractions, particularly in the case of cationic lipid delivery systems (Zelphati, et al., Intracellular delivery of proteins with a new lipid-mediated delivery system. J Biol Chem. 2001 Sep. 14, 276 (37): 35103-35110). Modifications to the liposomes, by adding ionizable amino lipids as cationic lipid moieties, such as 2,2-dilinoleyl-4-dimethylaminoethyl-[1,3]-dioxolane, increase stability of liposome carriers.

Example 23: Microspheres

Alternatively, BzFβ, protein, or a combination of BzFβ and protein were incorporated into microspheres. (Harris, et al., A synthetic peptide CTL vaccine targeting nucleocapsid confers protection from SARS-COV2 challenge in rhesus macaques. are separated from unincorporated. Vaccines (Basel). 2021 May 18; 9 (5): 520; Herst, et al., An effective CTL peptide vaccine from Ebola Zaire based on survivors' CD8+ targeting of a particular nucleocapsid protein epitope with potential implications for COVID-19 vaccine design. Vaccine. 2020 Jun. 9; 38 (28): 4464-4475). Briefly, mannose, CpG oligonucleotide, and SINFEKL or other peptide were mixed with a solution of BzFβ in acetone/water (50:50 v: v). The solution was sonicated and extruded through a Büchi rotovaporator with extruder.

The BzFβ can be loaded into microvesicles or microparticle, such as niosomes or liposomes or microsphere, as disclosed in Examples 18 through 21, and the vesicles can optionally possess surface ligands to permit specific targeting to cancer cells or a cell type, allowing the carrier to interface with a cell expressing the conjugate ligand or molecule.

As shown herein, BzFß can enhance the generation of Class I antigen-specific responses. Immunization of mice through matured DC cells treated with BzFβ and exposed to an antigen peptide, generated significantly higher antigen-specific tetramer positive CD8+ T cells in the peripheral blood and the spleen. Vaccines aimed at inducing CD8+ T cell response have seen promise in targeting and clearing pathogens (Sei, et al., Peptide-MHC-I from endogenous antigen outnumber those from exogenous antigen, irrespective of APC phenotype or activation. PLOS Pathog. 2015 Jun. 24;11 (6): e1004941). This opens the door for BzFβ to be tested for use in various mRNA, peptide, as well as dendritic cell-based vaccines.

SEQUENCE LISTING

```
Sequence total quantity: 4
SEQ ID NO: 1            moltype = AA  length = 8
FEATURE                 Location/Qualifiers
source                  1..8
                        mol_type = protein
                        organism = Gallus gallus
SEQUENCE: 1
SIINFEKL                                                    8
```

-continued

```
SEQ ID NO: 2            moltype = AA  length = 9
FEATURE                 Location/Qualifiers
source                  1..9
                        mol_type = protein
                        organism = Homo sapiens
SEQUENCE: 2
SVYDFFVWL                                                   9

SEQ ID NO: 3            moltype = AA  length = 13
FEATURE                 Location/Qualifiers
source                  1..13
                        mol_type = protein
                        organism = synthetic construct
SEQUENCE: 3
SVYDFFVKFI TCL                                              13

SEQ ID NO: 4            moltype = AA  length = 9
FEATURE                 Location/Qualifiers
source                  1..9
                        mol_type = protein
                        organism = Human Papillomavirus
SEQUENCE: 4
RAHYNIVTF                                                   9
```

What is claimed is:

1. A method of modulating an immune response, comprising:
 - altering an antigen-presenting cell by exposing the antigen-presenting cell with a therapeutically effective amount of a first compound and a therapeutically effective amount of a second compound;
   - wherein the first compound is (2E)-3-(1-benzofuran-5-yl) prop-2-enoic acid;
   - wherein the second compound is an antigen molecule; and
 - contacting a lymphocyte with the antigen-presenting cell.

2. The method of claim 1, wherein the antigen-presenting cell is altered by:
 - contacting the antigen-presenting cell with the first compound for a first compound incubation period;
   - wherein the first compound incubation period is at least 15 minutes; and
 - subsequently contacting the antigen-presenting cell with the second compound for a second compound incubation period after expiration of the first compound incubation period.

3. The method of claim 2, wherein the first compound incubation period is between 1 hour and 24 hours.

4. The method of claim 2, wherein the second compound incubation period is between 1 hour and 24 hours.

5. The method of claim 1, wherein the antigen-presenting cell is altered by:
 - concurrently contacting the antigen-presenting cell with the first compound and with the second compound for a determined period of time.

6. The method of claim 1, wherein the antigen-presenting cell is altered in vivo by:
 - administering the first compound to a patient orally, intravenously, or intramuscularly; and
 - wherein the first compound contacts the antigen-presenting cell in vivo.

7. The method of claim 5, wherein the first compound and the second compound contact the antigen-presenting cell ex vivo to form a primed dendritic cell, and wherein the method further comprises administering the primed dendritic cell to a patient in need thereof.

8. The method of claim 1, wherein the antigen molecule is a small molecule antigen vaccine, an epitope vaccine, a DNA vaccine, a recombinant DNA vaccine, a messenger RNA vaccine, a subunit vaccine, a recombinant vaccine, a conjugate vaccine, an immunotherapy cancer antigen, or a toxoid vaccine.

9. A method of enhancing a vaccine, comprising:
 - altering the presentation of an antigen-presenting cell by contacting the antigen-presenting cell with a therapeutically effective amount of (2E)-3-(1-benzofuran-5-yl) prop-2-enoic acid and a therapeutically effective amount of the vaccine; and
 - stimulating a lymphocyte by contacting the lymphocyte with the antigen-presenting cell.

10. The method of claim 9, wherein the antigen-presenting cell is stimulated by:
 - contacting the antigen-presenting cell with the (2E)-3-(1-benzofuran-5-yl) prop-2-enoic acid for between 1 hour and 24 hours; and
 - subsequently contacting the antigen-presenting cell with the vaccine for between 1 hour and 24 hours.

11. The method of claim 9, wherein the (2E)-3-(1-benzofuran-5-yl) prop-2-enoic acid contacts the antigen-presenting cell ex vivo or in vitro at between 5 μg/mL and 100 μg/mL.

12. The method of claim 9, wherein the vaccine contacts the antigen-presenting cell ex vivo or in vitro at between 1 ng/ml and 100 μg/mL; and
 - wherein the vaccine contacts the antigen presenting cell at a range of 1 ng/ml to 10 μg/mL for a peptide vaccine, a range of 1 μg/mL to 100 μg/mL for a DNA vaccine, a range of 1 μg/mL to 25 μg/mL for a mRNA vaccine, or a range of 1 μg/mL to 20 μg/mL for a whole subunit protein vaccine.

13. The method of claim 9, wherein the antigen-presenting cell is a dendritic cell and wherein the dendritic cell is stimulated by:
 - contacting the dendritic cell with the 2E)-3-(1-benzofuran-5-yl) prop-2-enoic acid for between 1 hour and 24 hours; and
 - subsequently contacting the dendritic cell with the vaccine for between 1 hour and 24 hours.

14. The method of claim 13, wherein the dendritic cell is contacted by the (2E)-3-(1-benzofuran-5-yl) prop-2-enoic acid ex vivo at between 5 μg/mL and 100 μg/mL.

15. The method of claim 13, wherein the dendritic cell is contacted by the vaccine ex vivo at between 1 ng/ml and 100 μg/mL; and wherein the vaccine contacts the antigen presenting cell at a range of 1 ng/ml to 10 μg/mL for a peptide vaccine, a range of 1 μg/mL to 100 μg/mL for a DNA vaccine, a range of 1 μg/mL to 25 μg/mL for a mRNA vaccine, or a range of 1 μg/mL to 20 μg/mL for a whole subunit protein vaccine.

16. The method of claim 10, further comprising:

administering the stimulated lymphocyte to a patient in need of the vaccine; and contacting the antigen-presenting cell with (2E)-3-(1-benzofuran-5-yl) prop-2-enoic acid a second time by administering the (2E)-3-(1-benzofuran-5-yl) prop-2-enoic acid to a patient, wherein administering (2E)-3-(1-benzofuran-5-yl) prop-2-enoic acid is orally, intravenously, intra-arterially, intrathecally, or intraventricularly to the patient.

17. A method of preparing an immunotherapy, comprising:

obtaining an antigen-presenting cell from a patient in need thereof;

exposing the antigen-presenting cell with a therapeutically effective amount of a first compound and a therapeutically effective amount of a second compound;

wherein the first compound is (2E)-3-(1-benzofuran-5-yl) prop-2-enoic acid;

wherein the second compound is an antigen molecule;

incubating the antigen-presenting cell with the first compound and the second compound for at least one hour to form a primed antigen-presenting cell; and injecting the primed antigen-presenting cell into the patient.

18. The method of claim 17, wherein the exposing step further comprises:

contacting the antigen-presenting cell with the first compound for a first compound incubation period; and wherein the first compound incubation period is at least 15 min.

19. The method of claim 18, wherein the first compound incubation period is between 30 min and 2 h.

20. The method of claim 17, wherein the first compound is exposed to the antigen-presenting cell at between 1.62 μg/mL and 50 μg/mL.

21. The method of claim 18, wherein the second compound incubation period is between 1 hour and 24 hours.

22. A method of preparing an in vivo immunotherapy, comprising:

testing dendritic cell populations and CD8+ t-cells of a patient in need of tumor treatment;

confirming the dendritic cell populations and CD8+ t-cells of the patient in need of tumor treatment meets or exceeds a minimum threshold value;

administering a therapeutically effective amount of an antitumor therapy to the patient in need of tumor treatment;

wherein the antitumor therapy is chemotherapy, radiation, immunotherapy, hyperthermia, or photodynamic therapy; and administering a therapeutically effective amount of a first compound to the patient in need of tumor treatment orally, intravenously, intra-arterially, intrathecally, or intraventricularly;

wherein the first compound is (2E)-3-(1-benzofuran-5-yl) prop-2-enoic acid.

23. The method of claim 22, wherein the first compound is administered concurrently with the antitumor therapy.

* * * * *